(12) United States Patent
Harding et al.

(10) Patent No.: US 8,598,118 B2
(45) Date of Patent: Dec. 3, 2013

(54) HEPATOCYTE GROWTH FACTOR MIMICS AS THERAPEUTIC AGENTS

(71) Applicant: Washington State University, Pullman, WA (US)

(72) Inventors: Joseph W. Harding, Pullman, WA (US); John W. Wright, Pullman, WA (US); Caroline C. Benoist, Nashville, TN (US); Leen H. Kawas, Pullman, WA (US); Gary A. Wayman, Pullman, WA (US)

(73) Assignee: Washington State University, Pullman, WA (US)

( * ) Notice: Subject to any disclaimer, the term of this patent is extended or adjusted under 35 U.S.C. 154(b) by 0 days.

(21) Appl. No.: 13/768,497

(22) Filed: Feb. 15, 2013

(65) Prior Publication Data
US 2013/0165392 A1 Jun. 27, 2013

Related U.S. Application Data

(63) Continuation of application No. PCT/US2012/031815, filed on Apr. 2, 2012.

(60) Provisional application No. 61/471,122, filed on Apr. 2, 2011, provisional application No. 61/471,124, filed on Apr. 2, 2011.

(51) Int. Cl.
*A61K 38/22* (2006.01)
*C07K 14/475* (2006.01)

(52) U.S. Cl.
USPC .......................................................... 514/9.5

(58) Field of Classification Search
None
See application file for complete search history.

(56) References Cited

U.S. PATENT DOCUMENTS 6,777,388 B1 * 8/2004 Grasso et al. .................. 514/5.8
2005/0113369 A1   5/2005 Zembower et al.

FOREIGN PATENT DOCUMENTS

EP          0805203        5/1997
WO   WO 2008005531    *   1/2008
WO        2011/019400     2/2011

OTHER PUBLICATIONS

Yamamoto et al., "The angiotensin IV analog Nle-Tyr-Leu-psi-(CH2-NH2)3-4-His-Pro-Phe (norleual) can act as a hepatocyte growth factor/c-Met inhibitor"; The Journal of Pharmacology and Experimental Therapeutics, vol. 333(1), 2010, pp. 161-173.

* cited by examiner

*Primary Examiner* — Thomas Heard
(74) *Attorney, Agent, or Firm* — Whitham Curtis Christofferson & Cook, PC

(57) ABSTRACT

Small molecule, peptidic hepatocyte growth factors mimics, which act as both mimetics and antagonists, have been generated. These molecules have been shown or predicted to have therapeutic potential for numerous pathologies including dementia, neurodegenerative disease, diabetes and metabolic syndrome, cancer, and defective wound healing.

4 Claims, 21 Drawing Sheets

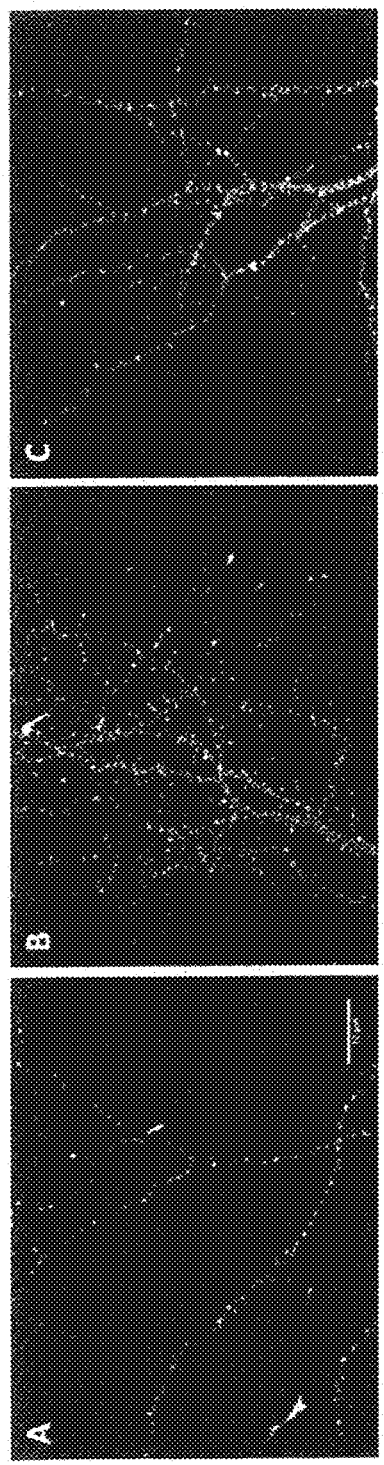
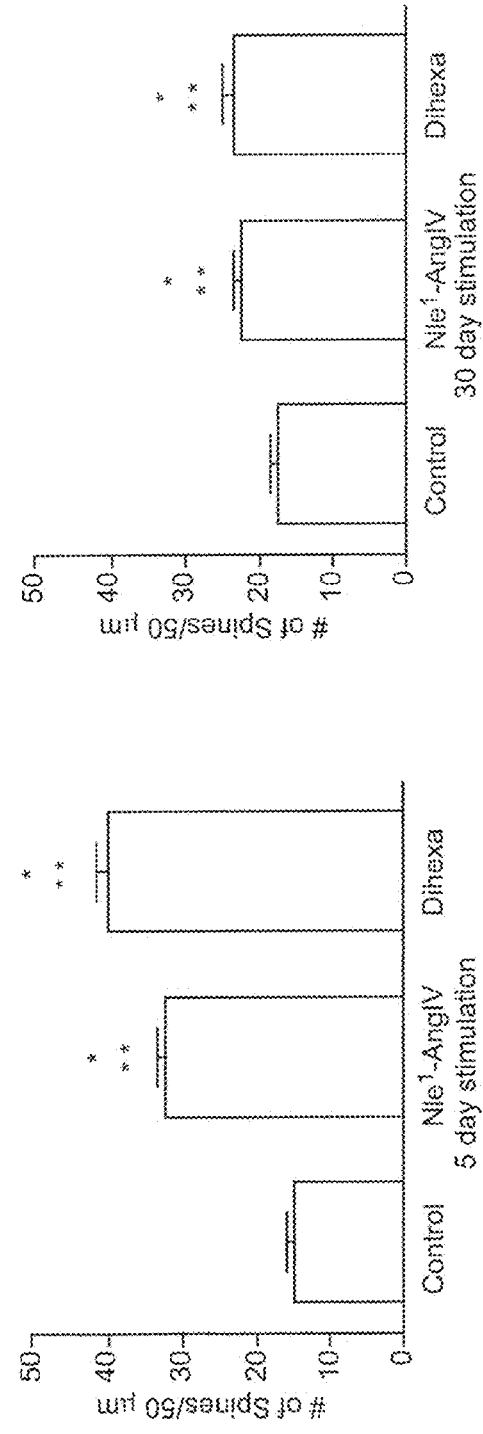
Figure 3A  Figure 3B  Figure 3C
Figure 3D
Figure 3E

SEQUENCE LISTING

```
<160> NUMBER OF SEQ ID NOS: 3

<210> SEQ ID NO 1
<211> LENGTH: 6
<212> TYPE: PRT
```

```
<213> ORGANISM: Artificial Sequence
<220> FEATURE:
<223> OTHER INFORMATION: Synthetic angiotensin ligand
<220> FEATURE:
<221> NAME/KEY: MISC_FEATURE
<222> LOCATION: (1)..(1)
<223> OTHER INFORMATION: Norleucine
<220> FEATURE:
<221> NAME/KEY: MISC_FEATURE
<222> LOCATION: (3)..(4)
<223> OTHER INFORMATION: A reduced peptide bond (-CH2-NH2-)

<400> SEQUENCE: 1

Xaa Tyr Leu His Pro Phe
1               5

<210> SEQ ID NO 2
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 2
gtgtcaggag gtgtttggaa ag                                        22

<210> SEQ ID NO 3
<211> LENGTH: 6
<212> TYPE: PRT
<213> ORGANISM: Artificial Sequence
<220> FEATURE:
<223> OTHER INFORMATION: Synthetic hinge peptide

<400> SEQUENCE: 3

Asp Tyr Ile Arg Asn Cys
1               5
```

HEPATOCYTE GROWTH FACTOR MIMICS AS THERAPEUTIC AGENTS

CROSS-REFERENCE TO RELATED APPLICATIONS

This application is a continuation of International Application No. PCT/US2012/031815, filed Apr. 2, 2012, which claims priority to U.S. Application No. 61/471,122, filed Apr. 2, 2011, and U.S. Application No. 61/471,124, filed Apr. 2, 2011, the complete contents of which are herein incorporated by reference.

STATEMENT OF FEDERALLY SPONSORED RESEARCH AND DEVELOPMENT

This invention was made, in part, with government support under Grant Nos. MH086032 awarded by NIH. The government has certain rights in the invention.

SEQUENCE LISTING

This application includes as the Sequence Listing the complete contents of the accompanying text file "Sequence.txt", created Apr. 2, 2012, containing 1022 bytes, hereby incorporated by reference.

SUMMARY

Field of the Invention

The invention generally relates to the development of hepatocyte growth factor (HGF) mimics that can act as mimetics (agonists) or antagonists. Mimetics act: to enhance cognitive function; as general neuroprotective/neuroregenerative agents; to facilitate wound repair; to improve insulin sensitivity and glucose transport; and to decrease tissue or organ fibrosis in order to prevent or reverse the symptoms of dementia, to protect from or reverse neurodegenerative disease, to facilitate repair of traumatic injury to the nervous system, to augment tissue and organ vascularization, to improve impaired wound healing, and to decrease or reverse fibrotic changes in organs like heart, lung, kidney, and liver. Antagonists act, for example, as anti-angiogenic and anti-cancer agents; to treat various malignancies and diseases like macular degeneration and diabetic retinopathy, which are associated with hypervascularization.

Mimetics:

Dementia:

There are approximately 10 million diagnosed dementia patients in the United States alone and that number continues to grow every year as the population ages. The costs of treatment and care of these patients are in excess of $70 billion annually and are increasing rapidly. Unfortunately, the current treatment options for the management of dementia are severely limited and largely ineffective. The lack of treatment options for a burgeoning health problem of this magnitude necessitates that new and innovative therapeutic approaches be developed as quickly as possible.

At its core dementia results from a combination of diminished synaptic connectivity among neurons and neuronal death in the entorhinal cortex, hippocampus and neocortex. Therefore, an effective treatment would be expected to augment synaptic connectivity, protect neurons from underlying death inducers, and stimulate the replacement of lost neurons from preexisting pools of neural stem cells. These clinical endpoints advocate for the therapeutic use of neurotrophic factors, which mediate neural development, neurogenesis, neuroprotection, and synaptogenesis. Not unexpectedly neurotrophic factors have been considered as treatment options for many neurodegenerative diseases including Alzheimer's disease (see reviews—Nagahara and Tuszynski, 2011; Calissano et al., 2010). One particularly attractive but mostly overlooked neurotrophic factor is HGF, which has a proven ability to both stimulate neurogenesis (Shang et al., 2011, Wang et al, 2011) and synaptogenesis (see preliminary studies below). The realization that HGF application might represent a viable treatment option for dementia should be no surprise. HGF is a potent neurotrophic factor in many brain regions (Kato et al., 2009; Ebens et al., 1996), while affecting a variety of neuronal cell types.

Neuroprotection/Neuroregeneration:

HGF and c-Met are actively expressed in both the developing and adult brains and nerves. The Met system is essential for both the central and peripheral nervous systems to function properly. A large number of studies have shown that HGF and c-Met are expressed in multiple areas of the brain including the frontal cortex, subependyma, thalamus, cerebellar cortex, deep gray matter, and the hippocampus, an important area for cognition.

The biological activities described above also characterize Met functions in the brain where HGF/c-Met signaling is neurotrophic (Honda et al., 1995) and protective (Zhang et al., 2000; Takeo et al., 2007; Tyndall and Walikonis, 2007; Takeuchi et al., 2008). Similar to its activities in other tissues, Met in the brain is involved in development, acting as a guidance factor during differentiation, motogenesis and neuritogenesis (Ebens et al., 1996; Sun et al., 2002; Tyndall and Walikonis, 2007). HGF/c-Met signaling has also been shown to promote healing of neuronal injury (Trapp et al., 2008), especially after ischemic brain injury (Takeo et al., 2007). HGF also displayed neuroprotective effects in animal models for neurodegenerative diseases including amyotrophic lateral sclerosis (ALS). The various functions of HGF, plus its highly potent neurotrophic activities, promote HGF as a potential therapeutic agent for the treatment of various diseases of the nervous system.

Amyotrophic Lateral Sclerosis:

ALS is a fatal rapid-onset neurodegenerative disease that is characterized by degeneration of motoneurons in the spinal cord and efferent neurons in the motor cortex and brainstem. The impact of this degeneration results in a progressive loss of muscle function culminating in total paralysis. Approximately 90% of the cases of ALS are classified as sporadic with no known etiology, while the remaining 10% appear to be familial, resulting in part from defects in copper/zinc superoxide dismutase 1 (SOD1), which leads to exaggerated oxidative stress and an unfolded protein response. The one thing that both forms of ALS have in common is that there is currently is no effective treatment available.

Despite the paucity of effective treatment options, several studies have highlighted the potential benefits of using hepatocyte growth factor (HGF) as a therapeutic agent. These investigations have demonstrated that application of hepatocyte growth factor (HGF) in a murine or rat model of familial ALS significantly slows motoneuron degeneration (Aoki et al., 2009); reduces gliosis (Kadoyama et al. 2007), which contributes to the degeneration process; delays the onset of paralysis (Kadayama et al., 2009); and increases lifespan (Sun et al., 2002).

The realization that HGF application might represent a viable treatment option for ALS, however, should be unexpected. HGF along with its type I tyrosine kinase receptor, c-Met, have long been recognized for their role in the development of tubular structures (Santos et al., 1993) and their general proliferative, anti-apoptotic, motogenic, and morphogenic actions on hepatocytes and cells of epithelial origin. Most pertinent, however, is the more recent realization that HGF is a potent neurotrophic factor (Maim and Klein, 1993; Kato et al., 2009) in many brain regions and that it is particularly effective as a pro-survival/regenerative factor for motoneurons (Ebens et al., 1996; Yamamoto et al., 1997; Hayashi et al., 2006; Elsen et al., 2009).

Parkinson's Disease:

A treatment option long considered for many neurodegenerative diseases including Parkinson's disease (PD) has been the application of growth factors with the intention of halting disease progression, restoring lost function, or hopefully both (review, Rangasamy et al., 2010). However, this dream has gone largely unfulfilled at the level of clinical medicine because of limitations related to brain delivery and costs. Growth factors are universally large proteins that are both metabolically labile and too large to pass the blood-brain barrier (BBB). As such, most approaches to delivery have utilized gene therapy methods with the hope that the growth factor will be expressed in the correct location at a high enough concentration and for a long enough period to provide clinical relief. Although a number of creative and successful approaches in animal models have been employed to deliver growth factors like GDNF (Wang et al., 2011) to the brain, these methodologies are technically complex and prohibitively difficult to bring to practice with large numbers of patients.

While many growth factor systems have been examined as potential therapeutic targets for PD one that has been largely, and we think mistakenly, overlooked is the hepatocyte growth factor (HGF)/c-Met (its type I tyrosine kinase-receptor) system. Nevertheless, the potential utility of HGF as a PD treatment has been highlighted in a study by Koike et al. (2006) in which an HGF plasmid injected directly into the substantia nigra (SN) resulted in localized over-expression of HGF, and acted dramatically to prevent neuronal cell death and preserve normal motor function in the 6-hydroxydopamine (6-OHDA) PD rat model. This observed neuroprotective effect of HGF on dopaminergic (DA) neurons meshes with its ability to augment the proliferation and migration of dopaminergic progenitor cells (Lan et al., 2008)

The neuroprotective effect of the HGF on the nigrostriatal pathway, however, should be no surprise given its recognized role in stem cell regulation, the development of tubular structures (Santos et al., 1993) and its general proliferative, anti-apoptotic, motogenic, and morphogenic actions on many cell types including hepatocytes and cells of epithelial origin (Gherardi et al., 1993). MaMa et al., Particularly pertinent is the demonstration that HGF is a potent neurotrophic factor for many neuronal cell types (Kato et al, 2009) including motoneurons (Eisen et al., 2009; Hayashi et al, 2006), hippocampal neurons Lim et al., 2008), cerebellar granular cells (Ieraci et al., 2002), and sympathetic neurons (1999). Moreover, HGF appears to be a critical regulator of neural stem cell expansion and differentiation (Nicoleau et al., 2009) suggesting that neural as well as many types of peripheral stem cells are under the control of the HGF/c-Met system.

Traumatic Brain Injury/Spinal Cord Injury:

TBI often negatively impacts cognitive function and can elicit effects that range from mild, with temporary decrements in mental abilities, to severe, with prolonged and debilitating cognitive dysfunction (Kane et al., 2011). Cognitive difficulties along with other neurological deficits including: anxiety, aggressiveness, and depression result in a significantly reduced quality of life (Masel and DeWitt, 2010). With military operations concluded in Iraq and continuing in Afghanistan TBI has become the major combat injury representing 28% of all combat casualties (Okie, 2005; U.S. Medicine, May 2006, Vol 42). Total estimates of military service members suffering TBIs between 2001 and 2010 range from 180,000 to 320,000 (U.S. Defense and Veterans Brain Injury Center).

Underlying TBI is physical injury to the brain resulting in decreased synaptic connectivity among neurons, loss and death of neurons, damage to cerebral blood vessels resulting in ischemic/hypoxic-induced damage, and secondary glial scaring. This loss of neurons and diminished synaptic connectivity is particularly apparent in the hippocampus (Gao et al., 2011; Zhang et al., 2011a; Zhang et al., 2011b) resulting in defective long-term potentiation (Schwarzbach et al., 2006) and cognitive deficits (e.g. Dikmen et al., 2009; Patel et al., 2010). The prevalence of TBI associated injuries that result in neuronal loss and decreased synaptic connectivity denote the need for therapies which support neuronal repair and/or replacement. These clinical endpoints advocate for the therapeutic use of neurotrophic factors which mediate neural development, neurogenesis, neuroprotection, and synaptogenesis, for treating TBI. Not unexpectedly neurotrophic factors have been considered as treatment options for TBI (Kaplan et al., 2010; Richardson et al., 2010; Qi et al., 2011). One particularly attractive but mostly overlooked neurotrophic factor is HGF, which has a proven ability to both stimulate neurogenesis (Shang et al., 2011; Wang et al., 2011) and synaptogenesis (see preliminary studies below). The fact that HGF application might represent a viable treatment option for TBI stems from the recent realization that HGF is a potent neurotrophic factor in many brain regions (Kato et al., 2009; Ebens et al, 1997), while affecting a variety of neuronal cell types (Yamamoto et al., 1997; Hayashi et al., 2006; Elsen et al., 2009).

HGF and Wound Healing:

Excessive scarring is typified by unnecessary accumulation of ECM components in the wound, due to an inappropriate balance between synthesis and degradation. Therapy for pathologic scarring may be directed at inhibiting the synthesis and promoting the degradation of the ECM. HGF in the skin promotes wound healing effectively in several ways: motivating the proliferation and motility of dermal vascular endothelial cells; stimulating the motility of epidermal keratinocytes; enhancing local blood supply; and accelerating the re-epithelialization of the wound (Nakanishi et al., 2002). Re-epithelialization inhibits the formation of scars. Studies have shown that HGF gene transfer accelerates denial wound healing by stimulating angiogenesis and reepithelialization (Nakanishi et al., 2002). Therapeutic approaches that augment HGF/SF would be expected to promote wound healing and prevent scar formation.

HGF as a Treatment Option for Metabolic Syndrome and Diabetes:

Several recent studies have implicated the critical role of the HGF/c-Met system in the regulation of glucose handling, insulin secretion, and tissue insulin sensitivity. Together these investigations have highlighted the therapeutic potential of augmenting the HGF/c-Met system for the treatment of type 2 diabetes and metabolic syndrome (Fafalios et al., 2011; Flaquer et al., 2012)). These investigators have shown that: 1) c-Met, the HGF receptor complexes with the insulin receptor; 2) c-Met is critically involved with hepatic glucose homoestasis; 3) HGF restores insulin responsiveness in a murine diabetic mouse model; 4) that HGF gene therapy can prevent the renal damage that typically accompanies diabetes, and 5) HGF ameliorates the vascular complication of diabetes (Peng et al., 2011).

The HGF/c-Met Signaling Pathway Potentiating Angiogenesis:

Angiogenesis is defined as the formation of new blood vessels from existing vascular bed, It is a prime requirement in physiological processes such as wound healing and the menstrual cycle, on the other hand, it is an essential step for multiple pathological conditions, like cancer, macular degeneration, atherosclerosis, diabetic retinopathy, neovascular glaucoma, psoriasis and rheumatoid arthritis. Consequently, the modulation of angiogenesis, whether it was through encouraging therapeutic angiogenesis or by stopping pathologic angiogenesis, is an exhilarating prospect for modern medicine. The equilibrium between physiological and pathological angiogenesis is mediated by the communication of numerous endogenous angiogenic and anti-angiogenic modulators.

Numerous studies have shown HGF to be a powerful inducer of neovasculature formation. Moreover HGF/c-Met inhibitors are clinically relevant anti-angiogenic agents. (Gherardi et al, 2012). This is probably attained through multiple pathways, achieved either by direct or indirect action on endothelial cells.

HGF as Anti-Fibrotic Agent:

Fibrotic disease takes many forms and is a major contributor to degraded function in the heart, kidney, and liver secondary to many pathological states including myocardial infarction, diabetes, and alcoholism. Hepatocyte growth factor (HGF) is showing a strong anti-fibrotic effect with remarkable effectiveness in ameliorating tissue fibrosis in a wide range of animal models HGF exhibits a remarkably powerful anti-fibrotic effect that ameliorates tissue fibrosis in a wide range of animal models and tissues (Liu and Yang, 2006). Evidence has documented the therapeutic effect of exogenous HGF in chronic allograft nephropathic rats, a model of chronic inflammation and progressive tissue scarring. The intramuscular administration of the human HGF gene reduced the rate of mortality, restrained inflammation and infiltration, and reduced renal fibrosis (Liu and Yang, 2006).

Coronary artery disease (CAD) ischemic events and myocardial infarction are the major causes of cardiac failure in the Western world. The only option for severe coronary blockage and atherosclerosis is bypass surgery. Two pathological events in CAD play major roles in the loss of cardiac function observed in CAD: 1) blockage of the coronary arteries resulting in decreased blood perfusion to the heart; and 2) the formation of fibrotic tissue after cardiac insult resulting in ventricle remodeling and decreased compliance. Increased levels of HGF in the circulation have been reported after acute myocardial Infarction (Zhu et al., 2000; Jin et al., 2003). This increase in circulating HGF can be used as biological marker for heart injury and gives a clue regarding its protective role (Ueda et al., 2001). Pharmaceuticals that enhance the HGF/Met signaling could potentially be used in the treatment of myocardial infarction, providing protection against oxidative stress and cell death due to apoptosis as well as reducing the foiniation of fibrotic tissue (Ahmet et al., 2002; Kondo et al., 2004; Pietronave et al., 2010). Moreover, another beneficial effect of HGF following myocardial infarction could lie in its ability to induce neovascularization, which could support formation of new cardiac vasculature that would improve reperfusion of the myocardium.

Although HGF is known to protect the liver against external insults, HGF generation has also been associated with several liver and extra-hepatic diseases. Experimental and clinical evidence indicates that HGF plays a crucial role in liver regeneration. Liver cirrhosis is the irreversible end result of fibrous scarring and hepatocellular regeneration and is a major cause of morbidity and mortality worldwide with no effective therapy. Although there is no specific etiology for this disease, cirrhosis has been defined as a chronic disease of the liver in which dispersed damage and regeneration of hepatic parenchymal cells have taken place and in which dissemination of connective tissue has resulted in inadequate organization of the lobular and vascular structures (Fujimoto and Kaneda, 1999; Kaibori et al., 2002). Ideally, approaches for the treatment of liver cirrhosis should include attenuation of fibrogenesis, encouragement of hepatocyte mitosis, and reformation of tissue architecture.

Studies have shown that exogenous administration of recombinant HGF increases the potential for liver regeneration after hepatoctomy especially in the cases of cirrhotic liver (Boros and Miller, 1995; Kaibori et al., 2002; Borowiak et al., 2004). Conversely, studies have shown that the clofibrate-related compounds, which increase HGF/SF levels, can induce hepatomegaly, proliferation of hepatic peroxisomes, and hepatic carcinoma (Xu and Wu, 1999). The linkage of HGF/SF both positively and negatively to hepatic diseases has made HGF-related therapeutics a hot area for pharmaceutical development.

Limitations to the Direct Use of HGF:

The direct use of HGF or any other protein neurotrophic factor as a therapeutic agent has two serious limitations: 1) large size and hydrophilic character precluding blood-brain barrier permeability (BBB); and 2) the need to be manufactured by recombinant methods at high cost, thus limiting its widespread use. These impediments can be overcome using one or more of an extensive library of small molecule HGF mimetics which are described herein, some of which are orally active, display profound pro-cognitive/anti-dementia/neuroprotective activity, and are inexpensive to synthesize.

Antagonists:

Improper activation of the c-Met receptor can be encouraged by genetic activating mutations, transcriptional upregulation or by ligand-dependent autocrine or paracrine mechanisms.

c-Met Activation in Cancer:

Cancer is a heterogeneous group of diseases that result from the accumulation of genetic mutations. These mutations cause altered function in proto-oncogenes leading to dysregulation of DNA repair, proliferation, and apoptotic signaling (Tannock, 2005). The dysregulation in the signals within a group of cells leads to the uncontrolled growth, and invasion that either directly intrudes upon and destroys adjacent tissue or metastasizes and spread to other location in the body through the lymphatic system or the blood stream.

A dysfunctioning Met and HGF system appears to be a critical trait of numerous human malignancies. Ectopical overexpression of HGF and/or c-Met in mouse and human cell lines leads them to develop tumorigenic and metastatic phenotypes in athymic nude mice (Rong et al., 1994). A large number of studies have shown that the HGF/c-Met pathway is one of the most dysregulated pathways in human malignancies, which include, but are not limited to: bladder, breast, cervical, colorectal, endometrial, esophageal, gastric, head and neck, kidney, liver, lung, nasopharyngeal, ovarian, pancreatic, prostate, and thyroid cancers (http://www.vai.org/met/). Lastly, an activating mutations of c-Met has been discovered in sporadic and inherited forms of human renal papillary carcinomas (Danilkovitch-Miagkova and Zbar, 2002). These mutations which alter sequences within the kinase domain have also been found in other types of solid tumors and metastatic lesions. At this point it's worth mentioning that HGF over- or miss-expression often correlates with poor prognosis and that the down-regulation of c-Met or HGF expression in human tumor cells reduced their tumorigenicity (Abounader et al., 2002).

Activation of Met in cancer occurs most often through ligand autocrine or paracrine activation. Osteosarcomas and globlastoma mutliforme, which express both c-Met and HGF are examples of dysfunctional autocrine control. In other instances where paracrine control is paramount, c-Met over-expression has been reported in human primary tumors while HGF is provided by stromal cells and not the tumor itself (Houldsworth et al., 1990; Kuniyasu et al., 1992; Hara et al., 1998; Tong et al., 2004; Miller et al., 2006; Bean et al., 2007).

The list of neoplasms in which c-Met overexpression has been detected is growing relentlessly. In the case of carcinomas, excessive levels of c-Met expression have been found in virtually every malignancy (Danilkovitch-Miagkova and Zbar, 2002). Receptor over-expression can lead to local receptor oligomerization generating cells reactive to sub-threshold ligand concentrations. HGF itself is able to trigger the transcription of c-Met (Boccaccio et al., 1994), and it is thus HGF, which is universally expressed by stromal cells throughout the body that typically drives tumor over expression of c-Met (Aguirre Ghiso et al., 1999; Parr et al., 2004). This uniqueness of HGF permits it to play a critical role, which engages paracrine positive feedback loops that prop up the growth and metastasis of cancer cells. Interestingly, this notion is in agreement with the observation that c-Met activating mutations require HGF to enhance their catalytic effectiveness (Michieli et al., 1999). HGF can also abnormally stimulate c-Met in an autocrine manner, as depicted in gliobastomas (Weidner et al., 1990), breast carcinomas (Potempa and Ridley, 1998), rhabdomyosarcomas (Hartmann et al., 1994) and osteosarcomas (Ridley et al., 1995). With multiple mechanisms of activation, it is clear that both Met and HGF are major contributors to the progression of most human cancers. Additionally, the demonstrated activities of c-Met and HGF in proliferation, invasion, angiogenesis and anti-apoptosis (Weidner et al., 1990; Rong et al., 1994; Kitamura et al., 2000; Xiao et al., 2001; Wang et al., 2002; Derksen et al., 2003) demarcate the different stages at which these molecules can participate in tumor development.

Although, c-Met is used as a general marker for cancer, is also an indicator of biological significance with respect to malignancy and patient prognosis, with high levels correlated with a poor prognosis. Molecules that inhibit c-Met and HGF can therefore be expected to interfere with the molecular causes of many cancers, and should significantly help in attenuating Recent studies from the Harding lab have confirmed the potential use of HGF antagonists as effective anti-cancer/anti-angiogenic agents (Yamamoto et al., 2010, Kawas et al., 2011; Kawas et al., 2012).

Macular Degeneration/Diabetic Retinopathy:

Age-related macular degeneration (ARMD) is the most common cause of irreversible vision loss in Americans over the age of 60. It is predicted that 10 million Americans will suffer from some level of this age-related visual damage during their retirement years. In normal healthy eyes, retinal pigment epithelial (RPE) cells form a polarized monolayer adjacent to the photoreceptors and are involved in various activities that are essential to retinal homeostasis and visual function. In the case of macular degeneration, unfortunately, adhesions and communication between RPE cells are lost because of inflammation. When inflammation occurs, RPE cells secrete many growth factors including HGF/SF, which stimulates the division and migration of RPE and the formation of new vasculature from existing blood vessels (angiogenesis). HGF also stimulates the production of other growth factors (e.g. VEGF), which further promote the formation of new blood vessels that invade neighboring matrix (Jun et al., 2007). Hence the use of HGF blockers could be used either prophylactically, or as a treatment to slow down the progression of the disease and subsequent loss of vision.

Proliferative diabetic retinopathy (PDR), which entails a distinctive neovascularization of the retina that is characterized by the invasion of vessels into the vitreous cavity, is coupled with bleeding and scarring around the proliferative channel (Katsura et al., 1998). There is substantial evidence that multiple growth factors are involved in the onset and progression of the neovascularization process in general and in the PDR in specifically. These include basic fibroblast growth factor (bFGF), Insulin-like growth factors (IGF-I), vascular endothelial growth factor (VEGF), and HGF. Of these, HGF has the most pronounced effects on endothelial growth and mitogenic activity (Boulton, 1999). Studies have found that levels of HGF in the vitreous fluid of PDR patients are considerably higher than in non-diabetic patients, and that the levels of HGF are especially high in the active stage of PDR (Katsura et al., 1998). This suggests that HGF stimulates or perpetuates neovascularization in PDR. Therefore, it is plausible to think that an HGF antagonist would be a promising option as a prophylactic treatment, or to ameliorate the progression of PDR.

BRIEF DESCRIPTION OF THE DRAWINGS

FIG. 3A-E. Time dependent effects of Nle$^1$-AngIV and Dihexa treated neurons on spinogenesis. Hippocampal neurons transfected with mRFP-β-actin were treated with $10^{-12}$ M Dihexa or Nle$^1$-Ang IV for 5 days in culture or for 30 minutes prior to fixation on day in vitro 12 (DIV 12), promote spinogenesis. A) Representative image of the dendritic arbor of a 5 day vehicle treated hippocampal neuron. B) Representative image of a dendritic arbor from a neuron stimulated for 5 days with $10^{-12}$ M Dihexa. C) Representative image of the dendritic arbor of a neuron stimulated with $10^{-12}$ M Nle$^1$-Ang IV for 5 days. D) Bar graph representing the number of spines per 50 μm dendrite length per treatment condition following a 5 day in vitro treatment. * $P<0.001$; n=200. E) Bar graph representing the number of spines per 50 μm dendrite length per treatment condition following an acute 30 minute treatment. * $P<0.001$; n=60. *Data obtained from separate cultures; cultures were 12 days old at time of fixing. Mean±S.E.M. by one-way ANOVA and Tukey post hoc test.

─▲─ Norleual and ─■─ -D-Nle-Tyr-Ile-NH—$(CH_2)_5$—$CONH_2$ were incubated in heparinized rat blood at 37° C.; the figure shows percent recovery over time (mean±SD). The calculated stability $t_{1/2}$ based on single phase exponential decay for Norleual was 4.6 min and for D-Nle-Tyr-Ile-NH—$(CH_2)_5$—$CONH_2$ stability $t_{1/2}$ was 79.97 min.

Figure 23:
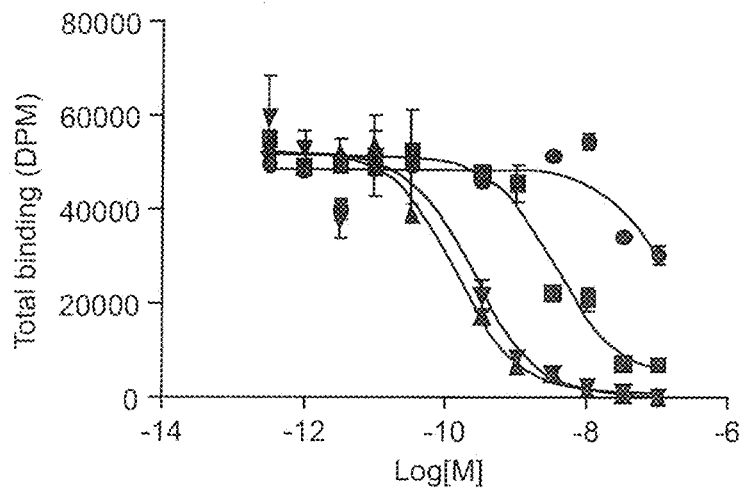

FIG. 23. Binding of D-Nle-X-Ile-NH—$(CH_2)_5$—$CONH_2$ analogs to HGF. Representative curves illustrating the competition of D-Nle-X-Ile-NH—$(CH_2)_5$—$CONH_2$ analogs for $^3$H-Hinge binding to HGF. The D-Nle-X-Ile-NH—$(CH_2)_5$—$CONH_2$ analogs and $^3$H-Hinge ($13.3 \times 10^{-12}$M) were incubated with 1.25 ng of HGF for 40 min at 37° C. in 0.25 ml of buffer. HGF-bound Hinge was eluted from Bio-Gel P6 columns after the addition of different concentrations of the D-Nle-X-Ile-NH—$(CH_2)_5$—$CONH_2$ analogs ($10^{-13}$-$10^{-7}$M). The radioactivity of the eluted solutions was quantitated using scintillation counting. These data demonstrate that the D-Nle-X-Ile-NH—$(CH_2)_5$—$CONH_2$ analogs exhibit a range of affinities for HGF. The $K_i$s for the Met, Trp, Cys, and Tyr analogs were respectively determined to be: $1.375 \times 10^{-07}$M, $3.372 \times 10^{-09}$M, $1.330 \times 10^{-10}$ M, and $2.426 \times 10^{-10}$ M; N=9.

─▲─ D-Nle-Cys-Ile-NH—$(CH_2)_5$—$CONH_2$,
─●─ D-Nle-Met-Ile-NH—$(CH_2)_5$—$CONH_2$,
─■─ D-Nle-Trp-Ile-NH—$(CH_2)_5$—$CONH_2$,
─▼─ D-Nle-Tyr-Ile-NH—$(CH_2)_5$—$CONH_2$.

Figure 24A:
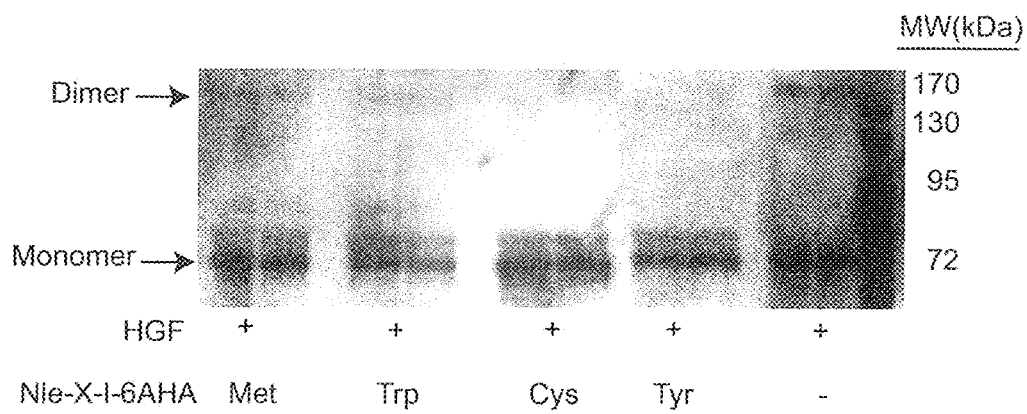

FIGS. 24A and B. Inhibition of HGF dimerization by D-Nle-X-Ile-NH—$(CH_2)_5$—$CONH_2$ analogs. HGF spontaneously dimerizes when incubated in PBS in the presence of heparin. HGF was incubated without (control) or with various drug candidates at $10^{-10}$ M. These include the derivatives of D-Nle-X-Ile-(6) amino-hexanoic amide, an AngIV-based analog family, where X=Tyr, Cys, Tip, and Met. After 30 minute incubation, samples were cross-linked with BS3, separated by gel electrophoresis, and silver stained. Band density was quantified and used to determine the level of HGF dimerization in each group. Treatment groups (Tyr, Cys, Trp) were statistically different than the HGF treated group (P<0.05; N=8) (A) Representative gel. (B) Pooled and quantified data.

Figure 25:
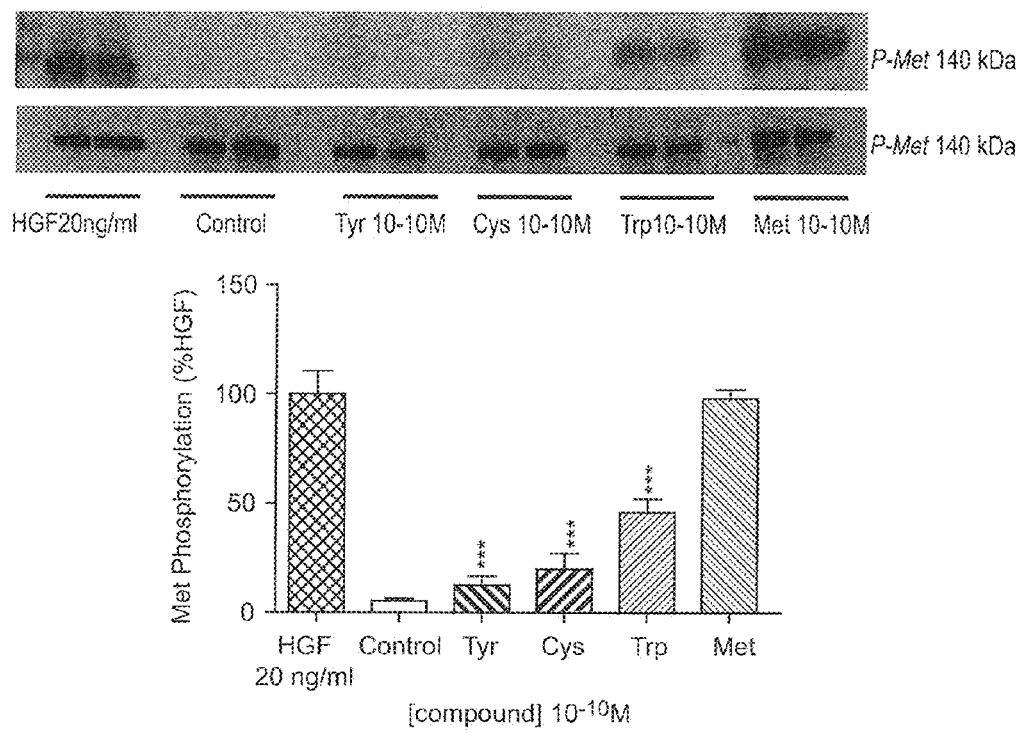

FIG. 25. Inhibition of Met phosphorylation by D-Nle-X-Ile-NH—$(CH_2)_5$—$CONH_2$ analogs. HEK293 cells were treated for 10 min with HGF+/−amino-hexanoic amide analogs at the indicated concentrations. HEK293 cell lysates were immunoblotted with anti-phospho-Met and anti-Met antibodies. The differences in the mean values for Met phosphorylation among the indicated treatment groups (Nle-X-Ile-(6) amino-hexanoic amide analogs) compared to the HGF treated group were greater than would be expected by chance (P<0.05; N=6). The Met group was not different than the HGF group (P>0.05; N=6).

Figure 26:
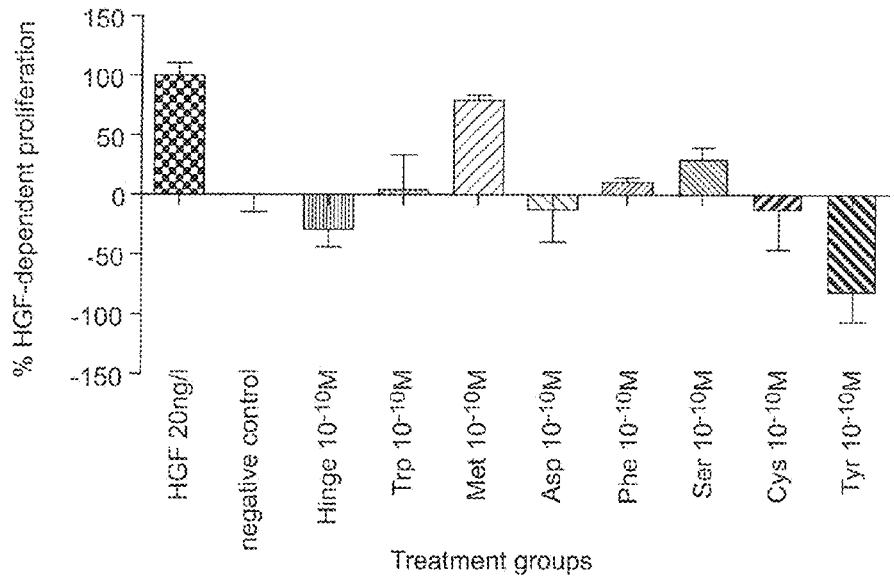

FIG. 26. Effects of D-Nle-X-Ile-NH—$(CH_2)_5$—$CONH_2$ analogs on MDCK cell proliferation. MDCK cells were treated with a PBS vehicle (negative control), HGF, or HGF in combination with Nle-X-Ile-(6)-amino-hexanoic amide analogs (X=L-amino acid) at $10^{-10}$M concentration. The Hinge peptide (KDYIRN), which represents the dimerization domain of HGF, was included as a positive control. The cells were allowed to grow for 4 days. Cell numbers were estimated on the fourth day with an MTT assay by measuring absorbance at 590. HGF-dependent proliferation: control values were subtracted from all values to determine HGF-induced increase in cell proliferation. N=6. * p<0.001.  p<0.001, * p<0.05, ns: not significant.

Figure 27A:
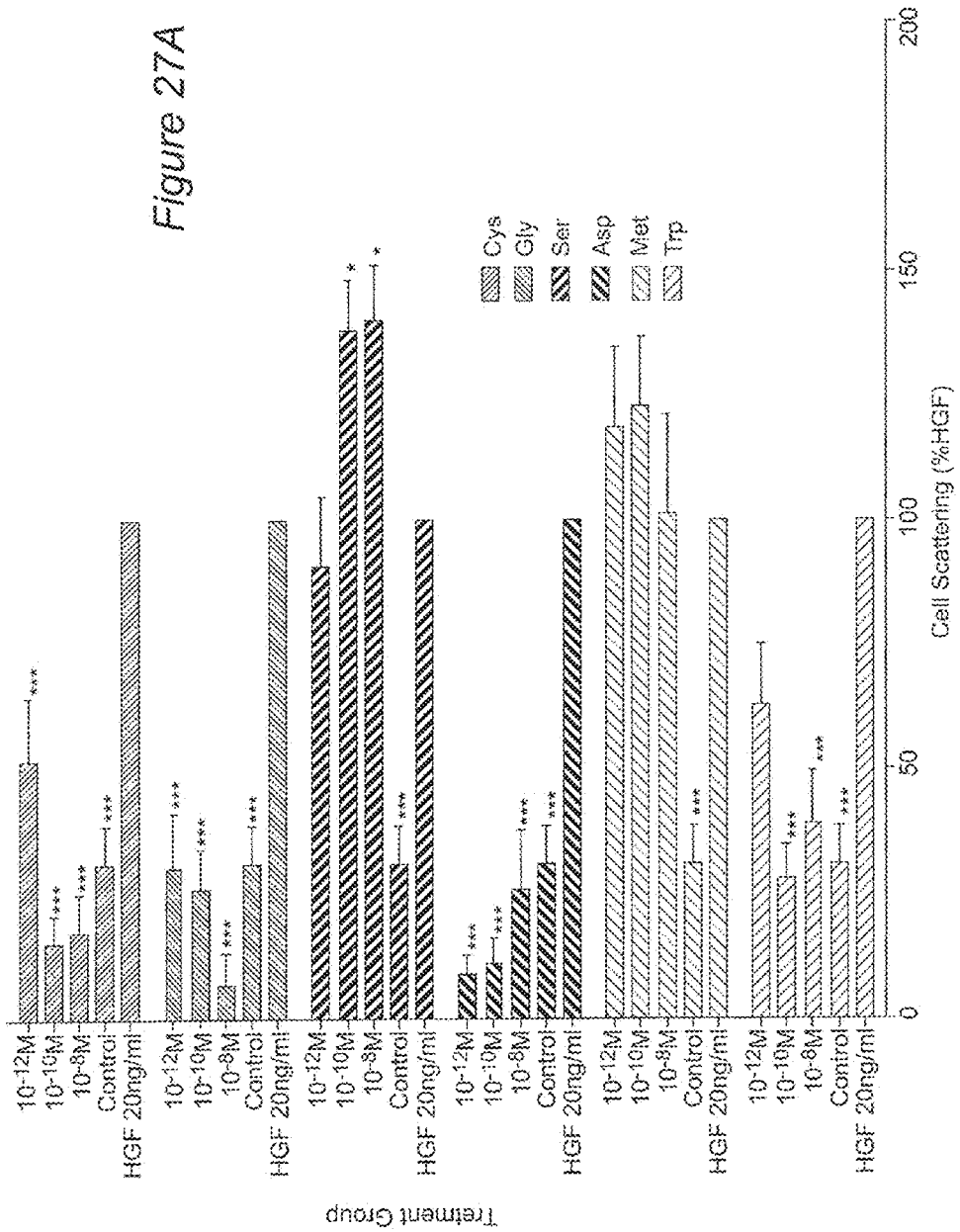
Figure 27B:
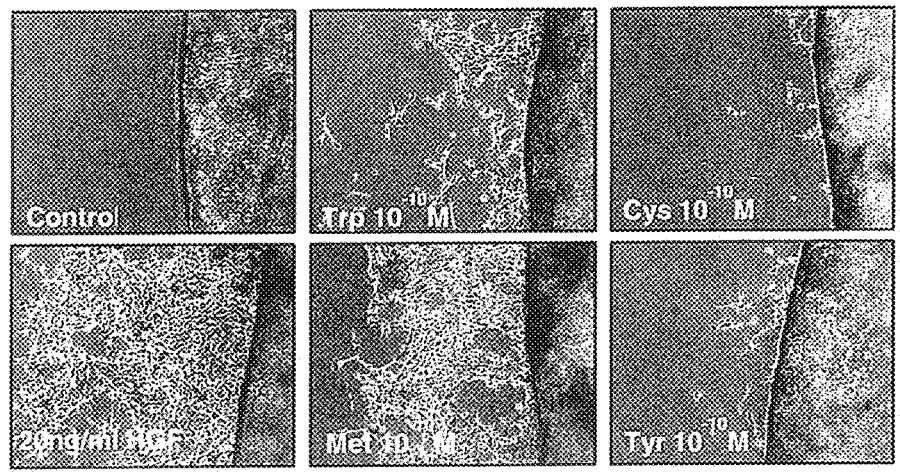

FIGS. 27 A and B. Effect of D-Nle-X-Ile-NH—$(CH_2)_5$—$CONH_2$ analogs on HGF-dependent scattering in MDCK cells. Cell scattering in which cells lose the cell-to-cell contacts and then migrate rapidly is the classic response to HGF. MDCK cells, the gold standard cellular model for studying the HGF/Met system, were grown to 100% confluence on cover slips and then placed in a clean plate. The cells were stimulated to scatter off of the cover slip by adding 20 ng/ml of HGF to the media alone or in combination with Nle-X-Ile-(6) amino-hexanoic amide analogs (X=L-amino acid). After 48 h of scattering, the cells were fixed with methanol and stained with Diff-Quik. The coverslips were removed to reveal the ring of cells that had scattered off of the cover slip and onto the plate. (A) The effect of HGF on scattering was quantitated by determining by densitometry of the digital images from scattered cells. ANOVA analysis indicates that the Tyr+HGF, Cys+HGF, and Trp+HGF treated groups were different from the HGF alone group but not different from the control group. The HGF and HGF+Met groups were not different. N=8, p<0.05 (B) Representative pictures of MDCK cells scattering off the coverslips.

Figure 28:
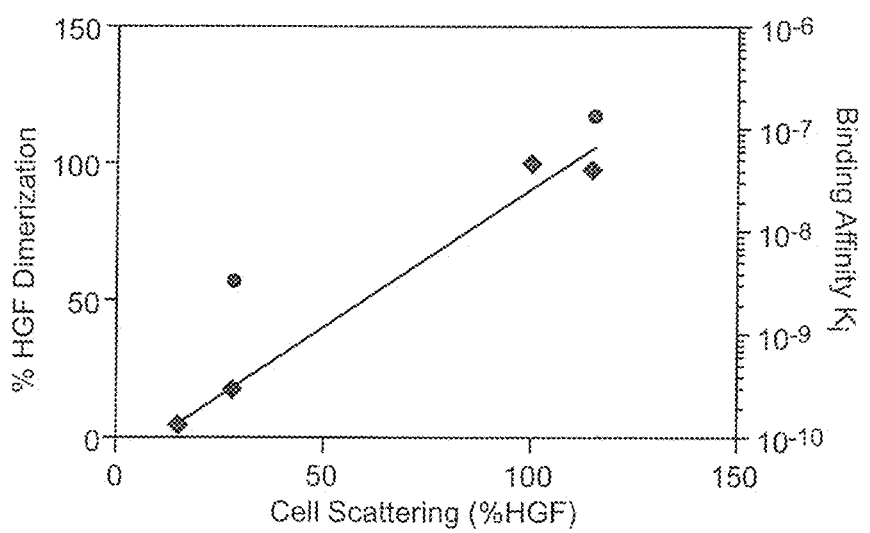

FIG. 28. Correlation between inhibition of MDCK cell scattering and interference with dimerization and the affinity to bind HGF. Three derivatives of the D-Nle-X-Ile-(6)amino-hexanoic amide, where X is: Cys, Trp, or Met were examined to determine whether the percent of inhibition of dimerization and the binding affinity for each compound for HGF could be correlated to in vitro cellular activity, namely inhibition of MDCK cell scattering. The figure shows a strong correlation between percent inhibition of HGF dimerization (♦; $R^2$=0.9809) and for binding affinity to HGF (●; $K_i$ Values; $R^2$=0.9903) and percent inhibition of HGF-dependent cell scattering.

FIGS. 29 A and B. Inhibition of B16-F10 melanoma lung colonization by D-Nle-Cys-Ile-NH—$(CH_2)_5$—$CONH_2$. 400, 000 B16-F10 murine melanoma cells were injected into the tail vein of C57BL/6 mice. Mice received daily IP injections of D-Nle-Cys-Ile-(6)-amino-hexanoic amide (10 µg/kg/day or 100 µg/kg/day) or PBS vehicle. (A) After 14 days, the lungs from D-Nle-Cys-Ile-(6)-amino-hexanoic amide treated mice exhibited an obvious reduction in melanoma colonies when compared to untreated controls. (B) After removal, lungs were homogenized and total melanin content was determined spectrophotometrically and used to quantify total pulmonary melanoma colonization in vehicle treated and D-Nle-Cys-Ile-(6)-amino-hexanoic amide treated. Ungrafted age-matched control lungs exhibited a background absorbance at 410 nm. N=15, Mean±SEM; * P<0.05, *** P<0.001.

DETAILED DESCRIPTION

Peptide analogs or mimics of HGF (also referred to as "growth factor mimics" or "analogs") having a variety of therapeutic utilities have the following general structural formula:

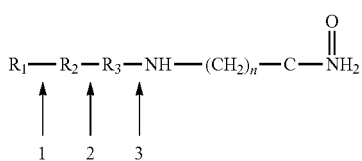

where

R₁ is an N-acyl group such as, for example, hexanoyl, heptanoyl, pentanoyl, butanoyl, propanoyl, acetanoyl, or benzoyl,
   a substituted or unsubstituted phenyl,
   a D or L norleucine,
   an amino acid (D or L) such as, for example, lysine, arginine, norvaline, ornithine, or S-benzyl cysteine amino acid residues;

R₂ is an amino acid (D or L), such as, for example, tyrosine, cysteine, phenyalanine, aspartic acid, glutamic acid, glycine, tryptophan, lysine, homocysteine, homoserine, homophenylalanine;

R₃ is a D or L isoleucine, leucine or valine amino acid residue; and n ranges from 3-6;

and wherein covalent bonds 1, 2 and 3 are either peptide bonds (e.g. —CO—NH— or reduced peptide bonds (CH₂—NH₂).

An exemplary peptide bond and reduced peptide bond are depicted below:

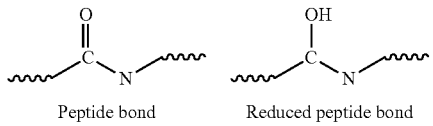

Peptide bond      Reduced peptide bond

Compounds within the general structural formula have been synthesized and analyzed according to the following procedures.

Standard Synthesis Method:

All compounds were synthesized by solid phase methods using an AAPPTEC Endeavor 90 peptide synthesizer using Fmoc protected amino acids. All peptide amides were synthesized on a Rink resin. The resin was pre-swollen in dimethylformamide (DMF) and deprotected with 20% piperidine/DMF for 30 minutes. The piperidine/DMF was then removed by filtration. After deprotection, the N-α Fmoc protected amino acid was added to reaction vessel as a dry powder (3 equivalents). The vessel was then filled with ⅔ full with DMF and dry diisopropylethylamine (DIPEA; 3.5-4 equivalents) was added. Next N-[(1H-benzotriazol-1-yl)(dimethylamino)methylene]-N-methyl-methanaminium hexafluorophosphate N-oxide (HBTU; 2.9 equivalents) was added and the suspension mixed for 30 minutes. The solution was then removed by filtration. The resin was then washed twice with DMF, twice with methanol, twice with dichloromethane, and finally twice more with DMF. Solutions were removed by filtration after each wash. Coupling efficiency was monitored using a Kaiser test for free amines. If the test was positive the amino acid was re-coupled to the resin or growing peptide chain. If the test indicated a good linkage, the resin was washed once more with DMF, deprotected with 20% piperidine/DMF for 30 minutes as indicated above, and again washed with DMF. The coupling then proceeded as indicated above.

Acylation of the N-Terminal of the Peptide:

After final deprotection, the peptide resin is incubated with 20% of the appropriate acyl anhydride in DMF and DIPEA (1.5 equivalents) for 30 minutes at room temperature. The resin was now washed twice with DMF, twice with methanol, twice with dichloromethane, and finally twice more with DMF. The solution was removed by filtration and a Kaiser test was performed to verify the completeness of the capping. If free amine was detected the capping procedure was repeated.

Insertion of an N-Terminal Reduced Peptide Bond:

After deprotection, hexanal (3 equivalents) DMF was added to the resin and allowed to mix for 5 minutes. Next, 3 equivalents of sodium cyanoborohydride were added and the suspension was mixed for an additional 2 hours. After the standard washing procedure was performed (see above), the Kaiser test was again used to verify the completeness of the reaction. If coupling was deemed incomplete, the procedure was repeated.

Cleavage of Peptide from Rink Resin:

After the last amino acid was deprotected and washed the resin was transferred to a sintered glass funnel (4 porosity) and the DMF removed by vacuum. The semi-dry resin was then suspended in 20% trifluoroacetic acid (TFA) with 2.5% triisopropyl-silane as a scavenger, incubated at room temperature for 15 minutes, and filtered. The resin was washed three times with additional DMF and filtered. Ten volumes of ice-cold diethyl ether were added to the combined filtrates and the mixture allowed to set at 4° C. overnight. Precipitated peptide was recovered by filtration and washed three times with ice-cold ether. For very hydrophobic peptides the combined ether washes were re-extracted with DMF, allowed to precipitate peptide, and filtered to recover additional peptide.

Peptide Purification and Analysis:

Crude peptides were first purified by reverse phase HPLC using a C18 column using gradient elution. The typical gradient was 10% to 40% component B over 30 minutes at a flow rate of 1 ml/min at 37° C. where component A was 80 mM triethyamine phosphate, pH 3.0 and component B was acetonitrile (ACN). In all instances only a single peak with 215 nm absorption was detected and collected. The collected compound was lyophilized and redissolved in 20% methanol and injected onto a second C18 column. The HPLC/MS system used was from Shimadzu (Kyoto, Japan), consisting of a CBM-20A communications bus module, LC-20AD pumps, SIL-20AC auto sampler, SPD-M20A diode array detector and LCMS-2010EV mass spectrometer. Data collection and integration were achieved using Shimadzu LCMS solution software. The analytical column used was an Econosphere C18 (100 mm×2.1 mm) from Grace Davison Discovery Science (Deerfield, Ill., USA). The mobile phase consisted of HPLC grade methanol and water with 0.1% trifluoroacetic acid. Separation was carried out using a non-isocratic method (20%-50% methanol over 30 min) at 37° C. and a flow rate of 0.3 mL/min. For MS analysis, a positive ion mode (Scan) was used and peaks analyzed at the anticipated m/z. Typical peak purity analysis revealed a peak purity index of >0.95. Wavelength ratioing with the diode array detector further confirmed peak purity.

Table 1 below presents a listing of compounds in Family 1, drawn to mimetics, and Families 2-5, drawn to antagonists, all of which have been synthesized and analyzed according to the procedures described above.

TABLE 1

General Structure of Family 1 (Mimetics) and Families 2-5 (Antagonists)

$$R_1\text{—}R_2\text{—}R_3\text{—}NH\text{—}(CH_2)_n\text{—}\overset{\overset{O}{\|}}{C}\text{—}NH_2$$

Arrows 1-3 denote positions 1, 2, 3

| Family # | $R_1$ (N-acyl group) | R2 | R3 | 1 |
|---|---|---|---|---|
| 1 | hexanoyl | Tyr | Ile | pb |
|  | heptanoyl | Tyr | Ile | pb |
|  | pentanoyl | Tyr | Ile | pb |
|  | butanoyl | Tyr | Ile | pb |
|  | propanoyl | Tyr | Ile | pb |
|  | acetanoyl | Tyr | Ile | pb |
|  | benzoyl | Tyr | Ile | pb |
|  | hexanoyl | Tyr | Ile | ψ |

| Family # | R1 | R2 | R3 |
|---|---|---|---|
| 2 | D-Nle | Tyr | Ile |
|  | D-Nle | Phe | Ile |
|  | D-Nle | Asp | Ile |
|  | D-Nle | Arg | Ile |
|  | D-Nle | Ile | Ile |
|  | D-Nle | Ser | Ile |
|  | D-Nle | His | Ile |
|  | D-Nle | Gly | Ile |
|  | D-Nle | Cys | Ile |
|  | D-Nle | Met | Ile |
|  | D-Nle | Trp | Ile |
|  | D-Nle | Lys | Ile |
|  | D-Nle | Val | Ile |
|  | D-Nle | Gly | D-Ile |
| 3 | D-Nle | D-Tyr | Ile |
|  | D-Nle | D-Phe | Ile |
|  | D-Nle | D-Asp | Ile |
|  | D-Nle | D-Arg | Ile |
|  | D-Nle | D-Ile | Ile |
|  | D-Nle | D-Ser | Ile |
|  | D-Nle | D-His | Ile |
|  | D-Nle | D-Gly | Ile |
|  | D-Nle | D-Cys | Ile |
|  | D-Nle | D-Met | Ile |
|  | D-Nle | D-Trp | Ile |
|  | D-Nle | D-Lys | Ile |
| 4 | Tyr | Tyr | Ile |
|  | Phe | Tyr | Ile |
|  | Asp | Tyr | Ile |
|  | Arg | Tyr | Ile |
|  | Ile | Tyr | Ile |
|  | Ser | Tyr | Ile |
|  | His | Tyr | Ile |
|  | Gly | Tyr | Ile |
|  | Cys | Tyr | Ile |
|  | Met | Tyr | Ile |
|  | Typ | Tyr | Ile |
|  | Lys | Tyr | Ile |
| 5 | D-Tyr | Tyr | Ile |
|  | D-Phe | Tyr | Ile |
|  | D-Asp | Tyr | Ile |
|  | D-Arg | Tyr | Ile |
|  | D-Ile | Tyr | Ile |
|  | D-Ser | Tyr | Ile |
|  | D-His | Tyr | Ile |
|  | D-Cys | Tyr | Ile |
|  | D-Met | Tyr | Ile |
|  | D-Typ | Tyr | Ile |
|  | D-Lys | Tyr | Ile |

Arrows 1-3 denote pb = peptide bond;
ψ = reduced peptide bond (CH$_2$—NH$_2$)
n = 5

With reference to Table 1, while a number of compounds which have been synthesized include tyrosine and isoleucine at $R_2$ and $R_3$, respectively, a wide range of amino acid and other residues might be used for the mimetics or agonists (Family 1 and Families 2-5, respectively) in the practice of embodiments of the invention at these other positions including, without limitation, tyrosine, cysteine, methionine, phenylalaine, aspartic acid, glutamic acid, histidine, tryptophan, lysine, leucine, valine, homocysteine, homoserine, and homophenylalanine. Further, while the mimetics include certain N-acyl groups as specified in Table 1 (Family 1), in the practice of various embodiments of the invention other N-acyl groups or substituted or unsubstituted phenyl groups may be used at $R_1$. In addition, while a number of the agonists in Table 1 (Families 2-5) have norleucine at $R_1$, or an amino acid residue, in the practice of various embodiments of this invention a number of an amino acid residues (D or L) may be used at residue $R_1$, including without limitation, tyrosine, phenylalanine, aspartic acid, arginine, isoleucine, serine, histidine, glycine, cysteine, methionine, tryptophan, norvaline, ornithine, S-benzyl cysteine amino acid residues. Finally, while all the compounds synthesized and tested in Table 1 included 5 methyl repeats, the methyl repeats (n) could range from 3-6 within the practice of the some of the embodiments of the present invention.

Compounds within Table 1 have also been assessed as follows:

Assessment of HGF Mimetic Activity:

HGF mimetic activity was typically assessed by one or both of two methods: augmentation of HGF-dependent c-Met phosphorylation in HEK293 cells, or 2) augmentation of HGF-dependent cell scattering in MDCK cells. All the compounds in Family one were tested using the c-Met phosphorylation assay. N-hexanoyl-Tyr-Ile-(6) aminohexamide was further evaluated and found to have spectacularly augment HGF-dependent MDCK cell scattering. Table 2 presents a summary of the results.

TABLE 2

| Compound ($10^{-12}$M) | HGF Mimetic Activity |
|---|---|
| N-heptanoyl-Tyr-Ile-(6) aminohexamide | ++++ |
| N-hexanoyl-Tyr-Ile-(6) aminohexamide | ++++ |
| N-pentanoyl-Tyr-Ile-(6) aminohexamide | ++++ |
| N-butanoyl-Tyr-Ile-(6) aminohexamide | +++ |
| N-propanoyl-Tyr-Ile-(6) aminohexamide | ++ |
| N-acetanoyl-Tyr-Ile-(6) aminohexamide | + |
| N-benzoyl-Tyr-Ile-(6) aminohexamide | + |
| N-hexanoyl-ψ (CH$_2$—NH$_2$)-Tyr-Ile-(6) aminohexamide | +++ |

Cell Culture.

Human embryonic kidney cells 293 (HEK293), Madin Darby canine kidney cells (MDCK), and B16F10 murine melanoma cells were grown in DMEM, 10% fetal bovine serum (FBS). Cells were grown to 90-100% confluency before use. For most but not all studies HEK and MDCK cells were serum starved for 24 hours prior to the initiation of drug treatment.

Western Blotting.

HEK293 cells were seeded in 6 well tissue culture plates and grown to 95% confluency in DMEM containing 10% FBS. The cells were serum deprived for 24 hours prior to the treatment to reduce the basal levels of phospho-Met. Following serum starvation, cocktails comprised of vehicle and HGF (2.5 ng/ml) with/without the test compound were prepared and pre-incubated for 30 minutes at room temperature. The cocktail was then added to the cells for 10 minutes to stimulate the Met receptor and downstream proteins. Cells were harvested using RIPA lysis buffer (Upstate) fortified with phosphatase inhibitor cocktails 1 and 2 (Sigma-Aldrich; St. Louis, Mo.). The lysate was clarified by centrifugation at 15,000 g for 15 minutes, protein concentrations were determined using the BCA total protein assay, and then appropriate volumes of the lysates were diluted with 2× reducing Laemmli buffer and heated for ten minutes at 95° C. Samples containing identical amounts of protein were resolved using SDS-PAGE (Criterion, BioRad Laboratories), transferred to nitrocellulose, and blocked in Tris-buffered saline (TBS) containing 5% milk for one hour at room temperature. The phospho-Met antibody was added to the blocking buffer at a final concentration of 1:1000 and incubated at 4° C. overnight with gentle agitation. The membranes were then washed several times with water and TBS (PBS, 0.05% Tween-20), a 1:5000 dilution of horseradish-peroxidase conjugated goat anti-rabbit antiserum was added, and the membranes further incubated for one hour at room temperature. Proteins were visualized using the Supersignal West Pico Chemiluminescent Substrate system (Pierce, Fenton, Mo.) and molecular weights determined by comparison to protein ladders (BenchMark, Invitrogen; and Kaleidoscope, BioRad). Images were digitized and analyzed using a UVP phospho-imager.

Scattering Assay.

MDCK cells were grown to 100% confluency on the coverslips in six-well plates and washed twice with PBS. The confluent coverslips were then aseptically transferred to new six well plates containing 900 µl serum free DMEM. Norleual, Hinge peptide, and/or HGF (2.5 ng/ml) were added to appropriate wells. Control wells received PBS vehicle. Plates were incubated at 37° C. with 5% $CO_2$ for 48 hours. Media was removed and cells were fixed with methanol. Cells were stained with Diff-Quik Wright-Giemsa (Dade-Behring, Newark, Del.) and digital images were taken. Coverslips were removed with forceps and more digital images were captured. Pixel quantification of images was achieved using Image J and statistics were performed using Prism 5 and InStat v.3.05.

For the general structural formula presented above, and reproduced below for ease of reference, there are several different compounds which can be prepared according to the synthesis procedures described above and used for therapies described below. Table 3 identifies various exemplary families with various listed compounds in those families (identified by substitution of moieties within the general formula).

TABLE 3

General Structure:

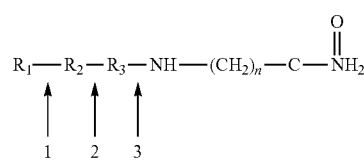

| Family # | $R_1$ | R2 | R3 | n | 1 | 2 | 3 |
|---|---|---|---|---|---|---|---|
| 1 | hexanoyl | Y | I | 5 | pb | pb | pb |
|  | heptanoyl | Y | I | 5 | pb | pb | pb |
|  | pentanoyl | Y | I | 5 | pb | pb | pb |
|  | butanoyl | Y | I | 5 | pb | pb | pb |
|  | propanoyl | Y | I | 5 | pb | pb | pb |
|  | acetanoyl | Y | I | 5 | pb | pb | pb |
|  | isopropanoyl | Y | I | 5 | pb | pb | pb |
|  | tert-butanoyl | Y | I | 5 | pb | pb | pb |
|  | isobutanoyl | Y | I | 5 | pb | pb | pb |
|  | benzoyl | Y | I | 5 | pb | pb | pb |

TABLE 3-continued

General Structure:

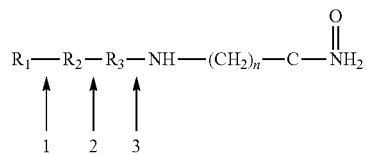

| | | | | | | | |
|---|---|---|---|---|---|---|---|
| 2 | hexanoyl | Y | I | 5 | ψ | pb | pb |
|  | heptanoyl | Y | I | 5 | ψ | pb | pb |
|  | pentanoyl | Y | I | 5 | ψ | pb | pb |
|  | butanoyl | Y | I | 5 | ψ | pb | pb |
|  | propanoyl | Y | I | 5 | ψ | pb | pb |
|  | acetanoyl | Y | I | 5 | ψ | pb | pb |
|  | isopropanoyl | Y | I | 5 | ψ | pb | pb |
|  | tert-butanoyl | Y | I | 5 | ψ | pb | pb |
|  | isobutanoyl | Y | I | 5 | ψ | pb | pb |
|  | benzoyl | Y | I | 5 | ψ | pb | pb |
| 3 | hexanoyl | Y | I | 5 | ψ | pb | ψ |
|  | heptanoyl | Y | I | 5 | ψ | pb | ψ |
|  | pentanoyl | Y | I | 5 | ψ | pb | ψ |
|  | butanoyl | Y | I | 5 | ψ | pb | ψ |
|  | propanoyl | Y | I | 5 | ψ | pb | ψ |
|  | acetanoyl | Y | I | 5 | ψ | pb | ψ |
|  | isopropanoyl | Y | I | 5 | ψ | pb | ψ |
|  | tert-butanoyl | Y | I | 5 | ψ | pb | ψ |
|  | isobutanoyl | Y | I | 5 | ψ | pb | ψ |
|  | benzoyl | Y | I | 5 | ψ | pb | ψ |
| 4 | hexanoyl | Y | I | 5 | pb | pb | ψ |
|  | heptanoyl | Y | I | 5 | pb | pb | ψ |
|  | pentanoyl | Y | I | 5 | pb | pb | ψ |
|  | butanoyl | Y | I | 5 | pb | pb | ψ |
|  | propanoyl | Y | I | 5 | pb | pb | ψ |
|  | acetanoyl | Y | I | 5 | pb | pb | ψ |
|  | isopropanoyl | Y | I | 5 | pb | pb | ψ |
|  | tert-butanoyl | Y | I | 5 | pb | pb | ψ |
|  | isobutanoyl | Y | I | 5 | pb | pb | ψ |
|  | benzoyl | Y | I | 5 | pb | pb | ψ |
| 5 | hexanoyl | F | I | 5 | pb | pb | pb |
|  | heptanoyl | F | I | 5 | pb | pb | pb |
|  | pentanoyl | F | I | 5 | pb | pb | pb |
|  | butanoyl | F | I | 5 | pb | pb | pb |
|  | propanoyl | F | I | 5 | pb | pb | pb |
|  | acetanoyl | F | I | 5 | pb | pb | pb |
|  | isopropanoyl | F | I | 5 | pb | pb | pb |
|  | tert-butanoyl | F | I | 5 | pb | pb | pb |
|  | isobutanoyl | F | I | 5 | pb | pb | pb |
|  | benzoyl | F | I | 5 | pb | pb | pb |
| 6 | hexanoyl | F | I | 5 | ψ | pb | pb |
|  | heptanoyl | F | I | 5 | ψ | pb | pb |
|  | pentanoyl | F | I | 5 | ψ | pb | pb |
|  | butanoyl | F | I | 5 | ψ | pb | pb |
|  | propanoyl | F | I | 5 | ψ | pb | pb |
|  | acetanoyl | F | I | 5 | ψ | pb | pb |
|  | isopropanoyl | F | I | 5 | ψ | pb | pb |
|  | tert-butanoyl | F | I | 5 | ψ | pb | pb |
|  | isobutanoyl | F | I | 5 | ψ | pb | pb |
|  | benzoyl | F | I | 5 | ψ | pb | pb |
| 7 | hexanoyl | F | I | 5 | ψ | pb | ψ |
|  | heptanoyl | F | I | 5 | ψ | pb | ψ |
|  | pentanoyl | F | I | 5 | ψ | pb | ψ |
|  | butanoyl | F | I | 5 | ψ | pb | ψ |
|  | propanoyl | F | I | 5 | ψ | pb | ψ |
|  | acetanoyl | F | I | 5 | ψ | pb | ψ |
|  | isopropanoyl | F | I | 5 | ψ | pb | ψ |
|  | tert-butanoyl | F | I | 5 | ψ | pb | ψ |
|  | isobutanoyl | F | I | 5 | ψ | pb | ψ |
|  | benzoyl | F | I | 5 | ψ | pb | ψ |
| 8 | hexanoyl | F | I | 5 | pb | pb | ψ |
|  | heptanoyl | F | I | 5 | pb | pb | ψ |
|  | pentanoyl | F | I | 5 | pb | pb | ψ |
|  | butanoyl | F | I | 5 | pb | pb | ψ |
|  | propanoyl | F | I | 5 | pb | pb | ψ |
|  | acetanoyl | F | I | 5 | pb | pb | ψ |
|  | isopropanoyl | F | I | 5 | pb | pb | ψ |
|  | tert-butanoyl | F | I | 5 | pb | pb | ψ |
|  | isobutanoyl | F | I | 5 | pb | pb | ψ |
|  | benzoyl | F | I | 5 | pb | pb | ψ |

TABLE 3-continued

General Structure:

$$R_1—R_2—R_3—NH—(CH_2)_n—C(=O)—NH_2$$

arrows 1, 2, 3 point to the three bonds

| | | R₁ | R₂ | R₃ | n | 1 | 2 | 3 |
|---|---|---|---|---|---|---|---|---|
| 9 | | hexanoyl | C | I | 5 | pb | pb | pb |
| | | heptanoyl | C | I | 5 | pb | pb | pb |
| | | pentanoyl | C | I | 5 | pb | pb | pb |
| | | butanoyl | C | I | 5 | pb | pb | pb |
| | | propanoyl | C | I | 5 | pb | pb | pb |
| | | acetanoyl | C | I | 5 | pb | pb | pb |
| | | isopropanoyl | C | I | 5 | pb | pb | pb |
| | | tert-butanoyl | C | I | 5 | pb | pb | pb |
| | | isobutanoyl | C | I | 5 | pb | pb | pb |
| | | benzoyl | C | I | 5 | pb | pb | pb |
| 10 | | hexanoyl | C | I | 5 | ψ | pb | pb |
| | | heptanoyl | C | I | 5 | ψ | pb | pb |
| | | pentanoyl | C | I | 5 | ψ | pb | pb |
| | | butanoyl | C | I | 5 | ψ | pb | pb |
| | | propanoyl | C | I | 5 | ψ | pb | pb |
| | | acetanoyl | C | I | 5 | ψ | pb | pb |
| | | isopropanoyl | C | I | 5 | ψ | pb | pb |
| | | tert-butanoyl | C | I | 5 | ψ | pb | pb |
| | | isobutanoyl | C | I | 5 | ψ | pb | pb |
| | | benzoyl | C | I | 5 | ψ | pb | pb |
| 11 | | hexanoyl | C | I | 5 | ψ | pb | ψ |
| | | heptanoyl | C | I | 5 | ψ | pb | ψ |
| | | pentanoyl | C | I | 5 | ψ | pb | ψ |
| | | butanoyl | C | I | 5 | ψ | pb | ψ |
| | | propanoyl | C | I | 5 | ψ | pb | ψ |
| | | acetanoyl | C | I | 5 | ψ | pb | ψ |
| | | isopropanoyl | C | I | 5 | ψ | pb | ψ |
| | | tert-butanoyl | C | I | 5 | ψ | pb | ψ |
| | | isobutanoyl | C | I | 5 | ψ | pb | ψ |
| | | benzoyl | C | I | 5 | ψ | pb | ψ |
| 12 | | hexanoyl | C | I | 5 | pb | pb | ψ |
| | | heptanoyl | C | I | 5 | pb | pb | ψ |
| | | pentanoyl | C | I | 5 | pb | pb | ψ |
| | | butanoyl | C | I | 5 | pb | pb | ψ |
| | | propanoyl | C | I | 5 | pb | pb | ψ |
| | | acetanoyl | C | I | 5 | pb | pb | ψ |
| | | isopropanoyl | C | I | 5 | pb | pb | ψ |
| | | tert-butanoyl | C | I | 5 | pb | pb | ψ |
| | | isobutanoyl | C | I | 5 | pb | pb | ψ |
| | | benzoyl | C | I | 5 | pb | pb | ψ |
| 13-16 | Same pattern as families 1-4 with R2 = S | | | | | | | |
| 17-20 | Same pattern as families 1-4 with R2 = T | | | | | | | |
| 21-24 | Same pattern as families 1-4 with R2 = D | | | | | | | |
| 25-28 | Same pattern as families 1-4 with R2 = E | | | | | | | |
| 29-32 | Same pattern as families 1-4 with R2 = Y, R3 = V | | | | | | | |
| 33-36 | Same pattern as families 1-4 with R2 = F, R3 = V | | | | | | | |
| 37-40 | Same pattern as families 1-4 with R2 = C, R3 = V | | | | | | | |
| 41-44 | Same pattern as families 1-4 with R2 = S, R3 = V | | | | | | | |
| 45-48 | Same pattern as families 1-4 with R2 = T, R3 = V | | | | | | | |
| 49-52 | Same pattern as families 1-4 with R2 = D, R3 = V | | | | | | | |
| 53-56 | Same pattern as families 1-4 with R2 = E, R3 = V | | | | | | | |
| 57-85 | Same pattern as families 29-56 with R3 = L | | | | | | | |
| 86-170 | Same pattern as families 1-85 with n = 3 | | | | | | | |
| 171-256 | Same pattern as families 1-85 with n = 4 | | | | | | | |
| 257-341 | Same pattern as families 1-85 with n = 6 | | | | | | | |

| | R₁ | R₂ | R₃ | n | 1 | 2 | 3 |
|---|---|---|---|---|---|---|---|
| 342 | D-norleucine | Y | I | 5 | pb | pb | pb |
| | D-norleucine | F | I | 5 | pb | pb | pb |
| | D-norleucine | C | I | 5 | pb | pb | pb |
| | D-norleucine | S | I | 5 | pb | pb | pb |
| | D-norleucine | T | I | 5 | pb | pb | pb |
| | D-norleucine | D | I | 5 | pb | pb | pb |
| | D-norleucine | E | I | 5 | pb | pb | pb |
| | D-norleucine | G | I | 5 | pb | pb | pb |
| 343 | D-norleucine | Y | I | 5 | pb | pb | ψ |
| | D-norleucine | F | I | 5 | pb | pb | ψ |
| | D-norleucine | C | I | 5 | pb | pb | ψ |
| | D-norleucine | S | I | 5 | pb | pb | ψ |
| | D-norleucine | T | I | 5 | pb | pb | ψ |
| | D-norleucine | D | I | 5 | pb | pb | ψ |
| | D-norleucine | E | I | 5 | pb | pb | ψ |
| | D-norleucine | G | I | 5 | pb | pb | ψ |
| 344 | D-norleucine | Y | I | 5 | ψ | pb | pb |
| | D-norleucine | F | I | 5 | ψ | pb | pb |
| | D-norleucine | C | I | 5 | ψ | pb | pb |
| | D-norleucine | S | I | 5 | ψ | pb | pb |
| | D-norleucine | T | I | 5 | ψ | pb | pb |
| | D-norleucine | D | I | 5 | ψ | pb | pb |
| | D-norleucine | E | I | 5 | ψ | pb | pb |
| | D-norleucine | G | I | 5 | ψ | pb | pb |
| 345 | D-norleucine | Y | I | 5 | ψ | pb | ψ |
| | D-norleucine | F | I | 5 | ψ | pb | ψ |
| | D-norleucine | C | I | 5 | ψ | pb | ψ |
| | D-norleucine | S | I | 5 | ψ | pb | ψ |
| | D-norleucine | T | I | 5 | ψ | pb | ψ |
| | D-norleucine | D | I | 5 | ψ | pb | ψ |
| | D-norleucine | E | I | 5 | ψ | pb | ψ |
| | D-norleucine | G | I | 5 | ψ | pb | ψ |
| 346-349 | Same pattern as families 342-345 with R3 = V | | | | | | |
| 350-353 | Same pattern as families 342-345 with R3 = L | | | | | | |
| 354-365 | Same pattern as families 342-353 with R1 = D norvaline | | | | | | |
| 366-377 | Same pattern as families 342-345 with R3 = D-lysine | | | | | | |
| 378-389 | Same pattern as families 342-345 with R3 = D-arginine | | | | | | |
| 390-401 | Same pattern as families 342-345 with R3 = D S-methyl cysteine | | | | | | |
| 402-457 | Same pattern as families 342-401 with n = 3 | | | | | | |
| 458-513 | Same pattern as families 342-401 with n = 4 | | | | | | |
| 514-569 | Same pattern as families 342-401 with n = 6 | | | | | | |

Arrows 1-3 may be pb = peptide bond;
ψ = reduced peptide bond (CH₂—NH₂)

Alternatively, the analogs or growth factor mimics of the present invention may also be represented as comprised of four elements joined by covalent peptide or reduced peptide bonds, as follows:

I-II-III-IV where

I=an acid such as heptanoic, hexanoic, pentanoic, butyric, proprionic, acetic, benzoic, or substituted benzoic acid, and isoforms thereof; or D or L norleucine, lysine, arginine, norvaline, ornithine, or S-benzyl cysteine II=a D or L cysteine, phenylalanine, aspartic acid, glutamic acid, serine, tyrosine, glycine, homocysteine, homoserine or homophenylalanine amino acid residue;

III=a D or L isoleucine, leucine, or valine amino acid residue; and

IV=amino-hexanoic, amino-pentanoic or amino butyric acid; wherein elements I, II, III and IV are joined by peptide or reduced peptide bonds.

In one embodiment, the analog is: hexanoic-tyrosine-isoleucine-(6)-amino-hexanoic amide. Using Formula I as a generic formula, for this particular analog, R1=hexanoyl; R2 is Tyr; R3 is Ile; and n=5. Alternatively, using the I-II-III-IV nomenclature, in this embodiment, I=hexanoic acid, II=Tyr; III=Ile; and IV=hexanoic amide.

Embodiments of the invention involve providing one or more HGF mimics to a subject in need thereof. Exemplary subjects or patients which might benefit from receiving therapy such as administration of the one or more HGF mimics described herein are generally mammals, and usually humans, although this need not always be the case, since veterinary and research related applications of the technology are also contemplated. Generally a suitable subject or patient in need of therapy are identified by, for example, a health care professional or professionals using known tests, measurements or criteria. For example, in the treatment for dementia, a subjects already having symptoms of dementia, or being at risk of developing symptoms of dementia will be identified. Similar identification processes will be followed for other diseases and/or disorders (e.g., cancer therapy, other cognitive dysfunction therapies, etc.). A suitable treatment protocol is then developed based on the patient, the disease and/or disorder and its stage of development, and the HGF mimic and its dosage and delivery format, as well as other relevant factors. The subject then receives treatment with HGF mimic. Embodiments of the invention also comprise one or more steps related to monitoring the effects or outcome of administration in order to evaluate the treatment protocol and/or to adjust the protocol as required or in a manner that is likely to provide more benefit, e.g. by increasing or decreasing doses of medication, or by changing the particular type of mimic that is administered, or by changing the frequency of dosing or the route of administration, etc. With particular reference to the embodiment of providing cognitive enhancement for example, while in some cases the improvement in cognition (or the prevention of loss of cognition) that occurs may be complete, e.g. the functioning of the patient returns to or remains normal (as assessed in comparison to suitable control subjects or standardized values obtained therefrom), this need not always be the case. Those of skill in the art will recognize that even a lower level of improvement in cognition may be highly beneficial to the patient, as may be the slowing of the progression of a disease, as opposed to a complete cure.

The methods of the invention involve administering compositions comprising the HGF mimics disclosed herein to a patient in need thereof. The present invention thus also provides compositions which comprise the HGF analogs/mimics as described herein, usually together with a pharmacologically suitable carrier or diluent. In some embodiments, one substantially purified HGF mimic is present in a composition; in other embodiments more than one HGF mimic is present, each HGF mimic being substantially purified prior to being mixed in the composition. The preparation of pharmacologically suitable compositions for use as medicaments is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of HGF mimic in the formulations may vary. However, in general, the amount in the formulations will be from about 1% to about 99%.

The HGF mimic compositions (preparations) of the present invention may be administered by any of the many suitable means which are well known to those of skill in the art, including but not limited to: by injection, inhalation, orally, intravaginally, intranasally, by ingestion of a food or product containing the mimic, topically, as eye drops, via sprays, etc. In preferred embodiments, the mode of administration is orally or by injection. In addition, the compositions may be administered in conjunction with other treatment modalities such as other agents which are used to treat, for example, dementia or the conditions which cause dementia in the patient, examples of which include but are not limited to the administration of anti-depressants and psychoactive drugs, administration of dopamine and similar agents. Similarly, in cancer treatment modalities, the HGF mimics may be administered together with analgesics and other suitable drugs. Thus, in embodiments of the invention, one or more HGF mimics may be used in combination with one or more different bioactive drugs.

The amount of HGF inhibitor that is administered may be in the range of from about 0.1 to about 1,000 mg/kg, an preferably in the range of from about 1 to about 100 mg/kg, although as one of skill in the art will recognize, the precise amount may vary depending on one or more attributes of the drug recipient, including but not limited to: weight, overall health, gender, age, nationality, genetic history, other conditions being treated, etc., and larger or smaller doses are within the practice of this invention. Dosing may also take place periodically over a period of time, and the dosage may change (increase or decrease) with time.

The HGF mimics of the invention may be used to treat a variety of cognitive function disorders (cognitive dysfunction) as well as other disorders that are related to HGF activity or lack thereof "Cognitive function" or "cognition" as used herein refers to a range of high-level brain functions, including but not limited to: the ability to learn and remember information; the ability to organize, plan, and problem-solve; the ability to focus, maintain, and shift attention as necessary; and to understand and use language; the ability to accurately perceive the environment; the ability to perform calculations. Such functions include but are not limited to memory (e.g. acquiring, retaining, and retrieving new information); attention and concentration (particularly divided attention); information processing (e.g. dealing with information gathered by the five senses); executive functions (e.g. planning and prioritizing); visuospatial functions (e.g. visual perception and constructional abilities); verbal fluency and speech (e.g. word-finding); general intellect (e.g. "intelligence"); long-term (remote) memory; conversational skills; reading comprehension; etc. Conversely, by "cognitive dysfunction" we mean the loss of such abilities. Losses may be measured, detected and/or diagnosed in any of the many ways known to those of ordinary skill in the art. Such methods include but are not limited to: the use of standardized testing administered by a professional (puzzles, word games or problems, etc.); by self-reporting and/or the reports of caretakers, friends and family members of an afflicted individual; by observation of the activities, life skills, habits and coping mechanisms of the individual by professional or lay persons; by the results of questionnaires administered to an afflicted individual; etc.

Such disorders may be caused, for example, by a decrease in synaptic connectivity and/or neuron density due to a variety of factors. In some embodiments, the loss is caused by a brain injury, e.g. traumatic brain injury. Traumatic brain injury, which is occurring at record levels as a result of wars and sporting activities, is characterized by reduced neuronal connectivity. Hence, the use of HGF mimetics represents a viable treatment option. Such brain injuries may be the result of an external trauma to the brain, e.g. caused by a high impact accident (e.g. a car accident, a fall, etc.), a shooting incident, a sports injury (e.g. caused by impact to the head such a boxers and football players experience); injuries received in combat, etc. Alternatively, such injuries may be the result of internal brain trauma, e.g. as the result of stroke, aneurism, surgical procedure, tumor, etc. or other types of conditions which result in lack of oxygen to the brain or to sections of the brain; injuries due to inhalation of toxic gases; due to aging of the brain; to diseases and disorders which exert a deleterious effect on the nervous system and/or brain, such as multiple sclerosis, Parkinson's disease, Huntington's disease, brain disorders such as schizophrenia, etc.

As a specific example of a therapy contemplated by embodiments of the invention, the HGF mimics may be used for the treatment of dementia. By "dementia" we mean a serious loss of cognitive ability in a previously unimpaired person, beyond what might be expected from normal aging. It may be static, the result of a unique global brain injury, or progressive, resulting in long-term decline due to damage or disease in the body. Although dementia is far more common in the geriatric population, it may occur in any stage of adulthood. For the purposes of embodiments of this invention, the term "dementia" may include and/or be caused by e.g. Alzheimer's disease, vascular dementia, dementia with Lewy bodies, etc. or combinations of these. In other embodiments of the invention, Alzheimer's disease may be excluded from this definition. Other causes of dementia which may be treated as described herein include but are not limited to hypothyroidism and normal pressure hydrocephalus. Inherited forms of the diseases which cause or are associated with dementia that may treated as described herein include but are not limited to: frontotemporal lobar degeneration, Huntington's disease, vascular dementia, dementia pugilistica, etc. In younger populations, progressive cognitive disturbance may be caused by psychiatric illness, alcohol or other drug abuse, or metabolic disturbances. Certain genetic disorders can cause true neurodegenerative dementia in younger populations (e.g. 45 and under). These include familial Alzheimer's disease, SCA17 (dominant inheritance); adrenoleukodystrophy (X-linked); Gaucher's disease type 3, metachromatic leukodystrophy, Niemann-Pick disease type C, pantothenate kinase-associated neurodegeneration, Tay-Sachs disease and Wilson's disease. Vitamin deficiencies and chronic infections may also occasionally mimic degenerative dementia. These include deficiencies of vitamin B12, folate or niacin, and infective causes including cryptococcal meningitis, HIV, Lyme disease, progressive multifocal leukoencephalopathy, subacute sclerosing panencephalitis, syphilis and Whipple's disease. With respect to rapidly progressive dementia, Creutzfeldt-Jakob disease typically causes a dementia which worsens over weeks to months, being caused by prions. The common causes of slowly progressive dementia also sometimes present with rapid progression, e.g. Alzheimer's disease, dementia with Lewy bodies, and frontotemporal lobar degeneration (including corticobasal degeneration and progressive supranuclear palsy).

In addition, encephalopathy or delirium may develop relatively slowly and result in dementia. Possible causes include brain infection (viral encephalitis, subacute sclerosing panencephalitis, Whipple's disease) or inflammation (limbic encephalitis, Hashimoto's encephalopathy, cerebral vasculitis); tumors such as lymphoma or glioma; drug toxicity (e.g. anticonvulsant drugs); metabolic causes such as liver failure or kidney failure; and chronic subdural hematoma. The dementia that is treated according to methods of the present invention may also be the result of other conditions or illnesses. For example, there are many medical and neurological conditions in which dementia only occurs late in the illness, or as a minor feature. For example, a proportion of patients with Parkinson's disease develop dementia, Cognitive impairment also occurs in the Parkinson-plus syndromes of progressive supranuclear palsy and corticobasal degeneration (and the same underlying pathology may cause the clinical syndromes of frontotemporal lobar degeneration). Chronic inflammatory conditions of the brain may affect cognition in the long term, including Behcet's disease, multiple sclerosis, sarcoidosis, Sjögren's syndrome and systemic lupus erythematosus. In addition, inherited conditions may also cause dementia alongside other features include: Alexander disease, Canavan disease, cerebrotendinous xanthomatosis, fragile X-associated tremor/ataxia syndrome, glutaric aciduria type 1, Krabbe's disease, maple syrup urine disease, Niemann Pick disease type C, Kufs' disease, neuroacanthocytosis, organic acidemias, Pelizaeus-Merzbacher disease, urea cycle disorders, Sanfilippo syndrome type B, and spinocerebellar ataxia type 2.

In addition to treating dementia, the HGF mimics of the invention may be used for neuroprotection and/or to treat neurodegenerative diseases, some of which also involve dementia as described above. For neuroprotection, the HGF mimics may be administered propylactically, i.e. prior to a subject's encounter with or exposure to a potential neurohazard. For example, the mimics may be administered prior to exposure to a drug, chemical or medical procedure that is known or likely to cause neuronal damage. With respect to the treatment of neurodegenerative diseases, the general pro-survival anti-apoptotic activity of HGF supports the use of HGF mimetics for treating neurodegenerative diseases including but not limited to Parkinson's disease, Huntington's disease, and amyotrophic lateral sclerosis (ALS), etc.

In addition, the mimics may be used for the treatment of "depression", by which we mean major depressive disorder (MDD) (also known as recurrent depressive disorder, clinical depression, major depression, unipolar depression, or unipolar disorder) and also depression that is characteristic of bipolar disorder, etc. Depression is ultimately a disease in which neurons and synaptic contacts are lost in the hippocampus. The capacity of HGF to induce new synaptic connections and stimulate neurogenesis in the hippocampus supports the use of HGF mimetics for the treatment of depression.

In addition, the cognitive abilities of persons afflicted with certain genetic predispositions to cognitive dysfunction may also be increased, e.g. persons with genetic disorders such as Down's syndrome, lack of proper brain development e.g. due to lack of oxygen before or during birth, various congenital disorders which interfere with brain development, etc.

As demonstrated in the Examples below, the HGF mimics can inhibit the HGF/Met system, and therefore can be used as anti-cancer agents. The HGF mimics may be used to attenuate malignant and metastatic transformations.

The HGF mimics have application in the therapy of Fibrotic Disease. Hepatic, renal, cardiac, and pulmonary fibrosis is a growing problem in our aging population. Unfortunately, the degradation of function that accompanies fibrotic changes is difficult to treat. The dramatic ability of HGF to inhibit or reverse tissue fibrosis suggests that orally-active HGF mimics provides a therapeutic option.

The HGF mimics have application in the therapy of Peripheral Vascular Disease: Lower Extremity Arterial Disease. Vascular disease resulting in poor perfusion is a common sequel of diabetes, obesity, and atherosclerosis. One treatment option is the induction of new collateral vessels in the effected organs and tissues. The potent angiogenic activity of HGF and HGF mimics can provide a clinical utility for the treatment of vascular insufficiency.

HGF mimics may also be used for Wound Healing. Defective wound healing is a hallmark of diabetics and burn victims. The ability of HGF to promote wound healing because of its angiogenic and mitogenic activities supports the use of HGF mimics to enhance the wound healing process. Data indicates that several HGF mimics are effective wound repair enhancers in both normal and diabetic individuals.

Without being bound by theory, it is believed that the likely mechanism underlying this marked pro-cognitive activity is augmented synaptic connectivity. This is likely due to an increase in miniature synaptic activity brought about by increasing dendritic spine densities and altering the morphological phenotype of postsynaptic spines.

The foregoing Examples are provided in order to illustrate various embodiments of the invention, but should not be interpreted as limiting the invention in any way.

EXAMPLES

Example 1

Regulation of Synaptogenesis by Dihexa and Nle1-AngIV

The tetrapeptide (Nle1-YIH) and tripeptide (Nle1-YI) fragments of the Nle1-AngIV analog of AngIV were previously found to be the smallest active fragments capable of overcoming scopolamine-induced cognitive dysfunction in a spatial learning task. Using the tripeptide as a new template, additional active analogues were synthesized with improved metabolic stability, blood brain barrier permeability, and oral activity. In this Example, we show the characterization of the novel, orally active, angiotensin IV analogue Dihexa.
Materials and Methods
Animals and Surgery.

Male Sprague-Dawley rats (Taconic derived) weighing 390-450 g were maintained with free access to water and food (Harland Tekland F6 rodent diet, Madison, Wis.) except the night prior to surgery when food was removed. Each animal was anesthetized with Ketamine hydrochloride plus Xylazine (100 and 2 mg/kg im. respectively; Phoenix Scientific; St. Joseph, Mo., and Moby; Shawnee, Kans.). An intracerebroventricular (icy) guide cannula (PE-60, Clay Adams; Parsippany, N.Y.) was stereotaxically positioned (Model 900, David Kopf Instruments; Tujunga, Calif.) in the right hemisphere using flat skull coordinates 1.0 mm posterior and 1.5 mm lateral to bregma (refer to Wright et al. 1985). The guide cannula measured 2.5 cm in overall length and was prepared with a heat bulge placed 2.5 mm from its beveled tip, thus acting as a stop to control the depth of penetration. Once in position, the cannula was secured to the skull with two stainless-steel screws and dental cement. Post-operatively the animals were housed individually in an American Accreditation for Laboratory Animal Care-approved vivarium maintained at 22±1° C. on a 12-h alternating light/dark cycle initiated at 06:00 h. All animals were hand gentled for 5 min per day during the 5-6 days of post-surgical recovery. Histological verification of cannula placement was accomplished by the injection of 5 µl fast-green dye via the guide cannula following the completion of behavioral testing. Correct cannula placement was evident in all rats utilized in this study.
Behavioral Testing.

The water maze consisted of a circular tank painted black (diameter: 1.6 m; height: 0.6 m), filled to a depth of 26 cm with 26-28° C. water. A black circular platform (diameter: 12 cm; height: 24 cm) was placed 30 cm from the wall and submerged 2 cm below the water surface. The maze was operationally sectioned into four equal quadrants designated NW, NE, SW, and SE. For each rat the location of the platform was randomly assigned to one of the quadrants and remained fixed throughout the duration of training. Entry points were at the quadrant corners (i.e. N, S, E, and W) and were pseudo-randomly assigned such that each trial began at a different entry point than the preceding trial. Three of the four testing room walls were covered with extra-maze spatial cues consisting of different shapes (circles, squares, triangles) and colors. The swimming path of the animals was recorded using a computerized video tracking system (Chromotrack; San Diego Instruments, CA). The computer displayed total swim latency and swim distance. Swim speed was determined from these values.

Each member of the treatment groups in the scopolamine studies received an icy injection of scopolamine hydrobromide (70 nmol in 2 µl aCSF over a duration of 20 s) 30 min prior to testing followed by Dihexa 10 min prior to testing. Control groups received scopolamine or aCSF 20 min prior to testing followed by aCSF 10 min prior testing. The behavioral testing protocol has been described previously in detail (Wright et al. 1999). The rats in the aged rat study on received Dihexa of aCSF (control group). Briefly, acquisition trials were conducted on 8 consecutive days with 5 trials/day. On the first day of training the animal was placed on the platform for 30 s prior to the first trial. Trials commenced with the placement of the rat facing the wall of the maze at one of the assigned entry points. The rat was allowed a maximum of 120 s to locate the platform. Once the animal located the platform it was permitted a 30 s rest period on the platform. If the rat did not find the platform, the experimenter placed the animal on the platform for the 30 s rest period. The next trial commenced immediately following the rest period.

Following day 8 of acquisition training, one additional trial was conducted during which the platform was removed (probe trial). The animal was required to swim the entire 120 s to determine the persistence of the learned response. Total time spent within the target quadrant where the platform had been located during acquisition and the number of crossings of that quadrant was recorded. Upon completion of each daily set of trials the animal was towel-dried and placed under a 100 watt lamp for 10-15 min and then returned to its home cage.
Hippocampal Cell Culture Preparation.

Hippocampal neurons ($2 \times 10^5$ cells per square cm) were cultured from P1 Sprague Dawley rats on plates coated with poly-L-lysine from Sigma (St. Louis, Mo.; molecular weight 300,000). Hippocampal neurons were maintained in Neurobasal A media from Invitrogen (Carlsbad, Calif.) supplemented with B27 from Invitrogen, 0.5 mM L-glutamine, and 5 mM cytosine-D-arabinofuranoside from Sigma added at 2 days in vitro. Hippocampal neurons were then cultured a further 3-7 days, at which time they were either transfected or treated with various pharmacological reagents as described in (Wayman, Davare et al. 2008).
Transfection.

Neurons were transfected with mRFP-β-actin on day in vitro 6 (DIV6) using LipofectAMINE™ 2000 (Invitrogen) according to the manufacturer's protocol. This protocol yielded the desired 3-5% transfection efficiency thus enabling the visualization of individual neurons. Higher efficiencies obscured the dendritic arbor of individual neurons. Expression of fluorescently tagged actin allowed clear visualization of dendritic spines, as dendritic spines are enriched in actin. On DIV7 the cells were treated with vehicle ($H_2O$) or peptides (as described in the text) added to media. On DIV 12 the neurons were fixed (4% paraformaldehyde, 3% sucrose, 60 mM PIPES, 25 mM HEPES, 5 mM EGTA, 1 mM $MgCl_2$, pH 7.4) for 20 min at room temperature and mounted. Slides were dried for at least 20 hours at 4° C. and fluorescent images were obtained with Slidebook 4.2 Digital Microscopy Software driving an Olympus IX81 inverted confocal microscope with a 60× oil immersion lens, NA 1.4 and resolution 0.280 μm Dendritic spine density was measured on primary and secondary dendrites at a distance of at least 150 μm from the soma. Five 50 μm long segments of dendrite from at least 10 neurons per data point were analyzed for each data point reported. Each experiment was repeated at least three times using independent culture preparations. Dendrite length was determined using the National Institutes of Health's Image J 1.41o program (NIH, Bethesda, Md.) and the neurite tracing program Neuron J (Meijering, Jacob et al. 2004) Spines were manually counted.

Organotypic Hippocampal Slice Culture Preparation and Transfection.

Hippocampi from P4 Sprague Dawley rats were cultured as previously described (Wayman, Impey et al. 2006). Briefly, 400 μm slices were cultured on (Milipore, Billerica, Mass.) for 3 days after which they were biolistically transfected with tomato fluorescent protein (TFP) using a Helios Gen Gun (BioRad, Hercules, Calif.), according to the manufacturer's protocol, to visualize dendritic arbors. Following a 24 hour recovery period slices were stimulated with vehicle ($H_2O$), 1 pM Nle1-AngIV or Dihexa for 2 days. Slices were fixed and mounted. Hippocampal CA1 neuronal processes were imaged and measured as described above.

Immunocytochemistry.

Transfected neurons were treated, fixed and stained. Briefly, cells were permeablized with 0.1% Triton X-100 detergent (Bio-Rad; Hercules, Calif.) for 10 minutes. An 8% bovine serum albumin (Intergen Company; Burlington, Mass.) in PBS was used to prevent non-specific binding for one hour at R.T.; Primary antibody incubations were at a 1:2500 dilution (see below) in 1% BSA in PBS at 4° C. overnight. Secondary antibody, 1:3000 Alexafluor 488 goat-anti-mouse (Invitrogen: Carlsbad, Calif.) was applied for two hours at room temperature. Coverslips were mounted with ProLong Gold anti-fade reagent (Invitrogen; Carlsbad, Calif.) and all washes were done with PBS. Imaging and analysis were performed as described above. For presynaptic excitatory transmission the VGLUT1 (Synaptic Systems, Goettingen, Germany) marker (Balschun, Moechars et al.) was employed and for general presynaptic transmission synapsin1 (Synaptic Systems, Goettingen, Germany) (Ferreira and Rapoport 2002) was applied. A postsynaptic function was established by PSD-95 (Milipore, Billerica, Mass.) (El-Husseini, Schnell et al. 2000). In each instance the total number of spines was counted for the treatment groups, control, Nle1-AngIV and Dihexa, to ensure an active phenotype. The total number of actin enriched spines adjacent to VGLUT1 or Synapsin were counted and converted to a percentage as the percent correlation of treatment-induced spines to presynaptic markers is a strong indicator of ability to transmit excitatory signals. In our application the number of correlations consisted of red fluorescent-tagged actin spines against green PSD-95 immunopositive puncta which, when merged, resulted in an orange spine.

Whole-Cell Recordings.

Patch-clamp experiments were performed on mRFP-β-actin transfected cultured hippocampal neurons (vehicle control) and on transfected hippocampal neurons with 1 pM Nle1-AngIV or Dihexa 5 day pretreatment. Recordings were taken from neurons that were pyramidal-like in shape (~20 μm cell bodies and asymmetric dendrite distribution). The time after transfection was 6 days. The culture medium was exchanged by an extracellular solution containing (in mM) 140 NaCl, 2.5 KCl, 1 $MgCl_2$, 3 $CaCl_2$, 25 glucose, and 5 HEPES; pH was adjusted to 7.3 with KOH; osmolality was adjusted to 310 mOsm. Cultures were allowed to equilibrate in a recording chamber mounted on inverted microscope (IX-71; Olympus optical, Tokyo) for 30 min before recording. Transfected cells were visualized with fluorescence (Olympus optical). Recording pipettes were pulled (P-97 Flaming/Brown micropipette puller; Sutter Instrument, Novato, Calif.) from standard-wall borosilicate glass without filament (OD=1.5 mm; Sutter Instrument). The pipette-to-bath DC resistance of patch electrodes ranged from 4.0 to 5.2MΩ, and were filled with a internal solution of the following composition (in mM): 25 CsCl, 100 $CsCH_3O_3S$, 10 phosphocreatine, 0.4 EGTA, 10 HEPES, 2 $MgCl_2$, 0.4 Mg-ATP, and 0.04 Na-GTP; pH was adjusted to 7.2 with CsOH; osmolality was adjusted to 296-300 mOsm. Miniature EPSCs (mEPSCs) were isolated pharmacologically by blocking GABA receptor chloride channels with picrotoxin (100 μM; Sigma), blocking glycine receptors with strychnine (1 μM; Sigma), and blocking action potential generation with tetrodotoxin (TTX, 500 nM; Tocris). Recordings were obtained using a Multiclamp 700B amplifier (Molecular Devices, Sunnyvale, Calif.). Analog signals were low-pass Bessel filtered at 2 kHz, digitized at 10 kHz through a Digidata 1440A interface (Molecular Devices), and stored in a computer using Clampex 10.2 software (Molecular Devices). The membrane potential was held at −70 mV at room temperature (25° C.) during a period of 0.5-2 h after removal of the culture from the incubator. Liquid junction potentials were not corrected. Data analysis was performed using Clampfit 10.2 software (Molecular Devices), and Mini-Analysis 6.0 software (Synaptosoft Inc.; Fort Lee, N.J.). The criteria for successful recording included the electrical resistance of the seal between the outside surface of the recording pipette and the attached cell >2 GΩ, neuron input resistance >240 M. The mEPSCs had a 5-min recording time.

Results

Figure 1A:
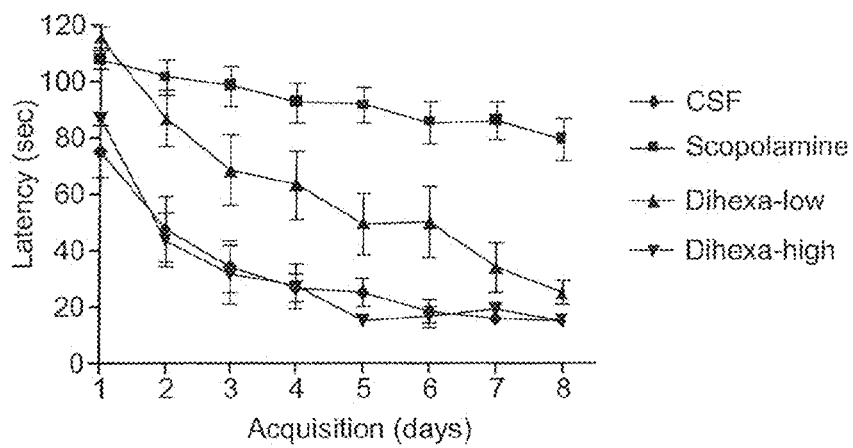
FIGS. 1A, B, and C. Effect of Dihexa on spatial learning in the water maze. A: 30 minutes before beginning testing rats were given scopolamine directly into the brain intracerebroventricularly (ICV) and 10 minutes later Dihexa was given ICV at 10 pmoles (low dose) or 100 pmoles (high dose). This was done daily before the first training trial. There were 5 trials per day for 8 days. The latency to find the pedestal was considered a measure of learning and memory. Rats receiving high Dihexa were able to completely overcome the scopolamine deficits and were no different than controls. B. 30 minutes before beginning testing rats were given scopolamine directly into the brain intracerebroventricularly (ICV) and 10 minutes later Dihexa was given orally 1.25 mg/kg/day (low dose) and 2 mg/kg/day (high dose). This was done daily before the first training trial. There were 5 trials per day for 8 days. The latency to find the pedestal was considered a measure of learning and memory. Rats receiving high dose Dihexa were able to completely overcome the scopolamine deficits and were no different than controls. B: Aged rats of mixed sex and age (22-26 months) were randomly assigned to a control/untreated group or a Dihexa treated group (2 mg/kg/day). Rats were not prescreened. Note that normally-50% of aged rats show deficits, thus the large group errors. The Dihexa group performed significantly better than untreated controls.
Figure 1B:
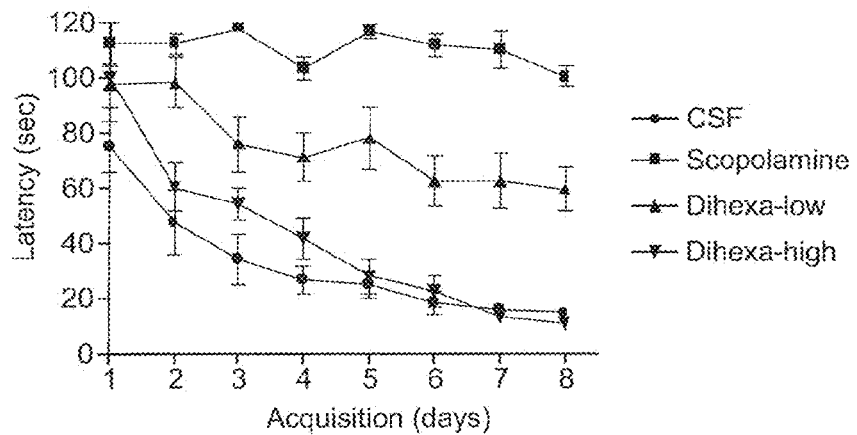
Figure 1C:
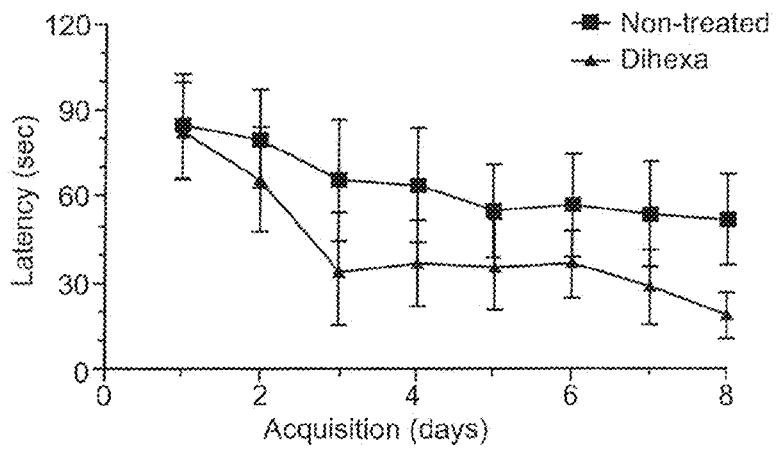

Nle1-AngIV has long been known to be a potent cognitive enhancing agent (Wright and Harding, 2008) but is limited in terms of clinical utility by its metabolic instability ($t_{1/2}$=1.40 minutes in rat serum). In order to exploit the pro-cognitve properties of AngIV like molecules more metabolically stable analogs needed to be developed. As part of this development process Dihexa (N-hexanoic-Tyr-Ile-(6)-aminohexanoic amide) was synthesized and characterized ($t_{1/2}$=330 minutes in rat serum). To determine if the stabilized analog, Dihexa still possessed pro-cognitive/anti-dementia activity it was tested in two dementia models—the scolpolamine amnesia and the aged rat models. These studies demonstrated that Dihexa was able to reverse the cognitive deficits observed in both models. Dihexa delivered either intracerebroventricularly or orally by gavage improved water maze performance reaching performance levels seen in young healthy rats. In FIG. 1A Dihexa delivered at 100 pmoles (n=8, p<0.01) but not 10 pmoles reversed scopolamine-dependent learning deficits as evidenced by an escape latency equivalent to non-scopolamine treated controls. Similar results were seen when Dihexa was delivered orally (FIG. 1B) at both low (1.25 mg/kg/day) and high (2 mg/kg/day). The high dose group's performance was no different than controls (n=8, p<0.01). Randomly grouped aged rats (20-24 weeks) included both sexes were similarly treated with oral Dihexa over the 8 day test period (n=8) and compared to untreated controls (FIG.

1C). The results indicate that the treated rats preformed significantly better in the water maze than untreated rats. ($p<0.05$).

Figure 2A:
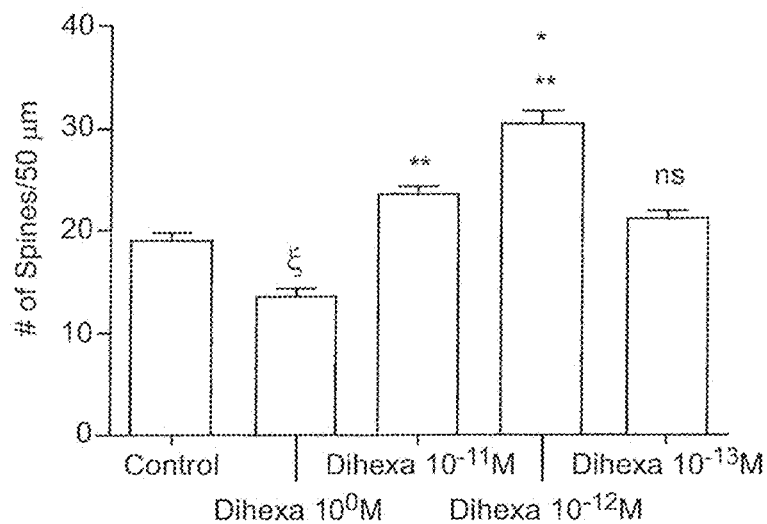
FIGS. 2A and B. Dihexa and Nle$^1$-AngIV dose-dependently stimulate spinogenesis. A) Dihexa and B) Nle$^1$-AngIV increase spine density in mRFP-β-actin transfected hippocampal neurons in a dose-dependent manner. Neurons were stimulated with Dihexa or Nle1-AngIV over a 5 day period at a wide range of concentrations. Data obtained from separate cultures; cultures were 12 days old at time of fixing. The number of dendritic spines on representative 50 μm dendrite segments were hand counted. =$p<0.05$ and *=$p<0.001$; n=50; mean±S.E.M.; ξ=significantly different from control.
Figure 2B:
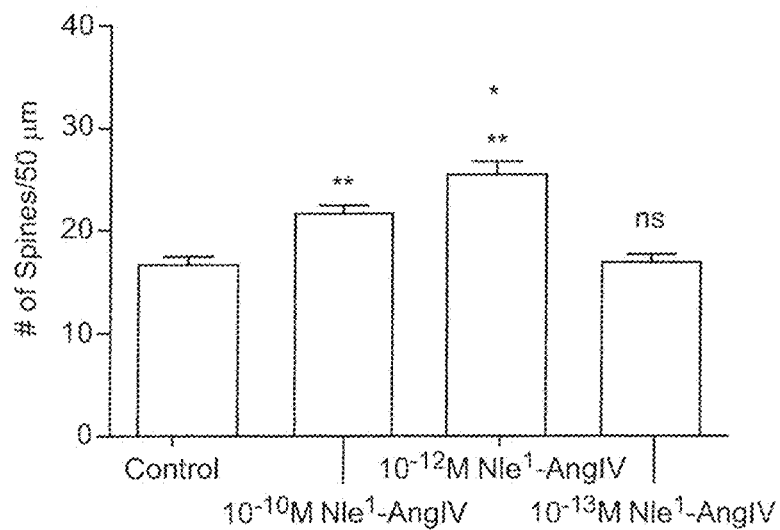

One hypothesis that was put forward to explain the pro-cognitive effects of Nle1-AngIV and Dihexa was that they were acting as hepatocyte growth factor mimetics and as such may be supporting he expansion of neuronal connectivity by inducing the growth of dendritic spines and the establishment of numerous new synapses. To determine the influence of Dihexa on spinogenesis and synaptogenesis in high density mRFP-β-actin transfected hippocampal neuronal cultures was assayed. Actin-enriched spines increased in response to Dihexa and Nle1-AngIV treatment in a dose-dependent manner (FIGS. 2A and B). An apparent ceiling effect was produced by $10^{-12}$ M Dihexa application (mean±S.E.M.; 30 spines per 50 μm dendrite length vs. 19 for control; ***=$P<0.001$; n=50 and 100 respectively) while the results of a $10^{-13}$ M dose were not significantly different from control treated neurons (mean±S.E.M.; 21 spines per 50 μm dendrite for both groups vs. 19 for control; *=$P<0.05$; n=95 and 100 respectively). They were however statistically different from the $10^{-12}$ M Dihexa dose. Neurons receiving a $10^{-10}$ M dose of Dihexa had fewer spines than vehicle treated neurons (Mean±S.E.M.; 11 spines per 50 μm dendrite length vs. 19 for control; #=$P<0.01$; n=50 and 100 respectively). Nle1-AngIV similarly induced a dose-dependent increase is spine density with a marked difference in the $10^{-10}$ M dose which promoted spinogenesis (mean±S.E.M.; 22 spines per 50 μm dendrite length vs. 17 for control; =$P<0.01$; n=50). Maximal increases in spine density were again observed following treatment with a $10^{-12}$ M dose (mean±S.E.M.; 25 and 26 spines per 50 μm dendrite length respectively vs. 17 for control; =$P<0.01$; n=50). The $10^{-13}$ M dose of Nle1-AngIV also had no effect on basal spine numbers (mean±S.E.M.; 17 spines per 50 μm dendrite length vs. 17 for control; **=$P<0.01$; n=50).

The effects of a long-term application (5 days) of the AT4 agonists Dihexa and Nle1-AngIV were compared to an acute application of the agonists (30 minutes) at the biologically effective dose of $10^{-12}$ M (FIG. 3A-E). The results revealed a near 3-fold increase in the number of spines stimulated by Dihexa and greater than 2-fold increase for Nle1-AngIV stimulated spines following a 5 day treatment (FIG. 3D). Both treatment groups differed significantly from the vehicle control group for which the average number of spines per 50 μm dendrite length was 15. The average number of spines for the Dihexa and Nle1-AngIV treated groups was 41 and 32 spines per 50 μm dendrite lengths, respectively (mean±S.E.M., n=200; *=$P<0.001$ by one-way ANOVA and Tukey post hoc test). The behavioral data (data not shown) suggest a quick mechanism of action is taking place during acquisition of the spatial memory task. Therefore the ability of both Dihexa and Nle1-AngIV to promote spinogenesis was measured by an acute 30 minute application on the final day of culturing (FIG. 3E). The acute 30 minute application of Dihexa and Nle1-AngIV, on the 12th day in vitro (DIV12) reveals a significant increase in spines compared to 30 minute vehicle treated neurons (Dihexa mean spine numbers per 50 μm dendrite length=23.9±S.E.M.; Nle1-AngIV mean spine numbers=2.6±S.E.M.; mean spine numbers for vehicle control treated neurons=17.4±S.E.M.; n=60; *=$p<0.0001$ by one-way ANOVA followed by Tukey post-hoc test).

Figure 4:
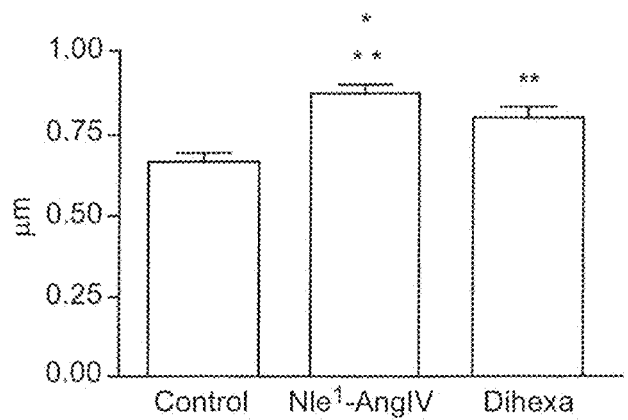
FIG. 4. Nle1-AngIV and Dihexa increase spine head width. The width of the spine head was measured as an indication of synaptic strength. Spine heads with a greater surface area can accommodate more neurotransmitter receptors and are more likely to form functional synapses. The AngIV analogue treatment-induced increase in spine head width suggests facilitated neurotransmission. ***=$p<0.001$; mean±S.E.M.; n=100.

Strong correlations exist between spine size, persistence of spines, number of AMPA-receptors and synaptic efficacy. A correlation between the existence of long-term memories to spine volume has also been suggested (Kasai, Fukuda et al., 2001; Yasumatsu, Matsuzaki et al. 2008). With these considerations in mind spine head size measurements were taken. Results indicate that $10^{-12}$ M doses of Dihexa and Nle1-AngIV increased spine head width (FIG. 4). Average spine head width for Nle1-AngIV=0.87 μm (*=$P<0.001$; mean±S.E.M.) and Dihexa=0.80 μm (=$P<0.01$; mean±S.E.M.) respectively compared to control head size (0.67 μm).

Dihexa and Nle1-AngIV Mediate Synaptogenesis

To quantify synaptic transmission, mRFP-β-actin transfected neurons were immuno-stained against synaptic markers. Hippocampal neurons were stimulated for 5 days in vitro with $10^{-12}$ M Dihexa or Nle1-AngIV (FIG. 5A-F). Nle1-AngIV and Dihexa's neurotransmitter patterns were probed for excitatory synaptic transmission by staining against the glutamatergic presynaptic marker Vesicular Glutamate Transporter 1 (VGLUT1) (Balschun, Moechars et al. 2010). The universal presynaptic marker Synapsin was employed to measure juxtaposition of the newly formed spines with presynaptic boutons (Ferreira and Rapoport 2002). PSD-95 served as a marker for the postsynaptic density (El Husseini, Schnell et al. 2000).

Figure 5A:
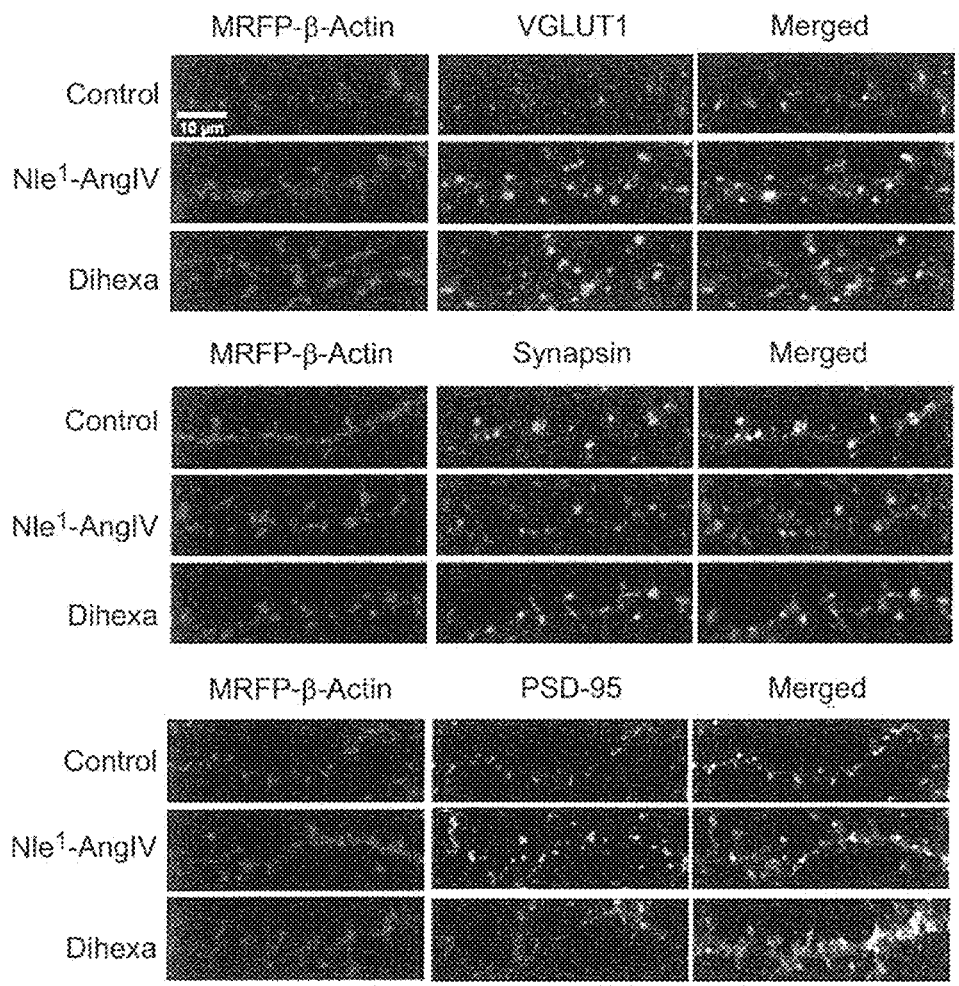
FIG. 5A-G. Neurotransmitter patterns for Nle1-AngIV and Dihexa stimulated neurons. Dihexa and Nle1-AngIV treated neurons were immunostained for the universal presynaptic marker synapsin and the glutamatergic presynaptic marker VGLUT1. The percent correlation between the postsynaptic spines (red) and presynaptic puncta (green) were measured as an indication of functional synapses. A) Bar graph representing an increase in the number of spines following treatment with vehicle, Nle1-AngIV or Dihexa. This ensures an active phenotype in the neurons (*=$P<0.001$; mean±S.E.M.; n=25). B) Bar graph representing the percent correlation of treatment-induced postsynaptic spines to the glutamatergic presynaptic marker VGLUT1. A high percent correlation between the presynaptic marker and the postsynaptic spines suggests that functional connections are formed ($P>0.05$; mean±S.E.M.; n=25). C) Bar graph representing an increase in the number of spines following treatment with vehicle, Nle1-AngIV or Dihexa, ensuring health of the neurons (*=$P<0.001$; mean±S.E.M.; n=25). D) Bar graph representing the percent correlation of treatment-induced postsynaptic spines to the general presynaptic marker Synapsin. No significant differences between the stimulated neurons and vehicle control treated neurons were observed ($P>0.05$; mean±S.E.M.; n=25) suggesting a majority of the presynaptic input is glutamatergic. E) Bar graph representing an increase in the number of spines following treatment with vehicle, Nle1-AngIV or Dihexa, ensuring an active phenotype (***=$P<0.001$; mean±S.E.M.; n=25). F) Bar graph representing the percent correlation of treatment-induced postsynaptic spines to the postsynaptic marker PSD-95. G) Bar graph shows no significant differences ($P>0.05$; mean±S.E.M.; n=25) between the postsynaptic marker PSD-95 and the postsynaptic spines suggest that the newly formed spines have a functional postsynaptic element.
Figure 5B:
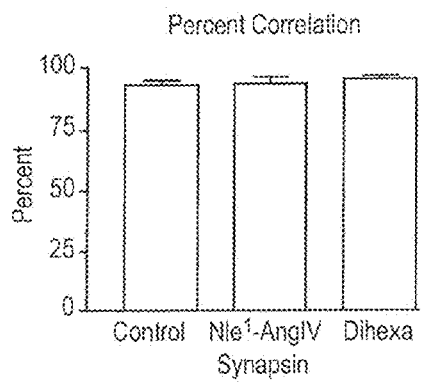
Figure 5C:
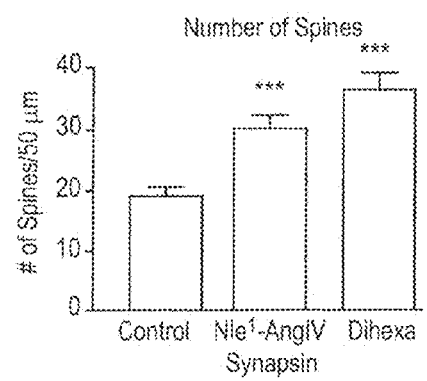
Figure 5D:
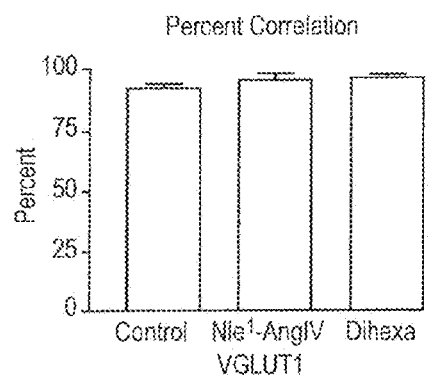
Figure 5E:
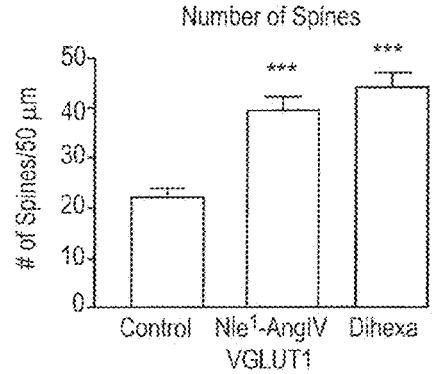
Figure 5F:
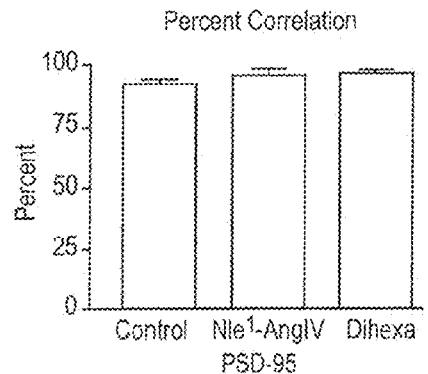
Figure 5G:
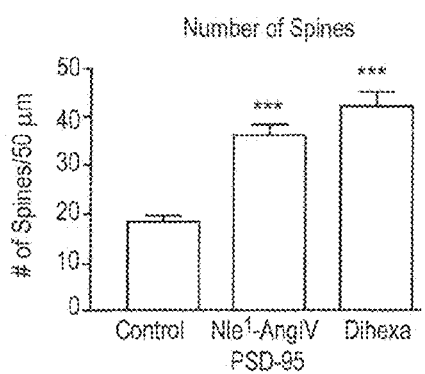

Dihexa and Nle1-AngIV treated neurons significantly augmented spinogenesis; mean spine numbers per 50 μm dendrite length for Nle1-AngIV=39.4; mean spine numbers per 50 μm dendrite length for Dihexa=44.2; mean spine numbers per 50 μm dendrite length for vehicle treated neurons=23.1 (mean±S.E.M., ***=$P<0.001$) (FIGS. 3B, D and F and Table 4). The percent correlation for the newly formed spines to the synaptic markers was calculated as a measure for the formation of functional synapses. Dihexa and Nle1-AngIV treatment-induced spines did not differ from control treated neurons in percent correlation to VGLUT1, Synapsin or PSD-95 ($P>0.05$) (FIGS. 5A, C and E and Table 4).

TABLE 4

Summary of the percent correlation to markers of synaptic components and the number of spines induced by Dihexa and Nle1-AngIV treatment.

| Treatment | Control | Nle1-AngIV | Dihexa |
|---|---|---|---|
| Number of spines/50 μm | 22 | 39 | 44 |
| % Correlation VGLUT1 | 95.2 | 95.1 | 94.4 |
| Number of spines/50 μm | 19 | 31 | 37 |
| % Correlation Synapsin | 93.4 | 94.2 | 96.3 |
| Number of spines/50 μm | 18 | 36 | 43 |
| % Correlation PSD-95 | 98.03 | 97.38 | 98.71 |

The total number of spines for each treatment group is indicated as the number of spines per 50 μm dendrite length. The percent correlation of the presynaptic marker Synapsin, the glutamatergic presynaptic marker VGLUT1 or the postsynaptic component PSD-95 is reported directly below. N=25 for each treatment group.

Figure 6A:
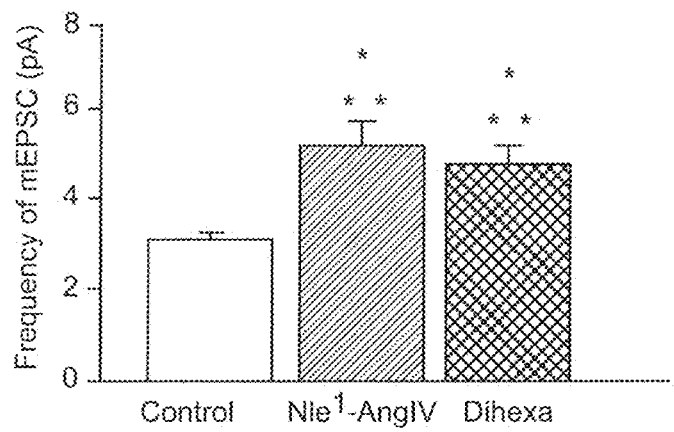
FIGS. 6A and B. Mini-excitatory postsynaptic currents (mEPSCs) in dissociated hippocampal neurons. Nle1-AngIV and Dihexa treatment increase the frequency of mini-excitatory postsynaptic currents (mEPSCs). Recordings were done on dissociated hippocampal neurons treated with vehicle, $10^{-12}$ M Nle1-AngIV or Dihexa for 5 days prior to recording. The currents recorded were spontaneous bursts of AMPA-mediated synaptic transmission in the absence of action potentials carried in the presence of strychnine, picrotoxin and tetrodotoxin. A) Representative traces of mEPSC recordings from Nle1-AngIV or Dihexa treated hippocampal neurons. B) Bar graph representing the increase in AMPA-mediated frequencies from Nle1-AngIV or Dihexa treated hippocampal neurons. The increased frequencies indicate that spines induced by Nle1-AngIV or Dihexa support functional synapses. ***=$p<0.001$; ±S.E.M.; n=25.
Figure 6B:
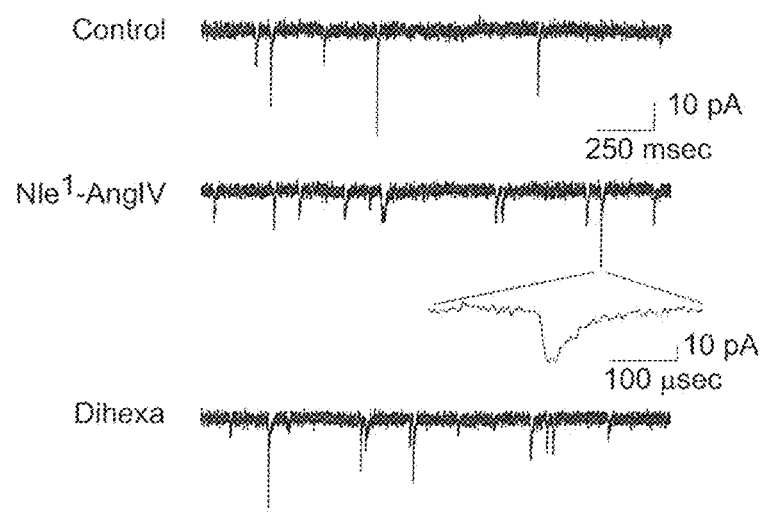

The above results suggest that the newly formed dendritic spines produced by Dihexa and Nle1-AngIV treatment are creating functional synapses. To further support this conclusion, mini postsynaptic excitatory currents (mEPSCs), the frequency of which corresponds to the number of functional synapses were recorded from mRFP-β-actin transfected hippocampal neurons. A near two-fold increase in the AMPA-mediated currents was measured following treatment with 10-12 M Nle1-AngIV and Dihexa (FIGS. 6A and B). The mean frequency of AMPA-mediated mEPSCs recorded from vehicle treated neurons was 3.06±0.23 Hz from 33 cells. Nle1-AngIV induced a 1.7 fold increase over percent control frequency (5.27, 0.43 Hz from 25 cells; Mean±S.E.M.; *=$P<0.001$ vs. control group and Dihexa produced a 1.6 fold increase (4.82, 0.34 Hz from 29 cells; *=$P<0.001$ vs.

control group confirming an amplification of functional synapses. No differences in amplitude, rise- or decay-times were observed (data not shown) which suggests that the individual properties of the synapse were not altered.

Figure 7A:
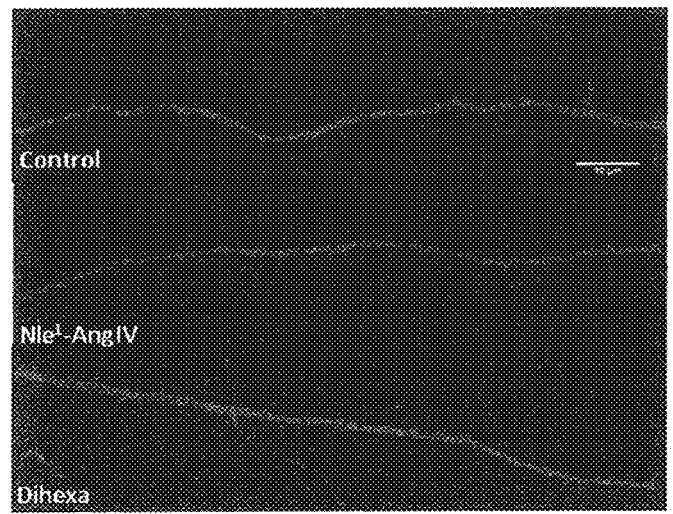
FIGS. 7A and B. Evaluation of Nle1-AngIV- and Dihexa-dependent spinogenesis in CA1 hippocampal neurons from rat organotypic hippocampal slice cultures. Nle1-AngIV- and Dihexa were found to support spinogenesis in CA1 hippocampal neurons. Organotypic hippocampal slice cultures (400 μM thicknesses), representing a more intact environment, were biolistically transfected with the soluble red fluorescent protein Tomato. CA1 hippocampal neurons were selected for evaluation because of their known plastic response during learning. Slices were obtained from postnatal day 5 rats. A) Representative images of CA1 neuronal dendrites from Tomato transfected hippocampal slices. Images represent a 2 day treatment with 10-12 M Nle1-AngIV or Dihexa. B) Treatment-induced spinogenesis is observed in CA1 pyramidal hippocampal neurons. Spine numbers measured for control slices were 7 per 50 μm dendrite length vs. 11 spines per 50 μm dendrite length for both Nle1-AngIV and Dihexa treated neurons; Mean±S.E.M., n=17; **=$P<0.01$ Statistical significance by one-way ANOVA followed by Tukey Multiple Comparisons Test; Experiments were repeated at least three times.

To further assess the physiological significance of the spine induction witnessed in dissociated neonatal hippocampal neurons the effects of Dihexa and Nle1-AngIV on spine formation in organotypic hippocampal slice cultures was evaluated. These preparations, while still neonatal in origin, represent a more intact and three dimensional environment than dissociated neurons. Hippocampal CA1 neurons, which have been functionally linked to hippocampal plasticity and learning/memory, could be easily identified based on morphology and were singled out for analysis. Dihexa and Nle1-AngIV significantly augmented spinogenesis in organotypic hippocampal slice cultures when compared to vehicle treated neurons. There were no differences in spine numbers between the Dihexa and Nle1-AngIV treatment groups (FIGS. 7A and B). Spine numbers measured for control slices were 7 per 50 μm dendrite length vs. 11 spines per 50 μm dendrite length for both Nle1-AngIV and Dihexa treated neurons; mean±S.E.M., n=13-20; **=P<0.01.

Discussion

In this study, Dihexa like Nle1-AngIV was a potent cognitive enhancer when given either ICV or orally. As predicted, Dihexa and Nle1-AngIV both promoted spinogenesis and enhance synaptogenesis in cultured rat hippocampal neurons. As expected of an angiotensin IV analogue, Dihexa exerted spine induction effects at sub-nano-molar concentrations (Harding, Cook et al. 1992; Krebs, Hanesworth et al. 2000) with some spine formation by Dihexa and Nle1-AngIV occurring as early as 30 minutes after stimulation (FIG. 3D). The maximal effect, however, requires a significantly longer treatment period (FIG. 3C).

Spine head size measurements were taken as an indicator of synaptic potentiation. Larger spines with a greater surface area tend to have larger synapses, a larger PSD to recruit scaffolding proteins, and a greater number of glutamatergic receptive neurotransmitter receptors (Kennedy 1997). Although not different from one another (P>0.05), both Dihexa and Nle1-AngIV treatment groups exhibited large expansions in spine head size. Changes in spine morphology and numbers are proposed to be mechanisms for converting short-term synaptic changes into highly stable and long-lasting changes (Hering and Sheng 2001).

To evaluate the functional significance of these spine changes Nle1-AngIV and Dihexa stimulated hippocampal neurons were immunostained against the glutamatergic presynaptic marker VGLUT1 (Balschun, Moechars et al. 2010), the general presynaptic marker Synapsin (Ferreira and Rapoport 2002) and the postsynaptic marker PSD-95 (Kennedy 1997; Han and Kim 2008) to decipher neurotransmitter phenotypes. The high and unaltered correlation between VGLUT1, Synapsin, and PSD-95 in both treated and control dendrites suggests that the newly minted spines support functional synapses (FIG. 5 and Table 4) (Han and Kim 2008; Yasumatsu, Matsuzaki et al. 2008). Further, a near perfect correlation between mRFP-β-actin labeled spines and the general presynaptic marker Synapsin and VLGUT1 staining, which identifies excitatory glutamatergic synapses suggests that most AngIV-dependent effects on hippocampal spines were restricted to excitatory synapses. These findings correspond nicely with the findings of De Bundel et al. in which no effect on the inhibitory neurotransmitter GABA by native angiotensin IV was observed (De Bundel, Demaegdt et al. 2010).

The increase in mEPSC frequency observed by Dihexa and Nle1-AngIV treated preparations further supports that new spines form functional synapses (Malgaroli and Tsien 1992; Hering and Sheng 2001; Tyler and Pozzo-Miller 2003). The consistent strengthening of neurotransmission initiated by Dihexa and Nle1-AngIV could not be attributed to intrinsic fluctuations of neurotransmitter release or metabolic and mechanical influences (Yasumatsu, Matsuzaki et al. 2008). The data presented here suggest that Nle1-AngIV and Dihexa increase miniature synaptic activity by increasing dendritic spine densities and altering the morphological phenotype of postsynaptic spines in-vitro and may represent the mechanism that underlies facilitated learning observed AngIV analogues (Wright, Stubley et al. 1999; Lee, Albiston et al. 2004).

Figure 7B:
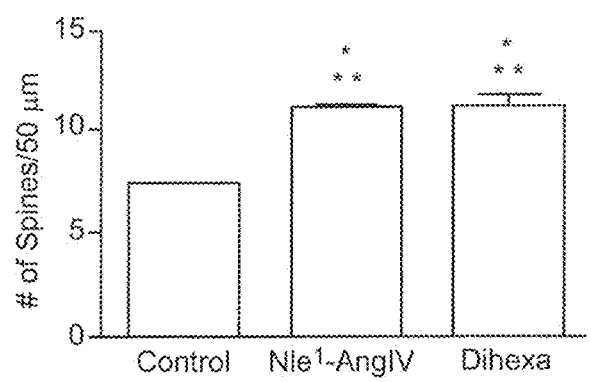

To bridge the adult behavioral data to the in vitro mechanistic theory, organotypic hippocampal slice cultures that maintain an environment representative of an intact hippocampus were employed and evaluated for treatment-induced spinogenesis. Application of $10^{-12}$ M Nel-AngIV and Dihexa in ballistically transfected hippocampal slices significantly increase spine densities (FIG. 7) implying that such changes may in fact be occurring in the intact hippocampus.

Thus, Dihexa fits the criteria necessary for an effective anti-dementia drug: 1) it is orally active, as it survives passage through the gut and enters the brain; 2) it augments neuronal connectivity, a necessary property when faced with loss of neuronal connectivity; and 3) it is inexpensive to synthesize thus making it accessible to patients.

Example 2

The Target of AngIV Analogs is Hepatocyte Growth Factor

This Example shows that the novel angiotensin IV ligand Dihexa and its parent molecule Nle1-AngIV act through the HGF/c-Met receptor system.

Materials and Methods

Animals and Surgery

Male Sprague-Dawley rats (Taconic derived) weighing 390-450 g were maintained with free access to water and food (Harland Tekland F6 rodent diet, Madison, Wis.) except the night prior to surgery when food was removed. Each animal was anesthetized with Ketamine hydrochloride plus Xylazine (100 and 2 mg/kg im. respectively; Phoenix Scientific; St. Joseph, Mo., and Moby; Shawnee, Kans.). An intracerebroventricular (icy) guide cannula (PE-60, Clay Adams; Parsippany, N.Y.) was stereotaxically positioned (Model 900, David Kopf Instruments; Tujunga, Calif.) in the right hemisphere using flat skull coordinates 1.0 mm posterior and 1.5 mm lateral to bregma (Wright et al., 1985). The guide cannula measured 2.5 cm in overall length and was prepared with a heat bulge placed 2.5 mm from its beveled tip, thus acting as a stop to control the depth of penetration. Once in position, the cannula was secured to the skull with two stainless-steel screws and dental cement. Post-operatively the animals were housed individually in an American Accreditation for Laboratory Animal Care-approved vivarium maintained at 22±1° C. on a 12-h alternating light/dark cycle initiated at 06:00 h. All animals were hand gentled for 5 min per day during the 5-6 days of post-surgical recovery.

Behavioral Testing

The water maze consisted of a circular tank painted black (diameter: 1.6 m; height: 0.6 m), filled to a depth of 26 cm with 26-28° C. water. A black circular platform (diameter: 12 cm; height: 24 cm) was placed 30 cm from the wall and submerged 2 cm below the water surface. The maze was operationally sectioned into four equal quadrants designated NW, NE, SW, and SE. For each rat the location of the platform was randomly assigned to one of the quadrants and remained fixed throughout the duration of training. Entry points were at the quadrant corners (i.e. N, S, E, W) and were pseudo-randomly assigned such that each trial began at a different entry point than the preceding trial. Three of the four testing room walls were covered with extra-maze spatial cues consisting of different shapes (circles, squares, triangles) and colors. The swimming path of the animals was recorded using a computerized video tracking system (Chromotrack; San Diego Instruments, CA). The computer displayed total swim latency and swim distance. Swim speed was determined from these values.

Each member of the treatment groups received an icy injection of scopolamine hydrobromide (70 nmol in 2 µl aCSF over a duration of 20 s) 20 min prior to testing followed by Dihexa (300 pmol in 2 µl aCSF), Hinge (300 pmol in 2 pl aCSF), or Hinge+Dihexa (300 pmol in 4 µl aCSF) 5 min prior to testing. This scopolamine preparation is a generally accepted animal model of the spatial memory dysfunction that accompanies dementia (Fisher et al., 2003). Control groups received scopolamine or aCSF 20 min prior to testing followed by aCSF 5 min prior testing. The behavioral testing protocol has been described previously in detail (Wright et al., 1999). Briefly, acquisition trials were conducted on 8 consecutive days, 5 trials/day. On the first day of training the animal was placed on the pedestal for 30 s prior to the first trial. Trials commenced with the placement of the rat facing the wall of the maze at one of the assigned entry points. The rat was allowed a maximum of 120 s to locate the platform. Once the animal located the platform it was permitted a 30 s rest period on the platform.

If the rat did not find the platform, the experimenter placed the animal on the platform for the 30 s rest period. The next trial commenced immediately following the rest period. Upon completion of each daily set of trials the animal was towel-dried and placed under a 100 watt lamp for 10-15 min and then returned to its home cage.

Statistical Analyses

One-way ANOVA was used to analyze the dendritic spine results and significant effects were analyzed by Tukey post-hoc test. Morris water maze data set mean latencies to find the platform during each daily block of five trials were calculated for each animal for each day of acquisition. One-way ANOVAs were used to compare group latencies on Days 1, 4, and 8 of training. Significant effects were analyzed by Newman-Keuls post-hoc test with a level of significance set at $P<0.05$.

Scattering Assay.

MDCK cells were grown to 100% confluency on the coverslips in six-well plates and washed twice with PBS. The confluent coverslips were then aseptically transferred to new six well plates containing 900 µl serum free DMEM. Norleual, Hinge peptide, and/or HGF (20 ng/ml) were added to appropriate wells. Control wells received PBS vehicle. Plates were incubated at 37° C. with 5% $CO_2$ for 48 hours. Media was removed and cells were fixed with methanol. Cells were stained with Diff-Quik Wright-Giemsa (Dade-Behring, Newark, Del.) and digital images were taken. Coverslips were removed with forceps and more digital images were captured. Pixel quantification of images was achieved using Image J and statistics were performed using Prism 5 and InStat v.3.05.

Dissociated Hippocampal Neuronal Cell Culture Preparation

Hippocampal neurons ($2\times10^5$ cells per square centimeter) were cultured from P1-2 Sprague Dawley rats on plates coated with poly-L-lysine from Sigma (St. Louis, Mo.; molecular weight 300,000). Hippocampal neurons were maintained in Neurobasal A media from Invitrogen (Carlsbad, Calif.) supplemented with B27 from Invitrogen, 0.5 mM L-glutamine, and 5 mM cytosine-D-arabinofuranoside from Sigma added at 2 days in vitro. Hippocampal neurons were then cultured a further 3-7 days, at which time they were either transfected or treated with various pharmacological reagents as described in the text or figure legends.

Transfection of Dissociated Hippocampal Neuronal Cell Cultures

Neurons were transfected with mRFP-β-actin on day in vitro 6 (DIV6) using LipofectAMINE™ 2000 (Invitrogen) according to the manufacturer's protocol. This protocol yielded the desired 3-5% transfection efficiency thus enabling the visualization of individual neurons. Higher efficiencies obscured the dendritic arbor of individual neurons. Expression of fluorescently tagged actin allowed clear visualization of dendritic spines, as dendritic spines are enriched in actin. On DIV7 the cells were treated with vehicle (H20) or peptides (as described in the text) added to media. On DIV 12 the neurons were fixed (4% paraformaldehyde, 3% sucrose, 60 mM PIPES, 25 mM HEPES, 5 mM EGTA, 1 mM $MgCl_2$, pH 7.4) for 20 min at room temperature and mounted. Slides were dried for at least 20 hours at 4° C. and fluorescent images were obtained with Slidebook 4.2 Digital Microscopy Software driving an Olympus IX81 inverted confocal microscope with a 60× oil immersion lens, NA 1.4 and resolution 0.280 µm Dendritic spine density was measured on primary and secondary dendrites at a distance of at least 150 µm from the soma. Five 50 µm long segments of dendrite from at least 10 neurons per data point were analyzed for each data point reported. Each experiment was repeated at least three times using independent culture preparations. Dendrite length was determined using the National Institutes of Health's Image J 1.41o program (NIH, Bethesda, Md.) and the neurite tracing program Neuron J (Meijering, Jacob et al. 2004) Spines were manually counted.

Organotypic Hippocampal Slice Culture Preparation and Transfection

Hippocampi from P4 Sprague Dawley rats were cultured as previously described (Wayman, Impey et al. 2006). Briefly, 400 µm slices were cultured on (Milipore, Billerica, Mass.) for 3 days after which they were biolistically transfected with tomato fluorescent protein (TFP) using a Helios Gene Gun (BioRad, Hercules, Calif.), according to the manufacturer's protocol, to visualize dendritic arbors. Following a 24 hour recovery period slices were stimulated with 1 pM Nle1-AngIV or Dihexa for 2 days. Slices were fixed and mounted. Hippocampal CA1 neuronal processes were imaged and measured as described above.

Acute Hippocampal Slices

Adult Sprague-Dawley rats (250 g+) obtained from Harlan Laboratories (Ca, USA) were anesthetized with isofluorane (Vet One™, MWI, Meridian, Id., USA) and decapitated. The brain was rapidly removed and placed into ice-chilled artificial cerebrospinal fluid (aCSF) for approximately 30 s. Both hemispheres were separated by a mid-saggital cut and both hippocampi removed. Slices were sectioned cross- and length-wise (400 µm) to ensure penetrability of the drug, using a McIlwain tissue chopper (Brinkmann, Gomshall, UK) and transferred to a gassed (95% $O_2$/5% $CO_2$) incubation chamber containing aCSF for 90 minutes at room temperature. Slices were transferred to fresh tubes, aCSF was removed by careful suctioning and replaced with aCSF containing vehicle (aCSF+aCSF), 100 ng/ml with carrier free adult recombinant Hepatocyte Growth Factor (HGF) (R and D Systems, MN, USA) in aCSF, $10^{-10}$ M Hinge (Harding lab), 50 ng/ml in aCSF, $10^{-10}$ M Dihexa (Harding lab) in aCSF, $10^{-12}$ M Dihexa in aCSF or 50 ng/ml HGF+$10^{-12}$ M Dihexa in aCSF for 30 minutes at 37° C. with gentle rocking. aCSF was removed and the slices were lysed using RIPA buffer (Upstate/Milipore, Billerica, Mass.) and inhibitor Cocktails I and II (Sigma, St. Louis, Mo.), sonicated on ice and clarified by centrifugation for 30 minutes, 13,000 rpm at 4° C. The supernatant was removed from the pellet and stored at ~80° C. or processed immediately for gel electrophoresis.

shRNA

A target sequence for c-Met was designed using RNAi central design program (see the website located at can-can.cshl.edu/). The target sequence GTGTCAGGAGGT-GTTTGGAAAG (SEQ ID NO: 2) was inserted into pSUPER vector (Oligoengine, Seattle Wash.) which drives endogenous production of shRNA under the H1 promoter. The shRNA was transfected into cells using the lipofectamine method described above. Verification of receptor knockdown was done by creating a c-Met-6-Myc tagged gene product using the Gateway cloning system (Invitrogen). The Met protein coding sequence was cloned from rat whole brain cDNA using primers obtained from Integrated DNA Technologies, Inc. The amplified product was gel purified and a band corresponding to 190 kDa band excised and cloned into a PCAGGS-6-Myc destination vector (Gateway).

Gel Electrophoresis and Western Blotting

Protein concentration of the samples was quantified using the BCA method (Pierce, Rockford, Ill.) following the manufacturers protocol. Samples were added to SDS-PAGE buffer and boiled for 10 min. before loading onto a 4-12% Bis-Tris pre-cast gel (Invitrogen, Carlsbad, Calif.) for electrophoresis. Proteins were transferred onto PVDF membranes (Bio Rad, Hercules, Calif.) and blocked with AquaBlock™ (New England Biolabs, Ipswich, Mass.) for 1 hour at room temperature (RT). Primary antibody incubation was done in AquaBlock™ with rabbit anti-Met and anti-rabbit phospho-Met (Tyr1234/1235) (1:1000, Cell Signaling Technology, Danvers, Mass.) overnight at 4° C. Alternating washes were done with PBS and PBST. Secondary antibody (IRDye) (Rockland, Gilbertsville, Pa.) incubations were done in AquaBlock™ for one hour at RT. Blots were imaged using LI-COR Odyssey Infrared Imaging System (LI-COR Biosciences, Lincoln, Nebr.).

Immunocytochemistry

Transfected neurons were treated, fixed and stained as previously described in Chapter two. Briefly, cells were permeablized with 0.1% Triton X-100 detergent (Bio-Rad; Hercules, Calif.) for 10 minutes. An 8% bovine serum albumin (Intergen Company; Burlington, Mass.) in PBS was used to prevent non-specific binding for one hour at R.T.; Primary antibody incubations were at a 1:2500 dilution (see below) in 1% BSA in PBS at 4° C. overnight. Secondary antibody, 1:3000 Alexafluor 488 goat-anti-mouse (Invitrogen: Carlsbad, Calif.) was applied for two hours at room temperature. Coverslips were mounted with ProLong Gold anti-fade reagent (Invitrogen; Carlsbad, Calif.) and all washes were done with PBS. Imaging and analysis were performed as described above. For presynaptic excitatory transmission the VGLUT1 (Synaptic Systems, Goettingen, Germany) marker (Balschun, Moechars et al.) was employed and for general presynaptic transmission synapsin1 (Synaptic Systems, Goettingen, Germany) (Ferreira and Rapoport 2002) was applied. A postsynaptic function was established by PSD-95 (Milipore, Billerica, Mass.) (El-Husseini, Schnell et al. 2000). In each instance the total number of spines was counted for the treatment groups, control, Nle1-AngIV and Dihexa, to ensure an active phenotype. The total number of actin enriched spines (red) adjacent to VGLUT1 or Synapsin were counted and converted to a percentage as the percent correlation of treatment-induced spines to presynaptic markers is a strong indicator of ability to transmit excitatory signals. In our application the number of correlations consisted of red fluorescent-tagged actin spines against green PSD-95 immuno-positive puncta which, when merged, resulted in an orange spine.

Whole-Cell Recordings

Patch-clamp experiments were performed on mRFP-β-actin transfected cultured hippocampal neurons (vehicle control) and on transfected hippocampal neurons with 1 pM Hinge or Dihexa, or 10 ng/ml HGF (R&D Systems) 5 day pretreatment. Recordings were taken from neurons that were pyramidal-like in shape (~20 μm cell bodies and asymmetric dendrite distribution). The time after transfection was 6 days. The culture medium was exchanged by an extracellular solution containing (in mM) 140 NaCl, 2.5 KCl, 1 $MgCl_2$, 3 $CaCl_2$, 25 glucose, and 5 HEPES; pH was adjusted to 7.3 with KOH; osmolality was adjusted to 310 mOsm. Cultures were allowed to equilibrate in a recording chamber mounted on inverted microscope (IX-71; Olympus optical, Tokyo) for 30 min before recording. Transfected cells were visualized with fluorescence (Olympus optical). Recording pipettes were pulled (P-97 Flaming/Brown micropipette puller; Sutter Instrument, Novato, Calif.) from standard-wall borosilicate glass without filament (OD=1.5 mm; Sutter Instrument). The pipette-to-bath DC resistance of patch electrodes ranged from 4.0 to 5.2MΩ, and were filled with a internal solution of the following composition (in mM): 25 CsCl, 100 $CsCH_3O_3S$, 10 phosphocreatine, 0.4 EGTA, 10 HEPES, 2 $MgCl_2$, 0.4 Mg-ATP, and 0.04 Na-GTP; pH was adjusted to 7.2 with CsOH; osmolality was adjusted to 296-300 mOsm. Miniature EPSCs (mEPSCs) were isolated pharmacologically by blocking GABA receptor chloride channels with picrotoxin (100 μM; Sigma), blocking glycine receptors with strychnine (1 μM; Sigma), and blocking action potential generation with tetrodotoxin (TTX, 500 nM; Tocris). Recordings were obtained using a Multiclamp 700B amplifier (Molecular Devices, Sunnyvale, Calif.). Analog signals were low-pass Bessel filtered at 2 kHz, digitized at 10 kHz through a Digidata 1440A interface (Molecular Devices), and stored in a computer using Clampex 10.2 software (Molecular Devices). The membrane potential was held at −70 mV at room temperature (25° C.) during a period of 0.5-2 h after removal of the culture from the incubator. Liquid junction potentials were not corrected. Data analysis was performed using Clampfit 10.2 software (Molecular Devices), and Mini-Analysis 6.0 software (Synaptosoft Inc.; Fort Lee, N.J.). The criteria for successful recording included the electrical resistance of the seal between the outside surface of the recording pipette and the attached cell >2 GΩ, neuron input resistance >240 MΩ. The mEPSCs had a 5-min recording time.

Results

Hepatocyte Growth Factor Augments the Dendritic Architecture and Supports Synaptogenesis Dihexa and Nle1-AngIV have previously been shown to induce spinogenesis in mRFP-β-actin transfected hippocampal neurons (see Example 1); however the mechanism underlying this action was unknown. Because of the ability of Norleual, another AngIV analogue to block the action of HGF on c-Met (Yamamoto et al., 2010) we hypothesized that increases in spine density initiated by Dihexa and Nle1-AngIV are mediated by the HGF/c-Met system. As such, the effects of HGF on spinogenesis in dissociated hippocampal cultures were evaluated. Hippocampal neurons were transfected with mRFP-β-actin on day in vitro (DIV) 6 and stimulated with HGF for 5 days.

Figure 8:
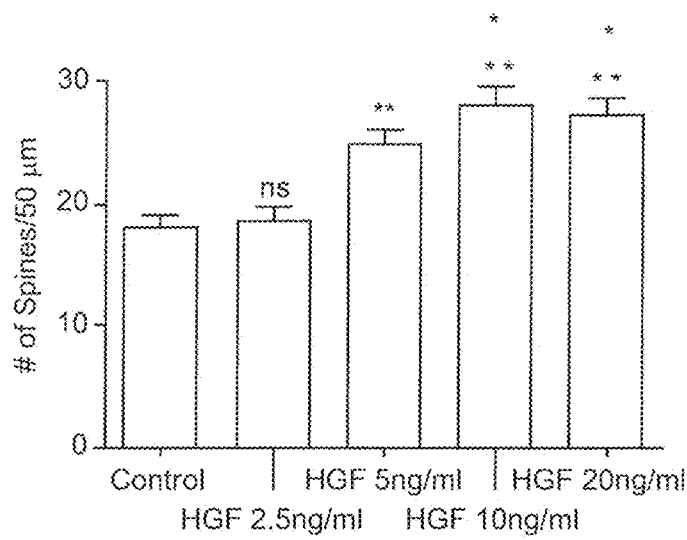
FIG. 8. HGF dose-dependently enhances spinogenesis. Effect of HGF on spinogenesis in dissociated hippocampal neurons. Dissociated hippocampal neurons from 1 or 2 day old rats were transfected with mRFP-β-actin and stimulated with HGF for 5 days. Treatment with 2.5 ng/ml HGF did not affect basal spine numbers and was considered sub-threshold. Doses of 5, 10 and 20 ng/ml significantly increased the number of spines per 50 μm dendrite lengths compared to vehicle control treated neurons. *** $P<0.001$; mean±S.E.M.; n=50 per treatment group.

A dose-dependent increase in spine numbers following HGF stimulation was observed with the lowest effective dose being 5 ng/ml dose (mean spine numbers=24.7; =p<0.01 vs. control; ns vs HGF 10 and 20 ng/ml). The most significant effects were produced by 10 and 20 ng/ml doses (mean spine numbers=27.5 and 27.0 respectively; n=50 per treatment group; *=p<0.001; df=4/245; F=13.5). A 2.5 ng/ml dose of HGF, however, had no effect on basal spine numbers (mean spine numbers=18.6 vs. control=18.0) (FIG. 8) and was therefore considered to be sub-threshold.

Figure 9A:
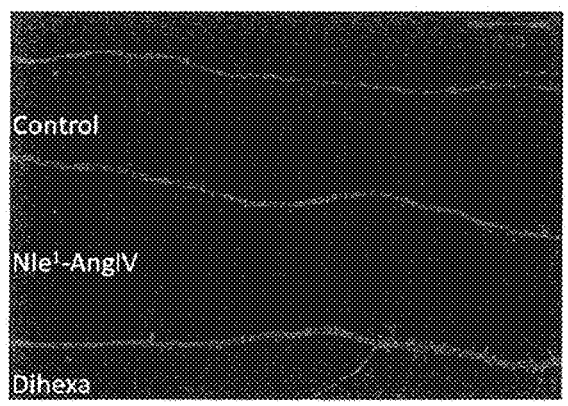
FIGS. 9A and B. Effects of Dihexa and HGF on spinogenesis in organotypic hippocampal slice cultures. Hippocampal slice cultures were biolistically transfected with the red soluble protein Tomato on DIV3 and stimulated with Dihexa or HGF on DIV5. Organotypic hippocampal slice cultures maintain a more intact perforant path and therefore represent a more intact environment. A) Representative images of CA1 neurons, the neuronal type in the hippocampus that exhibits learning associated synaptic plasticity. Hippocampal slices were stimulated with vehicle, $10^{-12}$ M Dihexa, or 10 ng/ml HGF for 2 days. B) Bar graph representing the number of spines per 50 μm dendrite length for each treatment group. Dihexa and HGF significantly increase the number of spines on CA1 hippocampal neurons compared to control treated neurons. ***=$P<0.001$; mean±S.E.M.; n=20 for control, 26 for Dihexa and 38 for HGF stimulated neurons.
Figure 9B:
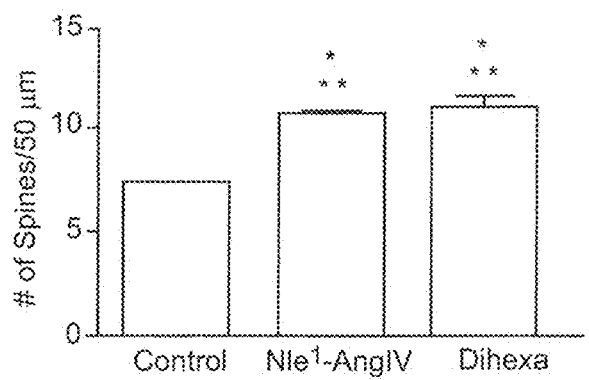

To evaluate the ability of HGF to augment spinogenesis in a more physiologically relevant environment, organotypic hippocampal slices were employed. Hippocampal slices, which were biolistically transfected with the soluble red fluorescent protein Tomato were stimulated with 10 ng/ml HGF, $10^{-12}$ M Dihexa or vehicle for 48 hours. CA1 hippocampal neurons, which are known to undergo plastic changes in response to learning were easily singled out for analysis based on morphology. Dihexa and HGF significantly increased the number of spines per 50 μm dendrite length in the CA1 hippocampal neurons (mean spine numbers=15.0 and 18.5 respectively compared to mean control spine numbers=6.1; *=P<0.001 and =P<0.01 between treatment groups; df=2/81; F=41.5) (FIGS. 9A and B).

Figure 10A:
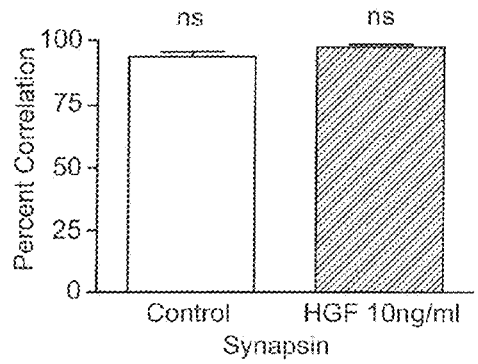
FIG. 10A-D. Effect of HGF treatment on synaptogenesis in dissociated hippocampal neurons. HGF treatment supports the formation of functional synapses as indicated by a high correlation between postsynaptic spines (red) and markers of presynaptic active zones (green). A) Representative images of hippocampal neurons transfected with mRFP-β-actin on DIV6 and treated with 10 ng/ml of HGF or vehicle for 5 days in vitro. The neurons were stained for the general presynaptic marker Synapsin and glutamatergic presynaptic marker VGLUT1. B) Bar graph representing an active phenotype as indicated by a significant increase in the number of spines per 50 μm dendrite length following stimulation with HGF (10 ng/ml). Mean number of spines=33 vs. control=23; ***=$P<0.001$ by one-way ANOVA and Tukey Multiple Comparisons Test; mean±S.E.M.; n=25). C) Percent correlation of actin-enriched postsynaptic spines (red) juxtaposed to the universal presynaptic marker Synapsin (green). A high percent correlation suggests functional synapses are formed. D) Percent correlation of actin-enriched spines (red) juxtaposed to the glutamatergic presynaptic marker VGLUT1 (green). A greater than 95% correlation suggests many of these inputs are glutamatergic.
Figure 10B:
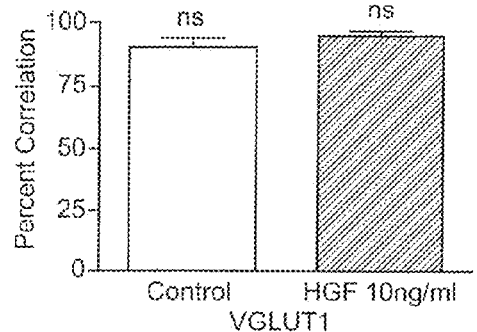
Figure 10C:
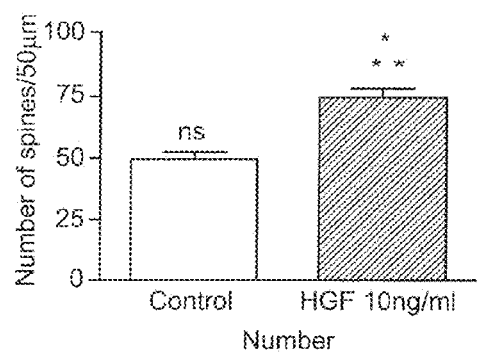
Figure 10D:
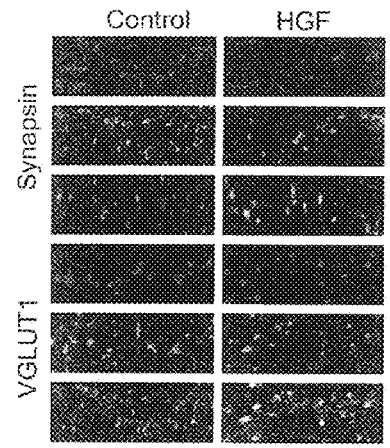

Previous studies in which neurons were treated with Dihexa and Nle1-AngIV indicated that most of dendritic spines that were induced co-localized with both pre- and postsynaptic markers indicated that these new spines supported functional synapses. In addition, the majority of synaptic input appeared to be glutamatergic. Because Dihexa, Nle1-AngIV, and HGF are proposed to all act through a common mechanism, the functional properties of HGF-induced spines was evaluated. mRFP-β-actin transfected hippocampal neurons were immunostained for a general marker of presynaptic active zones, synapsin (Ferreira and Rapoport; 2002) as well as a marker specific to glutamatergic synapses, Vesicular Glutamate Transporter 1 (VGLUT1) (Balschun, Moechars et al. 2010). HGF stimulation significantly augmented the number of postsynaptic spines (mean number of spines per 50 μm dendrite length for HGF=33 vs. 23 for control; *=P<0.001; ±S.E.M. by one-way ANOVA) thus ensuring an active phenotype by HGF-treatment (FIGS. 10A and B). The number of postsynaptic spines adjacent to VGLUT1, or synapsin-positive puncta were counted and converted to a percentage of the total spines counted. For HGF-treated neurons (10 ng/ml) immunostained against Synapsin1 a 98% correlation between the presynaptic marker and postsynaptic actin-enriched spine was observed (FIG. 9C). A 95% correlation for VGLUT1 and postsynaptic spines indicated that spines induced by HGF were almost exclusively glutamatergic (FIG. 10D). The correlation between green puncta and red spines for vehicle treated neurons was similarly 94% for Synapsin and VGLUT1 (FIGS. 10**C and D).

Figure 11:
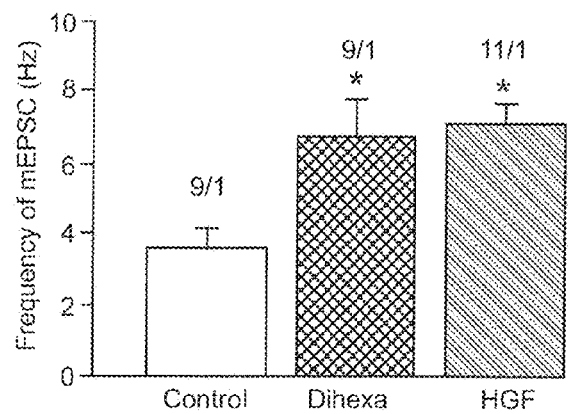
FIG. 11. Effect of Dihexa and HGF treatment on the frequency of mEPSCs in dissociated hippocampal neurons. Dissociated hippocampal neurons transfected with mRFP-β-actin were stimulated with $10^{-12}$ M Dihexa or 10 ng/ml for 5 days prior to recording mEPSCs. Neurons were treated with tetrodotoxin, picrotoxin, and strychnine to suppress action potential, GABA-dependent inhibition, and glycine-dependent inhibition. Treatment with both agonists significantly enhanced AMPA-mediated currents compared to vehicle treated neurons (** $P<0.002$; +S.E.M. by one-way ANOVA followed by Newman-Keuls post hoc test; n=9, 9 and 11 respectively).

The above data suggest that spines produced in response to HGF-treatment form functional synapses. Furthermore, the high correlation with VGLUT1 suggests that many of these inputs are excitatory in nature. To further evaluate this conclusion, we measured the frequency of spontaneous AMPA-mediated mini-excitatory postsynaptic currents (mEPSCs) from neurons following HGF treatment and compared these data to those obtained for Dihexa, which had previously established to increase mEPSC frequency. Recordings were done on dissociated hippocampal neurons transfected with mRFP-β-actin and treated with $10^{-12}$ M Dihexa, 10 ng/ml HGF or an equivalent volume of vehicle for 5 days. Both HGF (mean frequency=7.09±0.53; n=11) and Dihexa treatment (mean frequency=6.75±0.99; n=9) increased excitatory synaptic transmission nearly two-fold over control (mean frequency=3.55±0.60; n=9; =P<0.002; mean±S.E.M. by one-way ANOVA followed by Newman-Keuls post hoc test) treated neurons (FIG. 11**), confirming the supposition that HGF treatment supports increased synaptogenesis.

In order to ascertain whether angiotensin IV ligand actions are mediated by HGF/c-Met a synergy experiment was performed. Sub-threshold doses of HGF augmented with sub-threshold doses of Dihexa or Nle1-AngIV were previously shown to promote spinogenesis, suggesting a common mechanism of action. Dissociated hippocampal neurons transfected with mRFP-β-actin were stimulated for 5 days with sub-threshold concentrations of HGF and Dihexa (2.5 ng/ml+$10^{-13}$ M, respectively), biologically active doses of HGF (10 ng/ml), Dihexa or Nle1-AngIV ($10^{-12}$ M) or a combination of sub-threshold doses of 2.5 ng/ml HGF+$10^{-12}$ M Dihexa or 2.5 ng/ml HGF+$10^{-12}$ M Nle1-AngIV. The results are presented in FIGS. 12A and B. Sub-threshold concentrations of HGF (2.5 ng/ml), Dihexa and Nle1-AngIV ($10^{-13}$ M) had no effect on basal spinogenesis and did not differ from control treated neurons (mean±S.E.M. spine numbers for control=17.4, HGF=16.5, Dihexa=17.1 and Nle1-AngIV=16.5 per 50 μm dendrite length; p>0.05). Biologically active doses of HGF (10 ng/ml), Dihexa and Nle1-AngIV ($10^{-12}$ M) produced a significant effect over control treated spines (mean±S.E.M. spine numbers for HGF=29.3, Dihexa=26.4 and Nle1-AngIV=29.8 per 50 μm dendrite). Combined sub-threshold doses of 2.5 ng/ml+$10^{-13}$ M Dihexa and 2.5 ng/ml+$10^{-13}$ M Nle1-AngIV phenocopied the effects of each agonist at its biologically active dose alone (mean±S.E.M. spine numbers for HGF+Dihexa are 28.8 and HGF+Nle1-AngIV are 26.2 per 50 μm dendrite length compared to control treated neurons 17.4; ***=P<0.001; mean±S.E.M.; by one-way ANOVA followed by Tukey post hoc test).

Figure 12A:
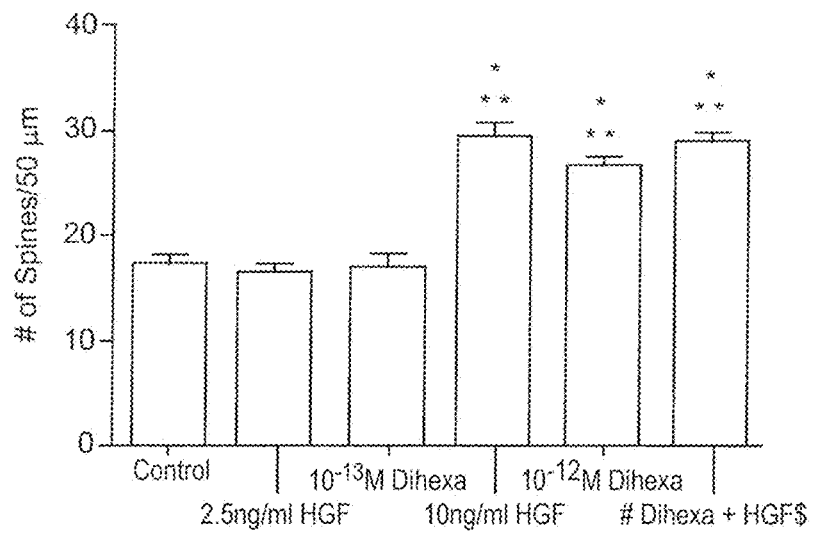
FIGS. 12A and B. Effect of maximal and sub-threshold doses of Angiotensin IV analogues and HGF on spinogenesis. A) Sub-threshold levels of HGF, Dihexa or Nle1-AngIV do not affect basal spine numbers. Combined sub-threshold levels of Dihexa ($10^{-13}$ M) and HGF (2.5 ng/ml) phenocopy the effects of Dihexa at its biologically effective dose alone; #=$10^{-13}$ M and $=2.5 ng/ml. B) A sub-threshold dose of the parent compound Nle1-Ang IV ($10^{-13}$ M) also does not affect basal spine levels. Combined sub-threshold levels of Dihexa ($10^{-13}$ M) and HGF (2.5 ng/ml) phenocopy the effects of Nle1-AngIV at its biologically effective dose alone; #=$10^{-13}$ M and $=2.5 ng/ml. The ability of combined agonists at sub-threshold doses to generate maximal responses suggests a commonality of receptor pathways. *** $P<0.001$; mean±S.E.M.; n=50.
Figure 13A:
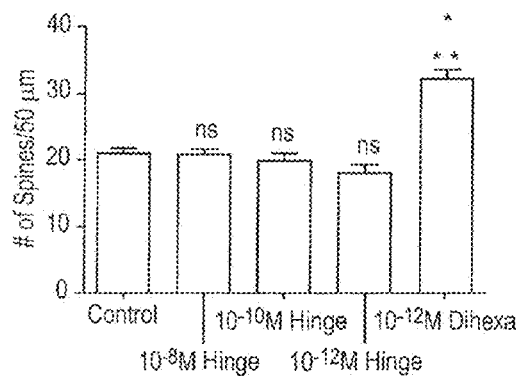
FIG. 13A-D. The effect of the novel HGF antagonist Hinge on angiotensin IV ligand- and HGF-mediated spinogenesis. A) The effects of the HGF antagonist Hinge ($10^{-12}$ M) on spinogenesis were evaluated. Hinge does not affect spinogenesis in neurons over a wide range of doses; Dihexa was included to ensure the neurons were responsive to treatment. B) Hinge inhibits HGF— induced spinogenesis C) Hinge inhibits Nle1-AngIV-induced spinogenesis D) Hinge inhibits Dihexa-induced spinogenesis. #=$10^{-12}$ M and $=10 ng/ml. The above data further indicate that the actions of Nle1-AngIV and Dihexa are mediated by the HGF/c-Met system. *** $P<0.001$; mean±S.E.M.; n=50.
Figure 13B:
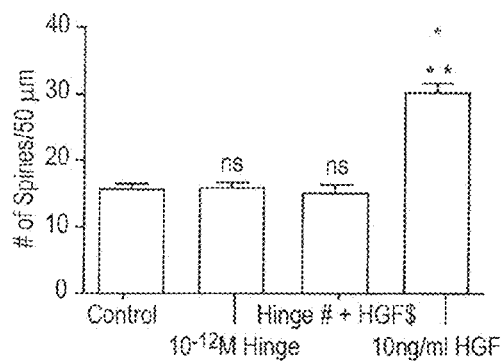
Figure 13C:
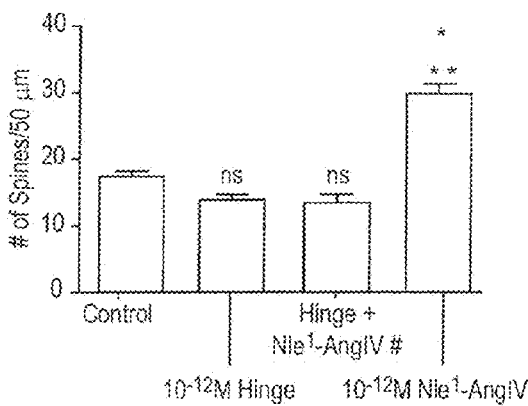
Figure 13D:
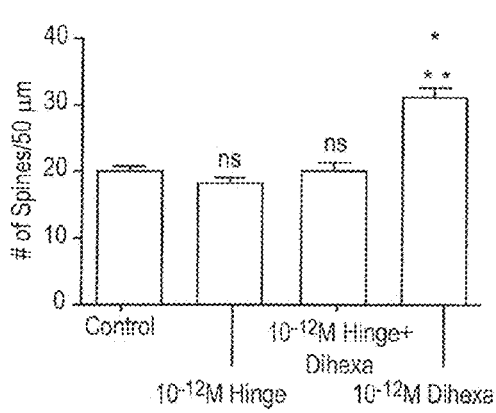

Seeking further substantiation for angiotensin IV ligand and HGF/c-Met mediated interactions, the novel HGF antagonist Hinge (DYIRNC, SEQ ID NO: 3) was utilized (Kawas et al., 20113 Hinge was confirmed as an HGF/c-Met receptor antagonist by its ability to inhibit scattering of Madin-Darby canine kidney (MDCK) cells, the gold standard for assessment of c-Met mediated activity. Cell scattering involves a loss of cell adhesion properties, cell migration and differentiation, the hallmarks of HGF and c-Met actions (Yamamoto, Elias et al., 2010; Birchmeier, Sonnenberg et al. 1993). Hinge was tested for its effects on dissociated hippocampal neurons and was found to have no effect on spinogenesis over a wide range of doses, thus indicating that Hinge and the HGF/c-Met system do not have a significant role in the basal spinogenesis seen in the cultured neurons (FIG. 13A). However, Hinge did effectively inhibit spine formation in neurons stimulated with 10 ng/ml HGF (FIG. 13B), $10^{-12}$ M Nle1-AngIV (FIG. 13C) or $10^{-12}$ M Dihexa (FIG. 12D) further supporting the contention that these actions are mediated by the HGF/c-Met system.

Figure 14A:
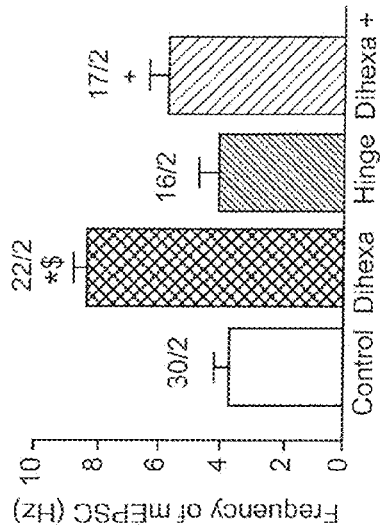
FIG. 14A-D. Effect of the HGF antagonist Hinge on HGF- and Dihexa-mediated enhancement of mEPSCs in dissociated hippocampal neurons. Dissociated hippocampal neurons were treated with Hinge ($10^{-12}$ M), HGF, Dihexa ($10^{-12}$ M) or HGF (10 ng/ml) for 5 days after at which time mEPSCs were recorded in the absence of action potentials. A) Representative traces of a Hinge treated neuron. B) Representative trace of a vehicle treated neuron. C) HGF significantly augments AMPA-mediated frequencies compared to control treated neurons. This effect is attenuated by Hinge while alone Hinge has no effect. D) Spontaneous AMPA-mediated frequencies are significantly increased following treatment with Dihexa and significantly reduced following pre-treatment with Hinge, which alone has no effect on base-line frequencies. * $P<0.001$; mean±S.E.M. by one way ANOVA followed by Newman-Keuls post hoc test.
Figure 14B:
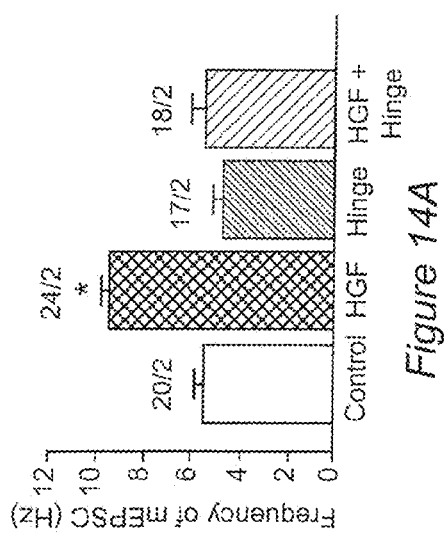
Figure 14C:
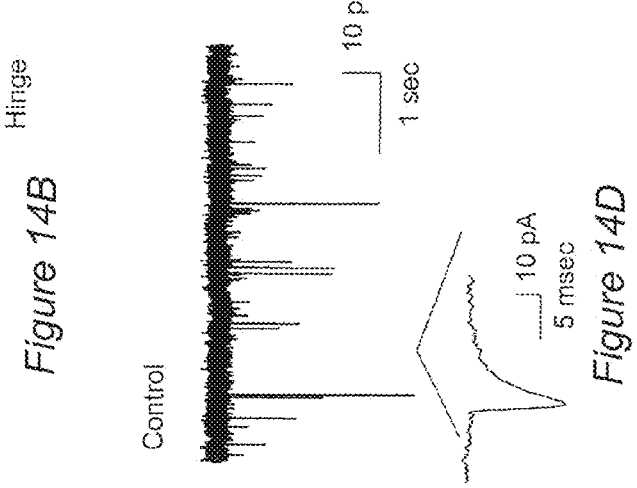
Figure 14D:
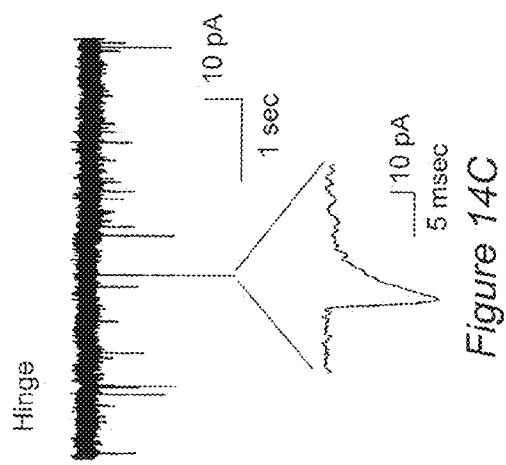

To assess the effects of Hinge on excitatory synaptic transmission mEPSCs were recorded form mRFP-β-actin transfected hippocampal neurons treated for 5 days with Hinge ($10^{-12}$ M), HGF (10 ng/ml), Dihexa ($10^{-12}$ M), Hinge+HGF ($10^{-12}$ M+10 ng/ml, respectively) or Hinge+Dihexa ($10^{-12}$ M each). Hinge alone does not affect synaptic transmission (mean frequency=4.51±0.47) compared to vehicle treated neurons (mean frequency=5.31±0.35; FIGS. 14A and B). HGF and Dihexa frequencies were significantly increased compared to both Hinge and vehicle treated neurons (mean frequency for HGF=9.66±0.20 and for Dihexa=8.25±0.56). However these effects are significantly attenuated by stimulation in the presence of Hinge (mean frequencies for HGF+Hinge=5.25±0.27 and Dihexa+Hinge=5.57±0.65; FIGS. 14A and B). These results suggest that the newly generated spines are forming functional synapses and while Hinge has no effect on synaptic transmission, it is its ability to inhibit spinogenesis that attenuates the AMPA-mediated frequencies.

Figure 15A:
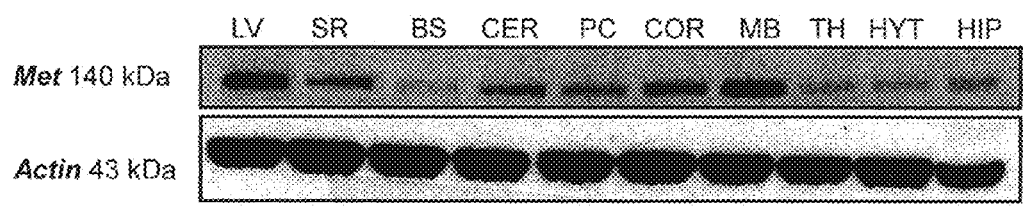
FIG. 15A-B. Distribution of c-Met protein in the adult rat brain. Gross brain regions were obtained from adult Sprague-Dawley rats and acutely frozen in liquid nitrogen. The samples were homogenized, separated by electrophoresis and immunoblotted for c-Met protein and actin. A) The bar graph represents the amount of c-Met (unspecified units) in distinct brain regions of importance to cognition. The brain samples were compared to liver where HGF is produced. B) A representative Western blot of the samples probed against c-Met protein (bands are at 145 kDa) and actin serving as a loading control. Equal amounts of protein were loaded in each lane based on BCA protein determinations.
Figure 15B:
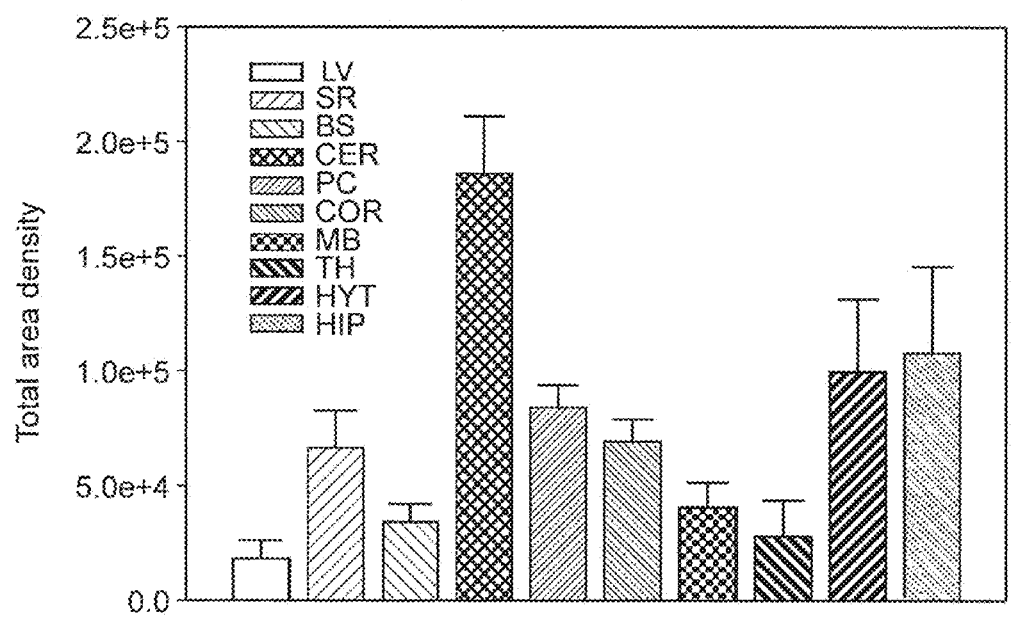

The proposed angiotensin IV receptor HGF is the ligand for the tyrosine kinase receptor c-Met. Although the localization of c-Met and HGF mRNA in the brain has been well documented (Jung, Castren et al. 1994; Honda, Kagoshima et al. 1995; Thewke and Seeds 1996; Achim, Katyal et al. 1997) the presence and distribution of c-Met protein has not been examined. Therefore we probed several brain regions for the presence of c-Met but were unable to do so for HGF due to a lack of effective antibodies. High levels of c-Met protein were observed throughout most of the brain regions. Specifically, the highest signal of c-Met protein was seen in the hippocampus and appears to be greater than in the liver which is a major site of HGF production. A strong signal was also observed in the prefrontal cortex and midbrain, regions of importance to cognition, while neocortex had a somewhat attenuated signal the cerebellum produced the lowest signal (FIGS. 15A and B).

Figure 16:
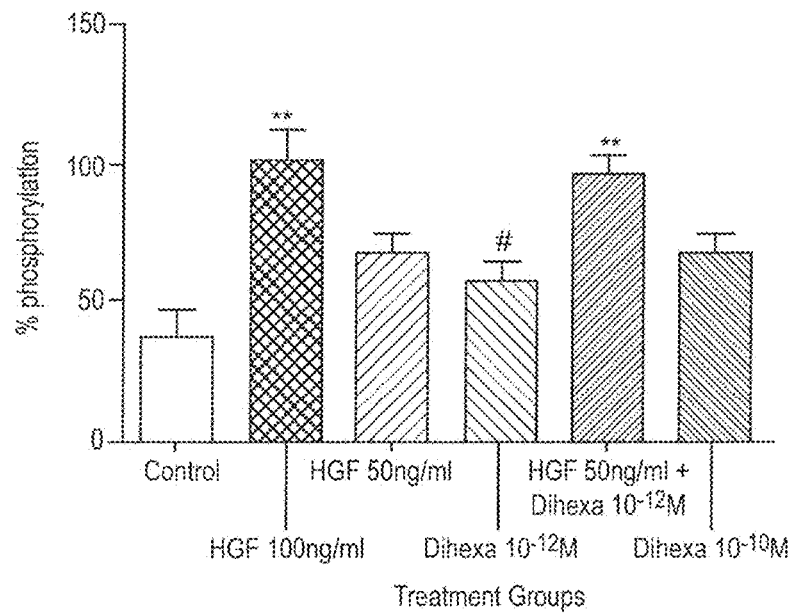
FIG. 16. Stimulation of c-Met phosphorylation by HGF and Dihexa in rat hippocampal slices. To test whether Dihexa could activate the c-Met receptor in the adult rat brain, hippocampal slices were acutely stimulated for 30 minutes with HGF, Dihexa or vehicle (aCSF). Receptor activation was measured by phosphorylation of the c-Met receptor by Western blot. Saturating doses of HGF (100 ng/ml) and Dihexa ($10^{-10}$ M) effectively augment c-Met phosphorylation in acutely stimulated adult hippocampal slices compared to vehicle treated slices. Sub-threshold doses of HGF (50 ng/ml) and Dihexa ($10^{-12}$ M) did not significantly increase c-Met receptor phosphorylation compared to control. However, combined sub-threshold doses of HGF and Dihexa phenocopied the saturating doses of HGF and Dihexa.
Figure 17:
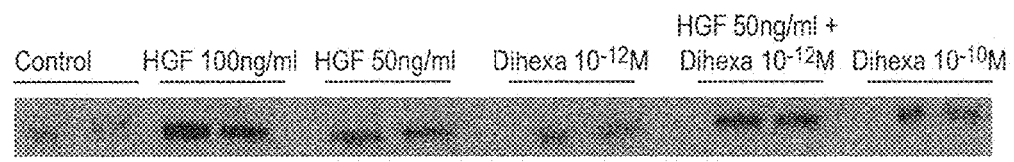
FIG. 17. Effect of the HGF mimetic, Dihexa, on c-Met activation. HEK 293 cells were treated with HGF+/−Dihexa at various doses, incubated at 37° C. for 30 minutes, and then analyzed for phosphorylated (activated) c-Met by immunoblotting. The results clearly demonstrate the ability of HGF and Dihexa to work synergistically to activate c-Met.
Figure 18:
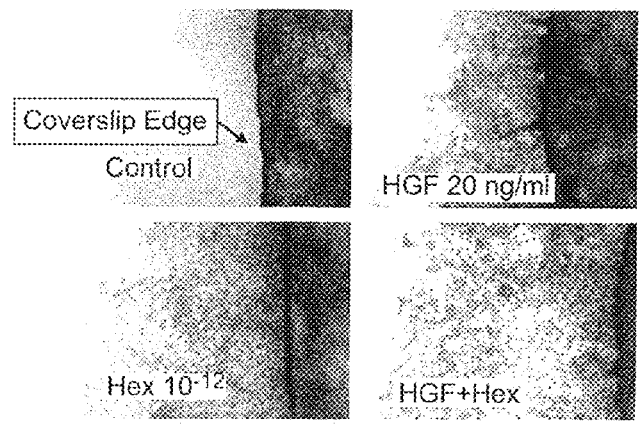
FIG. 18. Effect of the HGF mimetic, Dihexa, HGF-dependent cell scattering. Cell scattering was assessed in MDCK cells. Cells were grown to confluence on coverslips, which were then transferred to a clean plate. After treatment for four days, the number of cells that had scattered off the coverslip was quantitated. HEX=Dihexa at $10^{-10}$ M.

The apparent dependency of the actions of Dihexa on the HGF/c-Met system predicted that Dihexa in the presence of sub-threshold levels of HGF should be able to stimulate c-Met phosphorylation and activation. Therefore acute adult rat hippocampal slices were stimulated with HGF, Dihexa at saturating and non-saturating concentrations alone and in combination and probed for phospho-Met. Phosphorylation of the c-Met receptor indicates receptor activation. FIG. 16 shows phosphorylation of the c-Met receptor following a 30 minute treatment with vehicle and various concentrations HGF or Dihexa. Saturating doses of HGF (100 ng/ml) and Dihexa ($10^{-10}$ M) Dihexa both increased c-Met phosphorylation compared to control (aCSF) treated slices; ($p<0.007$). Non-saturating doses of HGF (50 ng/ml) and Dihexa ($10^{-12}$ M) were not statistically different from control treated slices ($p>0.05$) and therefore considered to be sub-threshold. The sub-threshold doses of HGF and Dihexa combined, however, appeared to produce an effect similar to the saturating doses of HGF and Dihexa ($p<0.007$). Thus dependent on the dose it appears that Dihexa is independently capable of activating the HGF/c-Met system in the adult rat brain alone as well as in conjunction with HGF. In concert with these findings Dihexa able to dramatically augment the ability of HGF to activate c-Met by phosphorylation in HEK293 cells (FIG. 17) and stimulate MDCK cell scattering (FIG. 18).

Figure 19:
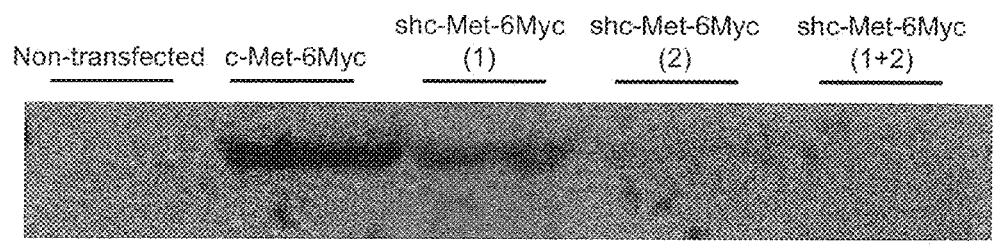
FIG. 19. Verification of c-Met receptor knockdown. Receptor knockdown was confirmed by transfecting HEK cells with mRFP-β-actin (untransfected), a 6Myc-tagged cMet gene product that served to verify presence of protein, shRNA (c-Met) sequences (only sh1 was employed for the knockdown experiment) and both shRNA's combined. The transfected cells were cultured for a further 24 hours then lysed with RIPA buffer and prepared for gel electrophoresis. The samples were probed against Myc by Western blot. Untransfected cells serving as the negative control showed no signal, the 6-Myc-tagged cMet gene product was the positive control and had a strong signal. Both the shMet1 and shMet2 sequences considerably attenuated the signal and combined did not have a signal indicating effective knock down of the receptor.

To irrefutably confirm that the AngIV analogues act via the HGF/c-met system an shRNA for c-Met was employed to knock-down the receptor. Dissociated hippocampal neurons were transfected with mRFP-β-actin and shMet RNA and receptor knock-down was allowed to take place for 48 hours prior to stimulating with 0.5 μg (per well) HGF (10 ng/ml), Dihexa or Nle1-AngIV (both at $10^{-12}$ M). Longer exposure appeared to be detrimental or toxic to the neurons. Effective c-Met receptor knock-down was verified by transfecting human embryonic kidney (HEK) cells with (0.1 μg) 6-Myc-tagged c-Met, (0.1 μg) shMet or mRFP-β-actin alone. Successful knockdown was confirmed by immunoblotting for Myc tagged c-met using an anti-Myc antibody (FIG. 19).

Figure 20:
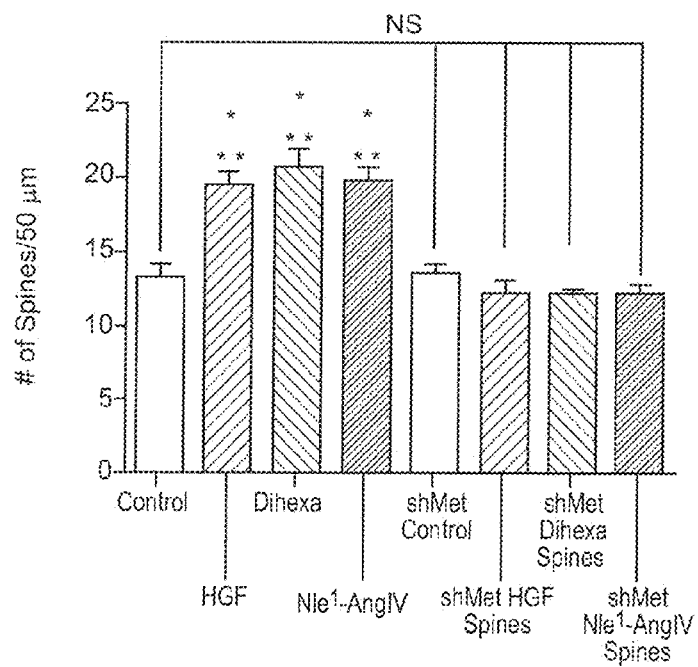
FIG. 20. Effect of c-Met knock-down on spinogenesis using a shRNA. The picture shows a Western blot probed for Myc. Hippocampal neurons transfected with mRFP-β-actin alone or with shMet to knock down the c-Met receptor were stimulated with HGF (10 ng/ml), Dihexa (10-12 M) or Nle1-AngIV (10-12 M) for 48 hours. Neurons transfected with mRFP-13-actin and stimulated with HGF, Dihexa or Nle1-AngIV significantly increased spinogenesis (* $P<0.05$; mean±S.E.M.; n=100). Those neurons transfected with mRFP-β-actin and shMet did not respond to stimulation with HGF, Dihexa or Nie1-AngIV treatment, confirming HGF and c-Met are the target ($P>0.05$; mean±S.E.M.; n=100).

Neurons transfected with mRFP-β-actin alone, serving as the control, were treated with 10 ng/ml HGF, $10^{-12}$ M Dihexa or Nle1-AngIV. A significant increase in the number of spines compared to control treated neurons was observed (mean spine numbers per 50 dendrite length=13.2 vs HGF=20.6; Dihexa=21.8 and Nle1-AngIV=20.0; $p<0.05$ by one-way ANOVA followed by Tukey post hoc test). Neurons transfected with mRFP-β-actin and shMet that were stimulated with 10 ng/ml HGF, $10^{-12}$ M Dihexa or Nle1-AngIV, did not differ from control in terms of spine numbers (mean spine numbers per 50 μm dendrite length=13.5 vs HGF=12.4; Dihexa=12.0 and Nle1-AngIV=12.1; $p>0.05$ by one-way ANOVA followed by Tukey post hoc test) as shown in FIG. 20. A scrambled RNA sequence was employed as the negative control and had no effect on basal or stimulated spinogenesis (data not shown). These results confirm that the effects of AngIV analogs are mediated by the HGF/c-Met system.

Figure 21:
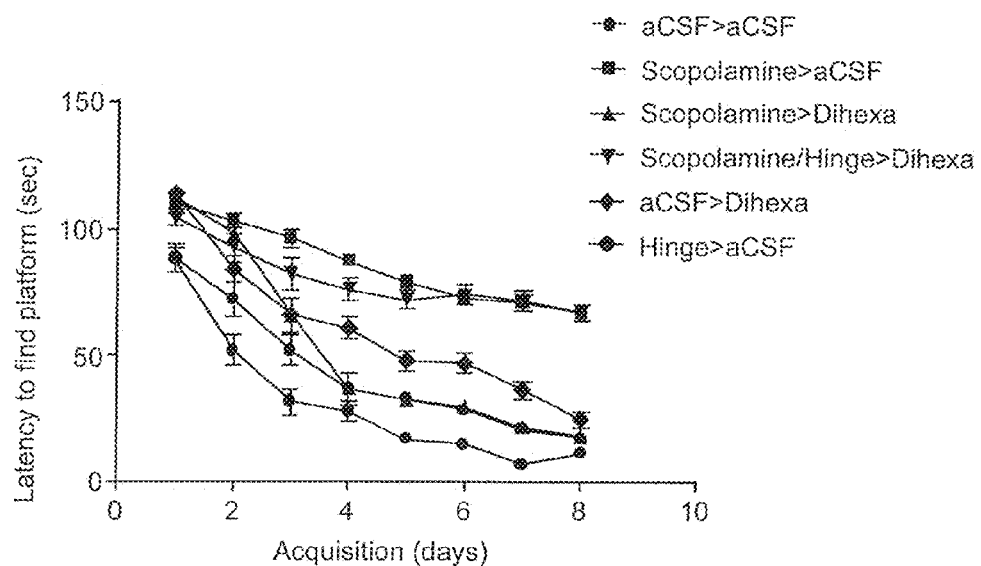
FIG. 21. HGF and c-Met have a function in spatial learning and memory. The latency to locate a submerged pedestal in the Morris water maze task of spatial learning and memory was tested on rats to ascertain the effects of HGF/c-Met on learning and memory. Rats received i.c.v. injections of amnestic drugs or HGF/c-Met receptor agonists. Rats treated with the scopolamine→scopolamine are unable to learn the task as measured by latency to escape. The group latencies for rats treated with aCSF→aCSF were significantly shorter than the scopolamine treated group on day one of training. Scopolamine→Dihexa treated rats and rats treated with Hinge→Hinge, while not significantly different from the scopolamine treated group on day one of training show rapid facilitation of the task. The group that received scopolamine+ Hinge→Dihexa was not significantly different from the scopolamine treated animals and has long latencies to escape. Group latencies to locate a submerged pedestal in the Morris water maze task of spatial learning and memory. Hinge alone has no effect on learning; however Hinge in addition to scopolamine prevents facilitation of the task.

The Morris water maze, a hippocampal-dependent spatial learning task requiring rats to locate a pedestal hidden beneath the surface of the water by orienting themselves to extra-maze cues was employed to evaluate the impact of the HGF antagonist, Hinge, on the pro-cognitive effects of Dihexa. The groups tested included aCSF followed by aCSF, scopolamine (70 nM) followed by aCSF, scopolamine followed by Dihexa (300 pM), aCSF followed by Hinge (300 pM) and scopolamine+Hinge followed by Dihexa. FIG. 21 represents the mean latencies to find the hidden pedestal for days 1-8 of training in the water maze. None of the groups differed significantly in latency to find the pedestal on day one of training. Mean latencies for the vehicle control (aCSF→aCSF) group=89.3 s; the scopolamine treated group=114.7 s; the scopolamine+Hinge→4 Dihexa treated group latency=107.9 s; the Hinge group mean latency=111.1 s; and the scopolamine→Dihexa group=115.2 s. By the fourth day of training, considered to be a crucial day on which the most improvement in training and neural plasticity occurs (Meighan et al., 2006), the scopolamine group (mean latency to find the pedestal=102.4 s) and the scopolamine+Hinge→Dihexa group (mean latency=105.2 s) showed no signs of improvement compared to the vehicle control group (mean latency=43.0 s), the Hinge group (mean latency=78.3 s) and the scopolamine→Dihexa group (mean latency=63.0 s). On the final day of training when maximal learning has occurred (Meighan, Meighan et al. 2006) the mean latencies for the scopolamine group (mean latency to find the pedestal=84.8 s) and the scopolamine+Hinge→Dihexa group (mean latency=93.6 s) indicated little improvement in learning compared to the vehicle control group (mean latency=43.0 s), the Hinge group (mean latency=46.1 s) and the scopolamine→Dihexa group (mean latency 62.3 s). These results suggest that HGF and c-Met play an important role in hippocampal-dependent cognitive processes.

Discussion

The pro-cognitive effects of angiotensin IV analogues suggest that anti-dementia drugs based on this system can be developed (Braszko, Kupryszewski et al. 1988; Stubley-Weatherly, Harding et al. 1996; Pederson, Harding et al. 1998; Wright, Stubley et al. 1999). However, due to poor metabolic stability of angiotensin IV and many AngIV analogues, the inability of early analogues to penetrate the blood brain barrier, and the failure to identify the AT4 receptor, no pharmaceutical company has moved forward with their development. Dihexa, a novel angiotensin IV analogue synthesized by our laboratory, is stable and orally active and has thus overcome the major pharmacokinetic impediments preventing development. Dihexa has been proven to be stable in the blood for over 5 hours (not shown), survived passage through the gut to penetrate the blood brain barrier, and overcomes cognitive deficits in acute and chronic models of dementia (not shown). A general mechanism, established for facilitation of the water maze task, involves expansion of the dendritic arbor in the form of newly developed postsynaptic spines and accompanying synaptogenesis. The last remaining hurdle to development was the lack of a molecular mechanism.

Here we demonstrate that the actions of AngIV analogues are dependent on the HGF/c-Met system. Both systems appear to mediate similar physiological effects. The Angiotensin IV/AT4 system has cerebroprotective effects (Wright, Clemens et al. 1996; Date, Takagi et al. 2004), augments long term potentiation (Kramar, Armstrong et al. 2001; Wayner, Armstrong et al. 2001; Akimoto, Baba et al. 2004; Davis, Kramar et al. 2006), has well established pro-cognitive effects (Wright and Harding 2008), and is suspected to regulate neural stem cell development. The HGF/c-Met system also has pro-cognitive effects (Akimoto, Baba et al. 2004; Tyndall and Walikonis 2006; Tyndall and Walikonis 2007) and is known to be involved in stem cell regulation (Urbanek, Rota et al. 2005; Nicoleau, Benzakour et al. 2009). In addition to functional similarities there is sequence homology between angiotensin IV and the "hinge" linker region of HGF (Wright, Yamamoto et al. 2008). This notion was further solidified by the observation that the well known AT4 antagonist, Norleual, is capable of blocking many HGF/c-Met regulated functions such as MDCK cell scattering (Yamamoto, Elias et al. 2010).

Facilitation of the water maze task is effected by Dihexa and the parent angiotensin IV ligand, Nle1-AngIV, by augmentation of neurotransmission occurring through elaboration of the dendritic arbor. The hypothesized linkage between the action of AngIV analogues and the HGF/c-Met system predicted that like Dihexa and Nle1-AngIV HGF should be able to stimulate dendritic spine growth in dissociated hippocampal neurons. As predicted, HGF promoted a dose-dependent increase in spinogenesis (FIG. 7) in dissociated hippocampal neurons. The most effective concentration of HGF (10 ng/ml) was subsequently found to stimulate hippocampal neurons in organotypic hippocampal slice cultures which are more intact preparations similar to Dihexa (FIGS. 8A and B) further establishing a mechanistic link between Dihexa and HGF/c-Met. To evaluate the physiological relevance of these new spines and to determine the neurotransmitter signature of resident synapses, HGF treatment-induced spines labeled with mRFP-β-actin were immunostained for the universal presynaptic marker Synapsin that is located in the presynaptic active zones (Ferreira and Rapoport 2002) and the excitatory presynaptic marker VGLUT1 that is found at glutamatergic presynaptic synapses (Balschun, Moechars et al.). The ratio of postsynaptic mRFP-β-actin labeled spines juxtaposed to Synapsin or VGLUT1 spines was not different from control treated neurons suggesting treatment-induced spines are forming functional synapses (FIG. 9A-D). Further validation of synaptogenesis was obtained by recording mEPSCs, spontaneous presynaptic bursts independent of action potentials, on HGF and Dihexa treated neurons. AMPA-mediated transmission was amplified in response to HGF and Dihexa treatment as shown by increased frequencies (FIG. 10).

Sub-threshold concentrations of Dihexa and HGF or Nle1-AngIV and HGF were used to stimulate hippocampal neurons in vitro to determine whether the angiotensin IV ligands Dihexa and Nle1-AngIV, and HGF affect the same signaling cascade or act on one receptor (c-Met). To determine whether Dihexa and Nle1-AngIV engage the same signaling cascade sub-threshold concentrations of AngIV ligands were combined with sub-threshold doses of HGF. While sub-threshold concentrations of each ligand alone did not alter basal spinogenesis, combined sub-threshold concentrations of $10^{-13}$ M Dihexa and 2.5 ng/ml HGF or $10^{-13}$ M Nle1-AngIV and 2.5 ng/ml of HGF produced a near ceiling effect, similar to biological responsive doses of each ligand alone (FIGS. 11A and B). The similarities in the dendritic responses to the AngIV analogues and HGF are consistent with a common mechanism of action.

Figure 12B:
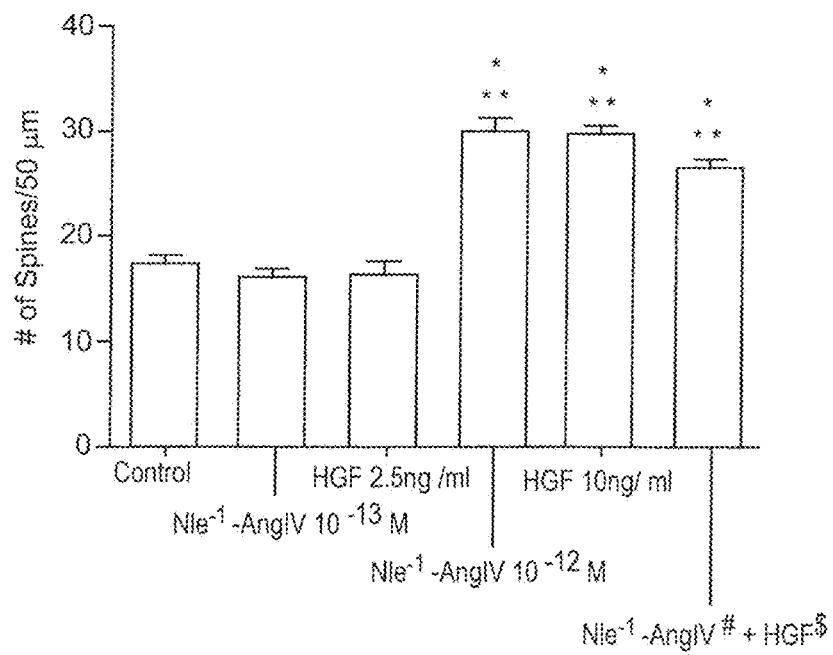

To further strengthen this perceived commonality of mechanism, the novel HGF antagonist Hinge was employed and evaluated for its effects on hippocampal neurons stimulated with AngIV analogues and HGF. Hinge, like the angiotensin IV antagonist Norleual, was established as a c-Met antagonist by its ability to block HGF-dependent c-Met phosphorylation and prevent HGF-dependent scattering in the MDCK epithelial cell line. Cell scattering, which is the hallmark of an HGF/c-Met interaction, leads to a loss of cell adhesion properties that allow cells to migrate (Yamamoto, Elias et al.; Birchmeier, Sonnenberg et al. 1993). Hinge was found to have no adverse effects on cultured hippocampal neurons and did not promote or hinder spinogenesis (FIG. 12A). At pico molar concentrations, however, Hinge prevented HGF, Nle 1-AngIV and Dihexa induced spinogenesis (FIG. 12B-D) further suggesting that the effects observed for our angiotensin IV ligands are HGF/c-Met mediated. The effects of Hinge on synaptogenesis were evaluated by recording mEPSC frequencies on cultured hippocampal neurons. While Hinge alone did alter base-line synaptic transmission it attenuated HGF and Dihexa increases in AMPA-frequencies (FIGS. 13A and B). This effect was likely due to attenuation of spinogenesis promoted by HGF and Dihexa treatments since, without the antagonizing effect of Hinge, each agonist increased mini-AMPA frequencies (FIGS. 13A-B and FIG. 10) thus forming functional synaptic connections. Taken together, these data suggest that inhibiting HGF does not alter the number of functional synapses in vehicle treated neurons but attenuates the effects of HGF and Dihexa on synaptogenesis by decreasing the number of postsynaptic spines.

To additionally support the contention that the agonists Dihexa and Nle1-AngIV are acting through HGF and its receptor c-Met, hippocampal neurons were transfected with shRNA to knockdown the c-Met receptor. Knockdown of the receptor was verified by immunoblotting against a Myc-tagged c-Met gene product (FIG. 16). As expected, stimulation of hippocampal neurons transfected with mRFP-β-actin with HGF, Dihexa and Nle1-AngIV had significantly enhanced dendritic arbors while those additionally transfected with she-Met RNA were no different from control treated neurons (FIG. 17). These data provide conclusive support for our belief that angiotensin IV ligands Dihexa and Nle1-AngIV act through the HGF/c-Met system.

The newly developed angiotensin IV agonist ligand Dihexa has been shown to facilitate acquisition of a spatial learning and memory task in scopolamine treated rats (data not shown). Because it is prohibitively expensive to test HGF in the water maze, we instead evaluated its involvement in cognition by employing the HGF antagonist Hinge to block the actions of Dihexa. Treatment with the muscarinic cholinergic receptor antagonist scopolamine renders rats acutely amnesic and therefore unable to learn the task. A rescue effect is observed in rats that are given Dihexa following scopolamine pretreatment. These rats exhibit rapid facilitation of the task and did not perform differently from vehicle treated rats. The group of rats that was pretreated with a scopolamine and Hinge did not display the rescue effect observed by Dihexa in the scopolamine preparation (FIGS. 14A and B). These data demonstrate a function for HGF and c-Met system in learning and memory, and that agents which mimic the action of HGF can be used to enhance learning and memory in subjects in need thereof.

Example 3

Development of Antiotensin IV Analogs as Hepatocyte Growth Factor/Met Modifiers The 6-AH family [D-Nle-X-Ile-NH—($CH_2$)$_5$—$CONH_2$; where X=various amino acids] of Angiotensin IV analogs, bind directly to Hepatocyte Growth Factor (HGF) and inhibit HGF's ability to form functional dimers. The metabolically stabilized 6-AH family member, D-Nle-Tyr-Ile-NH—($CH_2$)$_5$—$CONH_2$, had a $t_{1/2}$ in blood of 80 min compared to the parent compound Norleual (Nle-Tyr-Leu-$\Psi$-($CH_2$—$NH_2$)$^{3\text{-}4}$-His-Pro-Phe, SEQ ID NO: 1), which had a $t_{1/2}$ in blood of <5 min. 6-AH family members were found to act as mimics of the dimerization domain of HGF (hinge region), and inhibited the interaction of an HGF molecule with a $^3$H-hinge region peptide resulting in an attenuated capacity of HGF to activate its receptor Met. This interference translated into inhibition of HGF-dependent signaling, proliferation, and scattering in multiple cell types at concentrations down into the low picomolar range. We also noted a significant correlation between the ability of the 6-AH family members to block HGF dimerization and inhibition of the cellular activity. Further, a member of the 6-AH family with cysteine at position 2, was a particularly effective antagonist of HGF-dependent cellular activities. This compound suppressed pulmonary colonization by B16-F10 murine melanoma cells, which are characterized by an overactive HGF/Met system. Together these data indicate that the 6-AH family of AngIV analogs exert their biological activity by modifying the activity of the HGF/Met system and offer the potential as therapeutic agents in disorders that are dependent on or possess an over-activation of the HGF/Met system.

INTRODUCTION

The multifunctional growth factor hepatocyte growth factor (HGF) and its receptor Met are important mediators for mitogenesis, motogenesis, and morphogenesis in a wide range of cell types (Birchmeier et al., 2003) including epithelial (Kakazu et al., 2004), endothelial (Kanda et al., 2006), and hematopoietic cells (Ratajczak et al., 1997), neurons (Thompson et al., 2004), melanocytes (Halaban et al., 1992), and hepatocytes (Borowiak et al., 2004). Furthermore, dysregulation of the HGF/Met system often leads to neoplastic changes and to cancer (in both human and animal) where it contributes to tumor formation, tumor metastasis, and tumor angiogenesis (Christensen et al., 2005; Liu et al., 2008). Over-activation of this signaling system is routinely linked to poor patient prognosis (Liu et al., 2010). Therefore molecules that inhibit the HGF/Met system can be expected to exhibit anti-cancer activity and attenuate malignant and metastatic transformations.

HGF is a vertebrate heteromeric polypeptide growth factor with a domain structure that closely resembles the proteinases of the plasminogen family (Donate et al., 1994). HGF consists of seven domains: an amino terminal domain, a dimerization-linker domain, four kringle domains (K1-K4), and a serine proteinase homology (SPH) domain (Lokker et al., 1992; Chirgadze et al., 1999). The single chain pro-polypeptide is proteolytically processed by convertases to yield a mature a (heavy chain 55 KDa), and β (light chain 34 KDa) heterodimer, which are bound together by a disulfide link (Stella and Comoglio, 1999; Birchmeier et al., 2003; Gherardi et al., 2006). In addition to proteolytic processing, HGF requires dimerization to be fully activated (Lokker et al., 1992; Chirgadze et al., 1999; Youles et al., 2008). Several reports have shown that HGF fauns dimers and/or multimers, which are arranged in a head-to-tail orientation, prior to its interaction with Met (Gherardi et al., 2006). The dimer interface, which encompasses the inter-domain linker amino acids (K122, D123, Y124, I125, R126, and N127) is referred to as the hinge region (Gherardi et al., 2006; Youles et al., 2008). Although both pre-pro-HGF and the active disulfide-linked heterodimer bind Met with high affinity, it is only the heterodimer that is capable of activating Met (Lokker et al., 1992; Sheth et al., 2008).

Recent studies from our laboratory (Yamamoto et al., 2010) have shown that picomolar concentrations of the AngIV analog, Norleual (Nle-Tyr-Leu-ψ-($CH_2$—$NH_2$)$^{3\text{-}4}$-His-Pro-Phe), are capable of potently inhibiting the HGF/Met system and bind directly to the hinge region of HGF blocking its dimerization (Kawas et al., 2011). Moreover, a hexapeptide representing the actual hinge region possessed biochemical and pharmacological properties identical to Norleual's (Kawas et al., 2011). The major implication of those studies was that molecules, which target the dimerization domain of HGF, could represent novel and viable anti-cancer therapeutics. Additionally, these data support the development of such molecules using Norleual and/or the Hinge peptide as synthetic templates.

Despite its marked anti-cancer profile Norleual is highly unstable making its transition to clinical use problematic. Thus a family of metabolically stabile Ang IV-related analogs has been developed in our laboratory, which are referred to here as the 6-AH family because of 6-amnio hexanoic amide substituted at the C-terminal position. This substitution along with D-norleucine at the N-terminal enhances the metabolic resistance of family members.

In this Example 3, it is demonstrated that 6-AH family members (i.e., HGF Mimics) have superior metabolic stability when compared to Norleual, bind to HGF with high affinity, and act as hinge region mimics; thus preventing HGF dimerization and activation. This interference translates into inhibition of HGF-dependent signaling, proliferation, and scattering in multiple cell types at concentration in the picomolar range. A positive correlation was evident between the ability to block dimerization and the inhibition of the cellular outcomes of HGF activation. Finally D-Nle-Cys-Ile-NH—($CH_2$)$_5$—$CONH_2$, a member of the 6-AH family suppressed pulmonary colonization by B16-F10 murine melanoma cells, which are characterized by an overactive HGF/Met system. This Example highlights the ability of AngIV-like molecules to bind to HGF, block HGF dimerization, and inhibit the HGF/Met system. Moreover, these HGF mimics have utility as AngIV-related pharmaceuticals and can function as therapeutic agents in disorders where inhibition of the HGF/Met system would be clinically advantageous.

Material and Methods

Animals.

C57BL/6 mice from Taconic farms were used in the lung colonization studies. Male Sprague-Dawley rats (250+ g) were obtained from Harlan Laboratories (CA, USA) for use in pharmacokinetic studies. Animals were housed and cared for in accordance with NIH guidelines as described in the "Guide for the Care and Use of Laboratory Animals"

Compounds.

D-Nle-X-Ile-NH—($CH_2$)$_5$—COOH; where X=various amino acids and Norleual (Nle-Tyr-Leu-ψ-($CH_2$—$NH_2$)$^{3\text{-}4}$-His-Pro-Phe, SEQ ID NO: 1) were synthesized using Fmoc based solid phase methods in the Harding laboratory and purified by reverse phase HPLC. Purity and structure were verified by LC-MS. Hepatocyte growth factor (HGF) was purchased from R&D Systems (Minneapolis, Minn.).

Antibodies.

Anti-Met was purchased from Cell Signaling Technology (Beverly, Mass.) and the phospho-Met antibody was purchased from AbCam, Inc (Cambridge, Mass.).

Cell Culture.

Human embryonic kidney cells 293 (HEK293) and Madin Darby canine kidney cells (MDCK) were grown in DMEM, 10% fetal bovine serum (FBS). Cells were grown to 100% confluency before use. HEK and MDCK cells were serum starved for 2-24 h prior to the initiation of drug treatment.

Blood Stability Studies.

To compare the blood stability of Norleual and D-Nle-Tyr-Ile-NH—(CH$_2$)$_5$—CONH), a representative member of the 6-AH family, 20 µL of compound-containing vehicle (water [Norleual] or 30% ethanol [D-Nle-Tyr-Ile-NH—(CH$_2$)$_5$—CONH$_2$]) was added to 180 µL of heparinized blood and incubated at 37° C. for various times. For Norleual, 37° C. incubations were stopped at 0, 20, 40, and 60 min, and for D-Nle-Tyr-Ile-NH—(CH$_2$)$_5$—CONH$_2$, incubations were stopped at 0, 1, 3 and 5 h.

At the end of each incubation, 20 µL of Nle$^1$-AngIV (100 µg/mL) was added to each sample as an internal standard. D-Nle-Tyr-Ile-NH—(CH$_2$)$_5$—CONH$_2$ samples were centrifuged at 4° C. for 5 min at 2300×g to pellet erythrocytes, and the plasma was transferred to clean tubes. The Norleual and D-Nle-Tyr-Ile-NH—(CH$_2$)$_5$—CONH$_2$ samples were precipitated by adding 3 vol of ice-cold acetonitrile (ACN) and the samples were vortexed vigorously. All samples were centrifuged at 4° C., 2300×g for 5 min and the supernatants were transferred to clean tubes. Samples were then evaporated to dryness in a Savant SpeedVac® concentrator (Thermo Fisher Scientific, Waltham, Mass.), the residue was reconstituted in 225 µl 35% methanol, vortexed briefly, transferred to HPLC autosampler vials, and 100 µl injected into the HPLC system.

Samples were then separated by HPLC on an Econosphere C18 (100 mm×2.1 mm) from Grace Davison Discovery Science (Deerfield, Ill.). Peaks were detected and analyzed by mass spectrographic methods using a LCMS-2010EV mass spectrometer (Shimadzu, Kyoto Japan). The mobile phase consisted of HPLC water (Sigma St. Louis, Mo.) with 0.1% trifluoroacetic or 0.1% heptafluorobutyric acid (Sigma St. Louis, Mo.) and varying concentrations of ACN or methanol. Separation was carried out using a gradient method, at ambient temperature and a flow rate of 0.3 mL/min (see below for more information). Stability half-lives were determined assuming a normal single phase exponential decay using Prism 5 graphical/statistical program (GraphPad, San Diego, Calif.).

IV Pharmacokinetics

Surgerical Procedures.

Male Sprague-Dawley rats (250+ g) were allowed food (Harlan Teklad rodent diet) and water ad libitum in our AAA-LAC certified animal facility. Rats were housed in temperature-controlled rooms with a 12 h light/dark cycle. The right jugular veins of the rats were catheterized with sterile polyurethane Hydrocoat™ catheters (Access Technologies, Skokie, Ill., USA) under ketamine (Fort Dodge Animal Health, Fort Dodge, Iowa, USA) and isoflurane (Vet One™, MWI, Meridian, Id., USA) anesthesia. The catheters were exteriorized through the dorsal skin. The catheters were flushed with heparinized saline before and after blood sample collection and filled with heparin-glycerol locking solution (6 mL glycerol, 3 mL saline, 0.5 mL gentamycin (100 mg/mL), 0.5 mL heparin (10,000 u/mL)) when not used for more than 8 h. The animals were allowed to recover from surgery for several days before use in any experiment, and were fasted overnight prior to the pharmacokinetic experiment.

Pharmacokinetic Study.

Catheterized rats were placed in metabolic cages prior to the start of the study and time zero blood samples were collected. Animals were then dosed intravenously via the jugular vein catheters, with D-Nle-Tyr-Ile-NH—(CH$_2$)$_5$—CONH$_2$ (24 mg/kg) in 30% ethanol. After dosing, blood samples were collected as follows (times and blood volumes collected are listed in chronological order):

| Compound | Time (min) | Blood Volume Collected (µl) |
|---|---|---|
| D-Nle-Tyr-Ile-NH—(CH$_2$)$_5$—CONH$_2$ | 0, 12, 30, 60, 90, 120, 180, 240, 300 | 200, 200, 200, 200, 200, 300, 400, 500, 500 |

After each blood sample was taken, the catheter was flushed with saline solution and a volume of saline equal to the volume of blood taken was injected (to maintain total blood volume).

Blood Sample Preparation.

Upon collection into polypropylene microfuge tubes without heparin, blood samples were immediately centrifuged at 4° C., 2300×g for 5 min to remove any cells and clots and the serum transferred into clean microcentrifuge tubes. A volume of internal standard (Nle$^1$-AngIV, 100 µg/mL) equal to 0.1 times the sample serum volume was added. A volume of ice-cold acetonitrile equal to four times the sample serum volume was then added and the sample vortexed vigorously for 30 s. The supernatants were transferred to clean tubes, then held on ice until the end of the experiment, and stored at 4° C. afterward until further processing.

Serial dilutions of D-Nle-Tyr-Ile-NH—(CH$_2$)$_5$—CONH$_2$ in 30% ethanol were prepared from the stock used to dose the animals for standard curves. 20 µL of each serial dilution was added to 180 µL of blood on ice for final concentrations of 0.01 µg/mL, 0.1 µg/mL, 1 µg/mL and 10 µg/mL. The samples were centrifuged at 4° C., 2300×g for 5 min and the serum transferred into polypropylene microcentrifuge tubes. A volume of internal standard (Nle$^1$-AngIV, 100 µg/mL) equal to 0.1 times the sample serum volume was added. A volume of ice-cold acetonitrile equal to four times the sample serum volume was then added and the sample vortexed vigorously for 30 s. The supernatants were transferred to clean tubes and samples stored at 4° C. and processed alongside the pharmacokinetic study samples. All samples were evaporated to dryness in a Savant SpeedVac® concentrator. The residue was reconstituted in 225 µl 35% methanol and vortexed briefly. The samples were then transferred to HPLC autosampler vials and 100 µl was injected into the HPLC system a total of 2 times (2 HPLC/MS analyses) for each sample.

Chromatographic System and Conditions.

The HPLC/MS system used was from Shimadzu (Kyoto, Japan), consisting of a CBM-20A communications bus module, LC-20AD pumps, SIL-20AC auto sampler, SPD-M20A diode array detector and LCMS-2010EV mass spectrometer. Data collection and integration were achieved using Shimadzu LCMS solution software. The analytical column used was an Econosphere C18 (100 mm×2.1 mm) from Grace Davison Discovery Science (Deerfield, Ill., USA). The mobile phase consisted of HPLC grade methanol and water with 0.1% trifluoroacetic acid. Separation was carried out using a non-isocratic method (40%-50% methanol over 10 min) at ambient temperature and a flow rate of 0.3 mL/min. For MS analysis, a positive ion mode (Scan) was used to monitor the m/z of D-Nle-Tyr-Ile-NH—(CH$_2$)$_5$—CONH$_2$ at 542 and the m/z of Nle$^1$-AngIV (used for internal standard) at 395. Good separation of D-Nle-Tyr-Ile-NH—(CH$_2$)$_5$—CONH$_2$ and the internal standard in blood was successfully achieved. No interfering peaks co-eluted with the analyte or internal standard. Peak purity analysis revealed a peak purity index for D-Nle-Tyr-Ile-NH—(CH$_2$)$_5$—CONH$_2$ of 0.95 and the internal standard of 0.94. D-Nle-Tyr-Ile-NH—(CH$_2$)$_5$—CONH$_2$ eluted at 5.06 min and the internal standard at 4.31 min. Data were normalized based on the recovery of the internal standard.

Pharmacokinetic Analysis.

Pharmacokinetic analysis was performed using data from individual rats. The mean and standard deviation (SD) were calculated for the group. Non-compartmental pharmacokinetic parameters were calculated from serum drug concentration-time profiles by use of WinNonlin® software (Pharsight, Mountain View, Calif., USA). The following relevant parameters were determined where possible: area under the concentration-time curve from time zero to the last time point (AUC$_{0\text{-}last}$) or extrapolated to infinity (AUC$_{0\text{-}\infty}$), C$_{max}$ concentration in plasma extrapolated to time zero (C$_0$), terminal elimination half-life (t$_{1/2}$), volume of distribution (Vd), and clearance (CL).

Microsomal Metabolism.

Male rat liver microsomes were obtained from Celsis (Baltimore, Md., USA). The protocol from Celsis for assessing microsomal-dependent drug metabolism was followed with minor adaptations. An NADPH regenerating system (NRS) was prepared as follows: 1.7 mg/mL NADP, 7.8 mg/mL glucose-6-phosphate and 6 units/mL glucose-6-phosphate dehydrogenase were added to 10 mL 2% sodium bicarbonate and used immediately. 500 µM solutions of Norleual, D-Nle-Tyr-Ile-NH—(CH$_2$)$_5$—CONH$_2$, piroxicam, verapamil and 7-ethoxycoumarin (low, moderate and highly metabolized controls, respectively) were prepared in acetonitrile. Microsomes were suspended in 0.1M Tris buffer (pH 7.38) at 0.5 mg/mL and 100 µL of the microsomal suspension was added to pre-chilled microcentrifuge tubes on ice. To each sample, 640 µL 0.1M Tris buffer, 10 µL 500 µM test compound, and 250 µL of NRS was added. Samples were incubated in a rotisserie hybridization oven at 37° C. for the appropriate incubation times (10, 20, 30 40 or 60 min). 500 µL from each sample was transferred to tubes containing 500 µL ice-cold acetonitrile with internal standard per incubation sample. Standard curve samples were prepared in incubation buffer and 500 µL added to 500 µL ice-cold acetonitrile with internal standard. All samples were then analyzed by high performance liquid chromatography/mass spectrometry. Drug concentrations were determined and loss of parent relative to negative control samples containing no microsomes was calculated. Clearance was determined by nonlinear regression analysis for k$_e$ and t$_{1/2}$ and the equation Cl$_{int}$=k$_e$ Vd. For in vitro-in vivo correlation, Cl$_{int}$ per kg body weight was calculated using the following measurements for Sprague-Dawley rats: 44.8 mg of protein per g of liver, 40 g of liver per kg of body weight.

HGF Binding.

The binding of 6-AH analogs to HGF was assessed by competition using a soluble binding assay. 250 µl of PBS containing human HGF (1.25 ng) were incubated with $^3$H-Hinge, the central dimerization domain of HGF, in the presence of varying concentrations of 6-AH analogs between 10$^{-13}$ M to 10$^{-7}$ M (half-log dilutions) for 40 min at 37° C. The incubates were then spun through Bio-Gel P6 spin columns (400 µl packed volume) for 1 min to separate free and bound $^3$H-Hinge and the eluent was collected. Five milliliters of scintillation fluid was added to the eluent, which contained the HGF bound $^3$H-Hinge, and was then counted using scintillation counter. Total disintegrations per minute of bound $^3$H-Hinge were calculated based on machine counting efficiency. The Ki values for the binding of the peptides were determined using the Prism 5. Competition binding curves were performed in triplicate. Preliminary kinetic studies indicated that equilibrium binding was reached by 40 min of incubation at 37° C. $^3$H—Hinge has recently been shown to bind to HGF with high affinity (Kawas et al., 2011).

HGF Dimerization.

HGF dimerization was assessed using PAGE followed by silver staining (Kawas et al., 2011). Human HGF at a concentration of 0.08 ng/µl with or without 6-AH analogs was incubated with heparin at a final concentration of 5 µg/ml. Loading buffer was then added to each sample and the mixture separated by native PAGE using gradient Criterion XT precast gels (4-12% Bis-Tris; Biorad Laboratories, Hercules, Calif.). Next the gel was silver stained for the detection of the HGF monomers and dimers. Bands were quantitated from digital images using a UVP phosphoimager (Upland, Calif.).

Western Blotting.

HEK293 cells were seeded in 6 well tissue culture plates and grown to 95% confluency in DMEM containing 10% FBS. The cells were serum deprived for 24 h prior to the treatment to reduce the basal levels of phospho-Met. Following serum starvation, cocktails comprised of vehicle and HGF with/without 6-AH analogs were prepared and pre-incubated for 30 min at room temperature. The cocktail was then added to the cells for 10 min to stimulate the Met receptor and downstream proteins. Cells were harvested using RIPA lysis buffer (Millipore; Billerica, Mass.) fortified with phosphatase inhibitor cocktails 1 and 2 (Sigma-Aldrich; St. Louis, Mo.). The lysate was clarified by centrifugation at 15,000 nx g for 15 min, protein concentrations were determined using the BCA total protein assay (Pierce), and then appropriate volumes of the lysates were diluted with 2× reducing Laemmli buffer and heated for ten min at 95° C. Samples containing identical amounts of protein were resolved using SDS-PAGE (Criterion, BioRad Laboratories), transferred to nitrocellulose, and blocked in Tris-buffered saline (TBS) containing 5% milk for 1 h at room temperature. The phospho-Met antibody were added to the blocking buffer at a final concentration of 1:1000 and incubated at 4° C. overnight with gentle agitation. The membranes were then washed several times with water and TBS (PBS, 0.05% Tween-20), a 1:5000 dilution of horseradish-peroxidase conjugated goat anti-rabbit antiserum was added, and the membranes further incubated for 1 h at room temperature. Proteins were visualized using the Supersignal West Pico Chemiluminescent Substrate system (Pierce, Fenton, Mo.) and molecular weights determined by comparison to protein ladders (BenchMark, Invitrogen, and Kaleidoscope, BioRad). Film images were digitized and analyzed using a UVP phosphoimager.

Cell Proliferation.

5000 MDCK cells were seeded into the wells of a 96 well plates in 10% FBS DMEM. To induce cellular quiescence, the cells were serum deprived for 24 h prior to initiating the treatments. Following serum starvation, 10 ng/ml HGF alone and with various concentrations of 6-AH analogs or PBS vehicle were added to the media. The cells were allowed to grow under these conditions for 4 days with a daily addition of 6-AH analogs. On the fourth day, 1 mg/ml of 1-(4,5-Dimethylthiazol-2-yl) 3,5-diphenylformazan reagent (MTT, Sigma-Aldrich) prepared in PBS was added to the cells and incubated for 4 h. Dimethyl sulfoxide diluted in a 0.01M glycine buffer was added to solubilize the cell membranes and the absorbance of reduced MTT in the buffer was quantitated at 590 nm using a plate reader (Biotek Synergy 2, Winooski, Vt.). HGF-dependent proliferation was determined by subtracting the basal proliferation (in the absence of HGF) from total proliferation rates in groups containing HGF.

Scattering Assay.

MDCK cells were grown to 100% confluency on the coverslips in six-well plates and washed twice with PBS. The confluent coverslips were then aseptically transferred to new six well plates containing 900 µl serum free DMEM. Norleual, Hinge peptide, and/or HGF (20 ng/ml) were added to appropriate wells. Control wells received PBS vehicle. Plates were incubated at 37° C. with 5% $CO_2$ for 48 h. Media was removed and cells were fixed with methanol. Cells were stained with Diff-Quik Wright-Giemsa (Dade-Behring, Newark, Del.) and digital images were taken. Coverslips were removed with forceps and more digital images were captured. Pixel quantification of images was achieved using Image J and statistics were performed using Prism 5 and InStat v.3.05 (GraphPad; San Diego, Calif.).

Lung Colony Formation.

Six to eight month old C57BL/6 mice were injected with 400,000 B16-F10 cells in 200 µl PBS by tail vein injection and subsequently received daily intraperitoneal injections of either D-Nle-X-Cys-NH—$(CH_2)_5$—$CONH_2$ (10 µg/kg and 100 µg/kg) or a PBS vehicle control. Two weeks later, mice were anesthetized and lungs were perfused with PBS and removed. Photos were taken and lungs were solubilized in 1% Triton x-100, 20 mM Tris, 0.15 M NaCl, 2 mM EDTA, and 0.02% sodium azide. Samples were disrupted by sonication (Mixonix, Farmingdale, N.Y.) and spun. The supernatant was transferred to a 96 well plate and melanin absorbance at 410 nm was measured using a plate reader.

Statistics.

Independent one-way analysis of variance (ANOVA) (InStat v.3.05 and Prism 5) was used to determine differences among groups. Tukey-Kramar or Bonferroni's multiple comparison post-hoc tests were performed where necessary. Statistical comparisons of two groups were determined using the two-tailed Student's t-test (InStat v.3.05 and Prism 5).

Results

Figure 22:
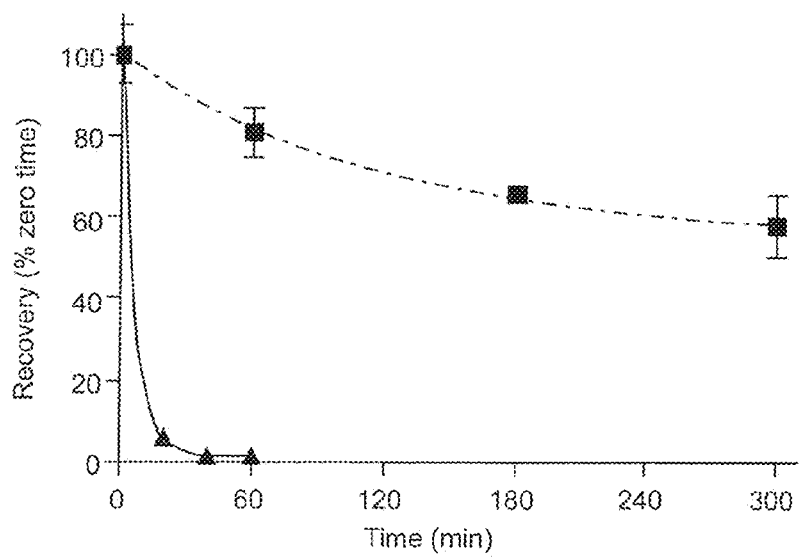
FIG. 22. Stability of Norleual in rat blood as compared to D-Nle-Tyr-Ile-NH—$(CH_2)_5$—$CONH_2$.

The AngIV Analog D-Nle-Tyr-Ile-NH—$(CH_2)_5$—$CONH_2$ is More Metabolically Stable than Norleual (Nle-Tyr-Leu-ψ-$(CH_2$—$NH_2)^{3-4}$-His-Pro-Phe (SEQ ID NO: 1):

The AngIV-related peptidomimetic Norleual was previously shown to possess, anti-HGF/Met, anti-angiogenic, and anti-cancer activities (Yamamoto et al., 2010). The presence of unprotected peptide bonds at both the N- and C-terminal linkages predicts that Norleual should have poor metabolic stability and rapid clearance for the circulation, properties that may limit its clinical utility. In an attempt to overcome this limitation, a family of compounds, the 6-AH family was designed and synthesized to offer defense against exopeptidases. FIG. 22 demonstrates that as expected Norleual is unstable in heparinized blood while D-Nle-Tyr-Ile-NH—$(CH_2)_5$—$CONH_2$ exhibited improved stability.

The AngIV Analog D-Nle-Tyr-Ile-NH—$(CH_2)_5$—$CONH_2$ has a Much Longer Circulating Half-Life than Norleual (Nle-Tyr-Leu-ψ-$(CH_2$—$NH_2)^{3-4}$-His-Pro-Phe (SEQ ID NO: 1)):

As anticipated from the in-vitro blood stability data, D-Nle-Tyr-Ile-NH—$(CH_2)_5$—$CONH_2$ exhibited an extended in vivo elimination half-life of 1012 min after IV injection in rats. Other relevant pharmacokinetic parameters of D-Nle-Tyr-Ile-NH—$(CH_2)_5$—$CONH$, after a single IV bolus dose are summarized in Table 5. Serum data were modeled using WinNonlin® software to perform non-compartmental analysis. D-Nle-Tyr-Ile-NH—$(CH_2)_5$—$CONH_2$ appeared to be extensively distributed outside the central blood compartment and/or bound within the tissues as evidenced by its large volume of distribution (Vd). D-Nle-Tyr-Ile-NH—$(CH_2)_5$—$CONH_2$ is not expected to be highly bound to plasma proteins according to quantitative structure-activity relationship (QSAR) modeling (discussed below) and since total recovery from serum was greater than 35%. These results, which suggest that D-Nle-Tyr-Ile-NH—$(CH_2)_5$—$CONH_2$ is likely to be relatively hydrophobic, are in agreement with the outcome of QSAR modeling estimates generated by ADMET Predictor® that calculated an octanol:water partition coefficient of 28.18 for D-Nle-Tyr-Ile-NH—$(CH_2)_5$—$CONH_2$ (Table 6).

Not surprisingly because of its stability, hydrophobic character, and small size, D-Nle-Tyr-Ile-NH—$(CH_2)_5$—$CONH_2$ was predicted to be orally bioavailable. The $P_{eff}$ value represents the predicted effective human jejunal permeability of the molecule. The predicted $P_{eff}$ value for D-Nle-Tyr-Ile-NH—$(CH_2)_5$—$CONH_2$ (1.53) is intermediate between the predicted $P_{eff}$ values for enalapril (1.25) and piroxicam (2.14), two orally bioavailable drugs. D-Nle-Tyr-Ile-NH—$(CH_2)_5$—$CONH_2$ was also predicted to be 42.68 percent unbound to plasma proteins in circulation, thus making it available for distribution into the tissues.

Also contributing to its slow removal from the blood was a lack of Phase I metabolism for D-Nle-Tyr-Ile-NH—$(CH_2)_5$—$CONH_2$. D-Nle-Tyr-Ile-NH—$(CH_2)_5$—$CONH_2$ exhibited no detectable metabolism over 90 min in an in-vitro metabolism assay using rat liver microsomes (data not shown). Together these data indicate that D-Nle-Tyr-Ile-NH—$(CH_2)_5$—$CONH_2$ is more metabolically stable than Norleual, possesses an elongated half-life in the circulation and penetrates tissue effectively. Overall these favorable pharmacokinetic properties justify the mechanistic and therapeutic evaluation of D-Nle-Tyr-Ile-NH—$(CH_2)_5$—$CONH_2$ and related molecules.

D-Nle-X-Ile-NH—$(CH_2)_5$—$CONH_2$ Analogs Bind HGF and Compete with the [3]H-Hinge Peptide for HGF Binding:

Several members of the D-Nle-X-Ile-NH—$(CH_2)_5$—$CONH_2$, 6-AH family, were analyzed for the capacity to compete for [3]H-Hinge binding to HGF. As will be evident below, members of the 6-AH family display a varied ability to block the biological action of HGF. As such, the HGF binding properties of a selection of analogs with varying biological activity was assessed to determine if there was a relationship between inhibitory activity and affinity for HGF. The hypothesis that was put forth was that analogs are binding directly to HGF and affecting the sequestration of HGF in an inactive form. To begin the evaluation of this idea, we used a [3]H-Hinge peptide as a probe to assess direct HGF binding of the peptides. The use of [3]H-Hinge to probe the interaction was based on the ability of [3]H-Hinge to bind specifically and with high affinity to HGF (Kawas et al., 2011). A competition study was initiated with several derivatives of the D-Nle-X-Ile-NH—$(CH_2)_5$—$CONH_2$ family. This study demonstrated that different analogs have variable abilities to bind HGF, and that the analogs showing antagonism to HGF are acting as a Hinge mimics D-Nle-X-Ile-NH—$(CH_2)_5$—$CONH_2$ derivatives were found to compete with Hinge for HGF binding and exhibited a range of affinities for HGF, with $K_i$s ranging from $1.37 \times 10^{-7}$-$1.33 \times 10^{-10}$ M (FIG. 23). As expected it appears to be relationship between a compound's ability to bind HGF and its capacity to block dimerization and inhibit HGF-dependent activities (see FIGS. 25, 26, 27).

Figure 24B:
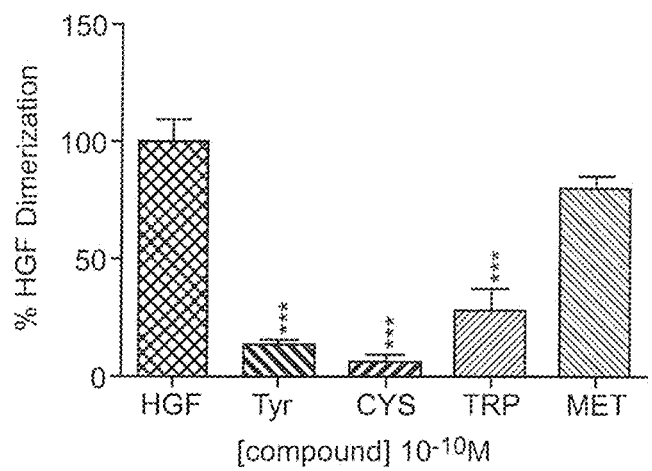

D-Nle-X-Ile-NH—(CH$_2$)$_5$—CONH$_2$ Analogs Block HGF Dimerization:

Several reports have shown that HGF needs to form homodimers and/or multimers, prior to its activation of Met (Chirgadze et al., 1999; Gherardi et al., 2006). This dimer is arranged in a head to tail orientation; the dimer interface comprises a central region, the hinge region that is important for the proper dimer formation and orientation. A homologous sequence-conservation screen against all possible transcripts that were independent of and not derived from angiotensinogen looking for similarities to AngIV identified partial homology with the hinge region (Yamamoto et al., 2010) of the plasminogen family of proteins, which include plasminogen itself, its anti-angiogenic degradation product, angiostatin, and the protein hormones heptocyte growth factor (HGF) and macrophage stimulating protein (MSP). Moreover, the AngIV analog Norleual, which is a potent inhibitor of the HGF/Met system, was shown to bind to HGF and block its dimerization (Kawas et al., 2011). This knowledge coupled with the demonstration that some members of the 6-AH family bound with high affinity to the hinge region of HGF led to the expectation that other active AngIV analogs, like 6-AH family members, could be expected to inhibit HGF dimerization and that the ability of an individual analog to bind HGF and inhibit HGF-dependent processes should be reflected in its capacity to attenuate dimerization. The data in FIG. 24 confirm this expectation by demonstrating that D-Nle-Cys-Ile-NH—(CH$_2$)$_5$—CONH$_2$ and D-Nle-Tyr-Ile-NH—(CH$_2$)$_5$—CONH$_2$, which bind HGF with high affinity (FIG. 23) and effectively attenuate HGF-dependent processes (FIGS. 25, 26, 27) completely block HGF dimer formation. Conversely D-Nle-Met-Ile-NH—(CH$_2$)$_5$—CONH$_2$, which has low affinity for HGF (FIG. 23) and exhibits little anti-HGF/Met activity, is unable to block dimerization at the concentration tested. The D-Nle-Trp-Ile-NH—(CH$_2$)$_5$—CONH$_2$ analog, which exhibits intermediate inhibition of dimerization, predictably has a moderate affinity for HGF and a moderate ability to inhibit HGF-dependent processes (FIGS. 25, 26, 27). Together these data confirm the expectation that active 6-AH analogs can block dimerization and further that dimerization inhibitory potential of an analog translates, at least qualitatively, to its capacity to block HGF-dependent processes.

D-Nle-X-Ile-NH—(CH$_2$)$_5$—CONH$_2$ Analogs Attenuates HGF-Dependent Met Signaling:

After establishing that the 6-AH family members exhibit a range of HGF binding and dimerization inhibitory profiles, we next determined whether these properties would parallel a compound's ability to inhibit Met signaling. Characteristic of tyrosine kinase-linked growth factor receptors like Met is a requisite tyrosine residue auto-phosphorylation step, which is essential for the eventual recruitment of various SH2 domain signaling proteins. Thus we evaluated the ability of several 6-AH analogs to induce Met tyrosine phosphorylation. As anticipated, the data in FIG. 25 demonstrate that both D-Nle-Cys-Ile-NH—(CH$_2$)$_5$—CONH$_2$ and D-Nle-Tyr-Ile-NH—(CH$_2$)$_5$—CONH$_2$, which bind HGF with high affinity (FIG. 23) and effectively block its dimerization (FIG. 24) were able to block Met auto-phosphorylation. The D-Nle-Trp-Ile-NH—(CH$_2$)$_5$—CONH$_2$ analog had intermediate inhibitory activity, and the D-Nle-Met-Ile-NH—(CH$_2$)$_5$—CONH$_2$ analog showed no ability to effect on Met activation. Together, these data indicate that the capacity of 6-AH analogs to inhibit HGF-dependent Met activation paralleled their HGF binding affinity and their capacity to block dimerization.

D-Nle-X-Ile-NH—(CH$_2$)$_5$—CONH$_2$ Analogs Affect HGF/Met Stimulated MDCK Cell Proliferation:

Met activation initiates multiple cellular responses including increased proliferation and motility, enhanced survival, and differentiation (Zhang and Vande Woude, 2003). As an initial test of the ability of 6-AH family members to alter HGF-dependent cellular activity we evaluated the capacity of several members of the family to modify the proliferative activity of Madin-Darby canine kidney (MDCK) cells, a standard cellular model for investigating the HGF/Met system (Stella and Comoglio, 1999). As seen in FIG. 26 there is a wide range of inhibitory activity against HGF dependent cellular proliferation. Similar to the results from the binding and dimerization experiments the Cys$^2$ and Tyr$^2$ analogs exhibited marked inhibitory activity. The Asp$^2$ analog, which had not been evaluated in the earlier studies, also exhibited pronounced inhibitory activity. The Trp$^2$, Phe$^2$, and Ser$^2$ analogs all showed inhibitory activity, albeit less than that observed with the most potent analogs. The decrease in HGF-dependent MDCK proliferation below control levels for some compounds is not surprising since the experiment was carried in 2% serum, which likely contains some level of HGF. The Hinge peptide (KDYIRN), which represents the dimerization domain of HGF, was included as a positive control. A recent study has demonstrated that Hinge binds to HGF with high affinity blocking its dimerization and acting as a potent inhibitor of HGF-dependent cellular activities including MDCK proliferation (Kawas et al., 2011).

D-Nle-X-Ile-NH—(CH$_2$)$_5$—CONH$_2$ Analogs Modify HGF/Met Mediated Cell Scattering in MDCK Cells:

Cell scattering is the hallmark effect of HGF/Met signaling; a process characterized by decreased cell adhesion, increased motility, and increased proliferation. The treatment of MDCK cells with HGF initiates a scattering response that occurs in two stages. First, the cells lose their cell-to-cell adhesion and become polarized. Second, they separate completely and migrate away from each other. It is expected that if the 6-AH family members are capable of inhibiting the HGF/Met system then they should be able to modify HGF dependent MDCK cell scattering.

FIGS. 27A & B indicate that those analogs that were previously found to block HGF dimerization were effective inhibitor of HGF/Met mediated cell scattering in MDCK cells, while those analogs with poor affinity for HGF were ineffective. FIG. 28 shows a correlation between the blockade of HGF dimerization and HGF binding affinity and the ability to prevent MDCK cell scattering.

Figure 29A:
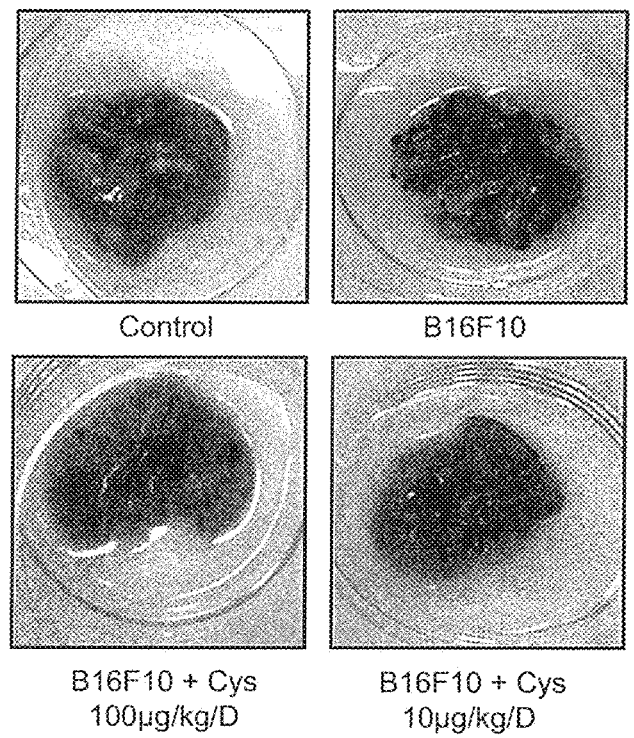
Figure 29B:
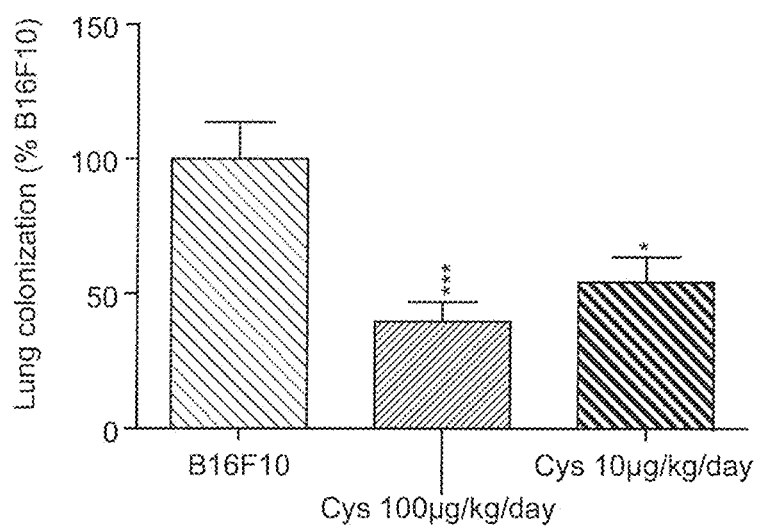

D-Nle-Cys-Ile-NH—(CH$_2$)$_5$—CONH$_2$ Inhibits B16-F10 Murine Melanoma Cell Migration and Lung Colony Formation:

To evaluate the prospective utility of the 6-AH family members' as potential therapeutics, we examined the capacity of [D-Nle-Cys-Ile-NH—(CH$_2$)$_5$—CONH$_2$], an analog that exhibits a strong inhibitory profile against HGF-dependent Met activation, to suppress the migratory and lung colony-foaming capacity of B16-F10 murine melanoma cells. B16 melanoma cells over-express Met (Ferraro et al., 2006), and were chosen for these studies because Met signaling is critical for their migration, invasion, and metastasis. As a final test for the physiological significance of the 6-AH family blockade of Met-dependent cellular outcomes, we evaluated the ability of D-Nle-Cys-Ile-NH—(CH$_2$)$_5$—CONH$_2$ to inhibit the formation of pulmonary colonies by B16-F10 cells after tail vein injection in mice. FIG. 29*a* illustrates the inhibitory response that was observed with daily intraperitoneal injections at two doses (10 µg/kg/day and 100 µg/kg/day) of [D-Nle-Cys-Ile-NH—(CH$_2$)$_5$—CONH$_2$]. FIG. 29*b* provides a quantitative assessment of pulmonary colonization by measuring melanin content, which reflects the level of melanoma colonization. Together these data demonstrate that treatment of melanoma cells with D-Nle-Cys-Ile-NH—(CH$_2$)$_5$—CONH$_2$ radically prevented lung colonization and highlight the utility of the 6-AH analogs as anti-cancer agents.

Discussion:

Recently interest has grown in developing therapeutics targeting the HGF/Met system. At present this interest has been primarily driven by the realization that over-activation of the HGF/c-Met system is a common characteristic of many human cancers (Comoglio et al., 2008; Eder et al., 2009). The potential utility of anti-HGF/Met drugs, however, goes well beyond their use as anti-cancer agents. For example, the recognized involvement of the HGF/c-Met system in the regulation of angiogenesis (see review—supports the potential utility of HGF/Met antagonists for the treatment of disorders in which control of tissue vascularization would be clinically beneficial. These could include hyper-vascular diseases of the eye like diabetic retinopathy and the wet type of macular degeneration. In both cases anti-angiogenic therapies are currently in use (see review—Jeganathan, 2011). Anti-angiogenics are also being examined as treatment options in a variety of other disorders ranging from obesity where adipose tissue vascularization is targeted (Daquinag et al., 2011), to chronic liver disease (Coulon et al., 2011), to psoriasis where topical application of anti-angiogenic drugs is being considered (Canavese et al., 2010).

Currently the pharmaceutical industry is employing two general approaches to block Met-dependent cellular activities (Eder et al., 2009; Liu X et al 2010). The first involves the development of single-arm humanized antibodies to HGF (Burgess et al., 2006; Stabile et al., 2008) or Met (Martens et al., 2006). The second approach utilizes "kinase inhibitors", which block the intracellular consequences of Met activation. These 'kinase inhibitors" are small hydrophobic molecules that work intracellularly to compete for the binding of ATP to the kinase domain of Met thus inhibiting receptor autophosphorylation, 2002; Christensen et al., 2003; Sattler et al., 2003). Despite the promise of the biologic and kinase-inhibitor approaches, which are currently represented in clinical trials, both have limitations arising from toxicity or specificity considerations and/or cost (Hansel et al., 2010; Maya, 2010).

A third approach, which our laboratory has been pursuing exploits a step in the activation process of the HGF-Met system; namely the need for HGF to pre-dimerize before it is able to activate Met. Thus we have targeted the dimerization process by developing molecules that mimic the dimerization domain, the hinge region, with idea that they can act as dominant negative replacements. Recent studies have validated this general approach demonstrating that molecules designed around angiotensin IV (Yamamoto et al, 2010) or the hinge sequence itself (Kawas et al., 2011) can bind HGF, block its dimerization, and attenuate HGF-dependent cellular actions. The studies described herein represent a first step toward producing useful therapeutics targeted at HGF dimerization. The primary focus of this study was to improve the pharmacokinetic characteristics of a parent compound, Norleual (Yamamoto et al., 2010) while maintaining biological activity. To this end we successfully synthesized and evaluated a family of new molecules, the 6-AH family [D-Nle-X-Ile-NH—(CH$_2$)$_5$—COOH]. A subset of these molecules not only had improved metabolic stability and circulating $t_{1/2}$ but exhibited excellent in vitro and in vivo activity.

In addition to characterizing a new family of HGF/Met antagonists, this Example demonstrates a qualitative relationship between the ability of a compound to bind HGF and block HGF dimerization and its observed in vitro biological activity. Moreover these studies provide initial structure-activity data and pave the way for more extensive evaluation. The chemical modifications that were made at the N- and C-terminals of the AngIV molecule and the resultant improvement in metabolic stability highlight the critical role played by exopeptidases in the metabolism of AngIV-derived molecules. The demonstrated importance of protecting the terminals to pharmacokinetic characteristics suggests numerous additional synthetic approaches that may be applicable including the insertion of non-peptide linkages (see Sardinia et al., 1994) between the first and second amino acids, the replacement of the N-terminal amino acid with a non-α amino acid, and N-terminal acylation.

In sum these studies further validate the notion that targeting the dimerization domain of HGF is an effective means of inhibiting the HGF/Met system. Further they demonstrate that molecules with favorable pharmacokinetic characteristics can be produced thus highlighting their clinical utility.

TABLE 5

WinNonlin ® estimated pharmacokinetic parameters for D-Nle-Tyr-Ile-NH—(CH$_2$)$_5$—CONH$_2$ after intravenous administration in adult male Sprague-Dawley rats

| Pharmacokinetic Parameter | D-Nle-Tyr-Ile-NH—(CH$_2$)$_5$—CONH$_2$ (Mean ± SEM) |
|---|---|
| AUC$_{0-\infty}$ (min · ng/mL) | 692.5 ± 293.2 |
| Vd (L/kg) | 104186.8 ± 65034.3 |
| Cp$^0$ (ng/mL) | 68.2 ± 32.2 |
| t$_{1/2}$ (min) | 1012.0 ± 391.4 |
| KE (min-1) | 0.001 ± 0.0002 |
| CL (L/min/kg) | 58.3 ± 15.6 |

Mean +/− SEM; n = 5.
AUC$_{0-\infty}$ = area under the curve.
Vd = volume of distribution.
Cp$^0$ = initial concentration of drug in serum.
t$_{1/2}$ = biological half-life.
KE = rate of elimination.
CL = clearance rate.

TABLE 6

Predicted physiochemical properties of D-Nle-Tyr-Ile-NH—(CH$_2$)$_5$—CONH$_2$.

| Physicochemical Property | Predicted Value |
|---|---|
| LogP | 1.45 |
| P$_{eff}$ | 1.53 |
| P$_{avg}$ | 0.39 |
| Pr$_{Unbnd}$ | 42.68 |

The physiochemical properties of D-Nle-Tyr-Ile-NH—(CH$_2$)$_5$—CONH$_2$ were estimated following modeling with ADMET Predictor ® software.
LogP is the octanol:water partitioning coefficient.
P$_{eff}$ is the predicted effective human jejunal permeability.
P$_{avg}$ is the approximate average intestinal permeability along the entire human intestinal tract.
Pr$_{Unbnd}$ is the percent unbound to plasma proteins.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

REFERENCES

Achim, C. L., S. Katyal, et al. (1997). "Expression of HGF and cMet in the developing and adult brain." Brain Res Dev Brain Res 102(2): 299-303.

Abounader R, Lal B, Luddy C, Koe G, Davidson B, Rosen E M and Laterra J (2002) In vivo targeting of SF/HGF and c-met expression via U1snRNA/ribozymes inhibits glioma growth and angiogenesis and promotes apoptosis. FASEB JOURNAL 16:108-110.

Aguirre Ghiso J A, Alonso D F, FarÃfÂ-as E F, Gomez D E and de Kier JoffÃfÂ" E B (1999) Deregulation of the signaling pathways controlling urokinase production. Its relationship with the invasive phenotype. European journal of biochemistry/FEBS 263:295-304.

Akimoto, M., A. Baba, et al. (2004). "Hepatocyte growth factor as an enhancer of nmda currents and synaptic plasticity in the hippocampus." Neuroscience 128(1): 155-62.

Aoki M, Warita H, Suzuki N, Itoyama Y. (2009) Development of motor neuron restorative therapy in amyotrophic lateral sclerosis using hepatocyte growth factor. Rinsho Shinkeigaku 49: 814-817.

Ahmet I, Sawa Y, Iwata K and Matsuda H (2002) Gene transfection of hepatocyte growth factor attenuates cardiac remodeling in the canine heart: A novel gene therapy for cardiomyopathy. Journal of Thoracic and Cardiovascular Surgery 124:957-963.

Balschun, D., D. Moechars, et al. "Vesicular glutamate transporter VGLUT1 has a role in hippocampal long-term potentiation and spatial reversal learning." Cereb Cortex 20(3): 684-93.

Bean J, Brennan C, Shih J-Y, Riely G, Viale A, Wang L, Chitale D, Motoi N, Szoke J, Broderick S, Balak M, Chang W-C, Yu C-J, Gazdar A, Pass H, Rusch V, Gerald W, Huang S-F, Yang P-C, Miller V, Ladanyi M, Yang C-H and Pao W (2007) MET amplification occurs with or without T790M mutations in EGFR mutant lung tumors with acquired resistance to gefitinib or erlotinib. Proceedings of the National Academy of Sciences of the United States of America. 104:20932.

Birchmeier C, Birchmeier W, Gherardi E and Vande Woude G F (2003) MET, METASTASIS, MOTILITY AND MORE, in Nature Reviews Molecular Cell Biology pp 915-925, Nature Publishing Group.

Birchmeier, C., E. Sonnenberg, et al. (1993). "Tyrosine kinase receptors in the control of epithelial growth and morphogenesis during development." Bioessays 15(3): 185-90.

Boccaccio C, Gaudino G, Gambarotta G, Galimi F and Comoglio P M (1994) Hepatocyte growth factor (HGF) receptor expression is inducible and is part of the delayed-early response to HGF. The Journal of biological chemistry 269:12846-12851.

Boros P and Miller C M (1995) Hepatocyte growth factor: A multifunctional cytokine. Lancet 345:293.

Borowiak M, Garratt A N, WÃfÂ¼stefeld T, Strehle M, Trautwein C, Birchmeier C and Wigler M H (2004) Met Provides Essential Signals for Liver Regeneration. Proceedings of the National Academy of Sciences of the United States of America 101:10608-10613.

Boulton M (1999) A role for hepatocyte growth factor in diabetic retinopathy? British journal of ophthalmology. 83:763.

Braszko, J. J., G. Kupryszewski, et al. (1988). "Angiotensin II-(3-8)-hexapeptide affects motor activity, performance of passive avoidance and a conditioned avoidance response in rats." Neuroscience 27(3): 777-83

Burgess T, Coxon A, Meyer S, Sun J, Rex K, Tsuruda T, Chen Q, Ho S Y, Li L, Kaufman S, McDorman K, Cattley R C, Elliott G, Zhang K, Feng X, Jia X C, Green L, Radinsky R and Kendall R (2006) Fully human monoclonal antibodies to hepatocyte growth factor with therapeutic potential against hepatocyte growth factor/c-Met-dependent human tumors. Cancer research 66:1721-1729.

Calissano P, Matrone C, Amadoro G (2010) Nerve growth factor as a paradigm of neurotrophins to Alzheimer's disease. Dev Neurobiol 70:372-383.

Canavese M, Altruda F, Ruzicka T, and Schauber J (2010 Barkmeier A. J & Carvounis P E (2011) Retinal pigment epithelial tears and the management of exudative age-related macular degeneration. Seminars in Ophthalmology 26: 94-103.

Christensen J G Burrows J and Salgia R (2005) c-Met as a target for human cancer and characterization of inhibitors for therapeutic intervention. Cancer Letters 225:1-26.

Christensen J G, Schreck R, Burrows J, Kuruganti P, Chan E, Le P, Chen J, Wang X, Ruslim L, Blake R, Lipson K E, Ramphal J, Do S, Cui J J, Chemington J M and Mendel D B (2003) A selective small molecule inhibitor of c-Met kinase inhibits c-Met-dependent phenotypes in vitro and exhibits cytoreductive antitumor activity in vivo. Cancer Research 63:7345-7355.

Chirgadze D Y, Hepple J P, Zhou H, Byrd R A, Blundell T L and Gherardi E (1999) Crystal structure of the NK1 fragment of HGF/SF suggests a novel mode for growth factor dimerization and receptor binding. Nature structural biology 6:72-79.

Comoglio P M, Giordano S and Trusolino L (2008) Drug development of MET inhibitors: targeting oncogene addiction and expedience. Nature reviews. Drug discovery 7:504-516.

Coulon S, Heindryckx F, Geerts A, Van Steenkiste, C Colle I, and Van Vlierberghe H (2011) Angiogenesis in chronic liver disease and its complications. Liver International 31: 146-162.

Danilkovitch-Miagkova A and Zbar B (2002) Dysregulation of Met receptor tyrosine kinase activity in invasive tumors. The Journal of clinical investigation 109:863-867.

Daquinag A C, Zhang Y, and Kolonin M G (2011) Vascular targeting of adipose tissue as an anti-obesity approach. Trends in Pharmacological Sciences 32:300-307.

Date, I., N. Takagi, et al. (2004). "Hepatocyte growth factor improved learning and memory dysfunction of microsphere-embolized rats." J Neurosci Res 78(3): 442-53.

Davis, C. J., E. A. Kramar, et al. (2006). "AT4 receptor activation increases intracellular calcium influx and induces a non-N-methyl-D-aspartate dependent form of long-term potentiation." Neuroscience 137(4): 1369-79.

De Bundel, D., H. Demaegdt, et al. (2010) "Involvement of the AT1 receptor subtype in the effects of angiotensin IV and LVV-haemorphin 7 on hippocampal neurotransmitter levels and spatial working memory." J Neurochem 112(5): 1223-34

Derksen P W, de Gorter D J, Meijer H P, Bende R J, van Dijk M, Lokhorst H M, Bloem A C, Spaargaren M and Pals S T (2003) The hepatocyte growth factor/Met pathway controls proliferation and apoptosis in multiple myeloma. Leukemia: official journal of the Leukemia Society of America, Leukemia Research Fund, U.K 17:764-774.

Dikmen S S, Corrigan J D, Levin H S, Machamer J, Stiers W, Weisskopf M G (2009) Cognitive outcome following traumatic brain injury. J Head Trauma Rehabil. 24:430-438.

Donate L E, Gherardi E, Srinivasan N, Sowdhamini R, Aparicio S and Blundell T L (1994) Molecular evolution and domain structure of plasminogen-related growth factors (HGF/SF and HGF1/MSP). *Protein Science* 3:2378-2394.

Ebens A, Brose K, Leonardo E D, Hanson M G, Jr., Bladt F, Birchmeier C, Banes B A and Tessier-Lavigne M (1996) Hepatocyte growth factor/scatter factor is an axonal chemoattractant and a neurotrophic factor for spinal motor neurons. *Neuron* 17:1157-1172.

Eder J P, Vande Woude G F, Boerner S A and LoRusso P M (2009) Novel therapeutic inhibitors of the c-Met signaling pathway in cancer. *Clinical cancer research: an official journal of the American Association for Cancer Research* 15:2207-2214.

El-Husseini, A. E., E. Schnell, et al. (2000). "PSD-95 involvement in maturation of excitatory synapses." Science 290 (5495): 1364-8.

Elsen G E, Choi L Y, Prince V E, Ho R K. (2009) The autism susceptibility gene met regulates zebrafish cerebellar development and facial motor neuron migration. Dev Biol 335: 78-92.

Fafalios A, Ma J, Tan X, Stoops J, Luo J, Defrances M C, Zarnegar R. (2011) A hepatocyte growth factor receptor (Met)-insulin receptor hybrid governs hepatic glucose metabolism. *Nat. Med.* 17:1577-84.

Ferrario D, Corso S, Fasano E, Panieri E, Santangelo R, Borrello S, Giordano S, Pani G and Galeotti T (2006) Pro-metastatic signaling by Met through RAC-1 and reactive oxygen species (ROS). *Oncogene* 25:3689-3698

Ferreira, A. and M. Rapoport (2002). "The synapsins: beyond the regulation of neurotransmitter release." Cell Mol Life Sci 59(4): 589-95.

Fisher, A., Z. Pittel, et al. (2003). "M1 muscarinic agonists can modulate some of the hallmarks in Alzheimer's disease: implications in future therapy." J Mol Neurosci 20(3): 349-56.

Flaquer M, Franquesa M, Vidal A, Bolaños N, Torras J, Lloberas N, Herrero-Fresneda I, Grinyó J M, Cruzado J M. (2010) Hepatocyte growth factor gene therapy enhances infiltration of macrophages and may induce kidney repair in db/db mice as a model of diabetes. *Diabetologia*. March 30. [Epub ahead of print]

Fujimoto J and Kaneda Y (1999) Reversing liver cirrhosis: impact of gene therapy for liver cirrhosis. *GENE THERAPY-BASINGSTOKE*-6:305-306.

Gao X, Deng P, Xu Z C, Chen J (2011) Moderate traumatic brain injury causes acute dendritic and synaptic degeneration in the hippocampal dentate gyms. *PLoS One.* 6:e24566

Gherardi E, Sandin S, Petoukhov M V, Finch J, Youles M E, Ä" Fverstedt L-Gr, Miguel R N, Biundell T L, Vande Woude G F, Skoglund U and Svergun D I (2006) Structural basis of hepatocyte growth factor/scatter factor and MET signalling, in *Proceedings of the National Academy of Sciences of the United States of America* pp 4046-4051.

Gherardi E, Birchmeier W, Birchmeier C, Vande Woude G (2012) Targeting MET in cancer: rationale and progress. *Nat Rev Cancer.* 12:89-103. Halaban R, Rubin J S, Funasaka Y, Cobb M, Boulton T, Faletto D, Rosen E, Chan A, Yoko K, White W and et al. (1992) Met and hepatocyte growth factor/scatter factor signal transduction in normal melanocytes and melanoma cells. *Oncogene* 7:2195-2206.

Han, K. and E. Kim (2008). "Synaptic adhesion molecules and PSD-95." Prog Neurobiol 84(3): 263-83.

Hansel T T, Kropshofer H, Singer T, Mitchell J A and George A J (2010) The safety and side effects of monoclonal antibodies. *Nature Reviews. Drug Discovery* 9:325-338.

Hara T, Ooi A, Kobayashi M, Mai M, Yanagihara K and Nakanishi I (1998) Amplification of c-myc, K-sam, and c-met in Gastric Cancers: Detection by Fluorescence In Situ Hybridization. *Laboratory investigation.* 78:1143.

Harding, J. W., V. I. Cook, et al. (1992). "Identification of an AII(3-8) [AIV] binding site in guinea pig hippocampus." Brain Res 583(1-2): 340-3.

Hartmann G, Weidner K M, Schwarz H and Birchmeier W (1994) The motility signal of scatter factor/hepatocyte growth factor mediated through the receptor tyrosine kinase met requires intracellular action of Ras. *The Journal of biological chemistry* 269:21936-21939.

Hayashi Y, Kawazoe Y, Sakamoto T, Ojima M, Wang W, Takazawa T, Miyazawa D, Ohya W, Funakoshi H, Nakamura T, Watabe K. (2006) Adenoviral gene transfer of hepatocyte growth factor prevents death of injured adult motoneurons after peripheral nerve avulsion. *Brain Res* 21: 187-195.

Hering, H. and M. Sheng (2001). "Dendritic spines: structure, dynamics and regulation." Nat Rev Neurosci 2(12): 880-8.

Honda S, Kagoshima M, Wanaka A, Tohyama M, Matsumoto K and Nakamura T (1995) Localization and functional coupling of HGF and c-Met/HGF receptor in rat brain: implication as neurotrophic factor. *Brain research. Molecular brain research* 32:197-210.

Houldsworth J, Cordon-Cardo C, Ladanyi M, Kelsen D P and Chaganti R S (1990) Gene amplification in gastric and esophageal adenocarcinomas. *Cancer research* 50:6417-6422.

Ieraci A, Formi P E, Ponzetto C. Viable hypomorphic signaling mutant of the Met receptor reveals a role for hepatocyte growth factor in postnatal cerebellar development. (2002) *Proc Natl Acad Sci USA.* 99:15200-5.

Jeganathan, V. S. E. (2011) Anti-angiogenesis drugs in diabetic retinopathy. *Current Pharmaceutical Biotechnology* 12:369-372.

Jin H, Yang R, Li W, Ogasawara A K, Schwall R, Eberhard D A, Zheng Z, Kahn D and Paoni N F (2003) Early Treatment with Hepatocyte Growth Factor Improves Cardiac Function in Experimental Heart Failure Induced by Myocardial Infarction. *JOURNAL OF PHARMACOLOGY AND EXPERIMENTAL THERAPEUTICS* 304:654-705.

Jun E J, Kim H S and Kim Y H (2007) Role of HGF/c-Met in serum-starved ARPE-19 cells. *Korean journal of ophthalmology: KJO* 21:244-250.

Jung, W., E. Castren, et al. (1994). "Expression and functional interaction of hepatocyte growth factor-scatter factor and its receptor c-met in mammalian brain." J Cell Biol 126(2): 485-94.

Kadoyama K, Funakoshi H, Ohya-Shimada W, Nakamura T, Matsumoto K, Matsuyama S, Nakamura T. (2009) Disease-dependent reciprocal phosphorylation of serine and tyrosine residues of c-Met/HGF receptor contributes disease retardation of a transgenic mouse model of ALS. *Neurosci Res.* 65:194-200.

Kadoyama K, Funakoshi H, Ohya W, Nakamura T. (2007) Hepatocyte growth factor (HGF) attenuates gliosis and motoneuronal degeneration in the brainstem motor nuclei of a transgenic mouse model of ALS. *Neurosci Res* 59: 446-456.

Kaibori M, Inoue T, Oda M, Naka D, Kawaguchi T, Kitamura N, Miyazawa K, Kwon A H, Kamiyama Y and Okumura T (2002) Exogenously Administered HGF Activator Augments Liver Regeneration through the Production of Biologically Active HGF. *Biochemical and Biophysical Research Communications* 290:475-481.

Kane M J, Angoa-Pérez M, Briggs D I, Viano D C, Kreipke C W, Kuhn D M (2011). A mouse model of human repetitive mild traumatic brain injury. *J Neurosci Methods.* September 12. [Epub ahead of print]

Kaplan G B, Vasterling J J, Vedak P C (2010) Brain-derived neurotrophic factor in traumatic brain injury, post-traumatic stress disorder, and their comorbid conditions: role in pathogenesis and treatment. *Behav Pharmacol.* 21:427-437.

Kasai, H., M. Fukuda, et al. (2001)"Structural dynamics of dendritic spines in memory and cognition." Trends Neurosci 33(3): 121-9.

Kakazu A, Chandrasekher G, and Bazan H E (2004) HGF protects corneal epithelial cells from apoptosis by the PI-3K/Akt-1/Bad—but not the ERK1/2-mediated signaling pathway. *Investigative Ophthalmology and Visual Science* 45:3485-3492.

Kanda S, Kanetake H and Miyata Y (2006) HGF-induced capillary morphogenesis of endothelial cells is regulated by Src. *Biochemical & Biophysical Research Communications* 344:617-622.

Kato N, Nakanishi K, Nemoto K. (2009) Efficacy of HGF gene transfer for various nervous injuries and disorders. *Cent Nery Syst Agents Med Chem* 9: 300-306.

Katsura Y, Okano T, Noritake M, Kosano H, Nishigori H, Kado S and Matsuoka T (1998) Hepatocyte growth factor in vitreous fluid of patients with proliferative diabetic retinopathy and other retinal disorders. *Diabetes care* 21:1759-1763.

Kawas L H, Yamamoto B J, Wright J W, Harding J W. (2011) Mimics of the dimerization domain of hepatocyte growth factor exhibit anti-met and anti-cancer activity. *Journal of Pharmacological and Experimental therapeutics,* 339: 509-518.

Kawas L H, McCoy A T, Yamamoto B J, Wright J W, Harding J W. (2012) Development of Angiotensin IV Analogs as Hepatocyte Growth Factor/Met Modifiers. *The Journal of Pharmacology and Experimental Therapeutics.* (November 30 Epub ahaed of print).

Kennedy, M. B. (1997). "The postsynaptic density at glutamatergic synapses." Trends Neurosci 20(6): 264-8.

Kitamura S, Kondo S, Shinomura Y, Kanayama S, Miyazaki Y, Kiyohara T, Hiraoka S and Matsuzawa Y (2000) Met/HGF receptor modulates bcl-w expression and inhibits apoptosis in human colorectal cancers. *British Journal of Cancer* 83:668-673.

Koike H, Ishida A, Shimamura M, Mizuno S, Nakamura T, Ogihara T, Kaneda Y, Morishita R. prevention of onset of Parkinson's disease by in vivo gene transfer of human hepatocyte growth factor in rodent model: a model of gene therapy for Parkinson's disease. (2006) *Gen Ther* 13:1639-1644.

Kondo I, Ohmori K, Oshita A, Takeuchi H, Fuke S, Shinomiya K, Noma T, Namba T and Kohno M (2004) Treatment of acute myocardial infarction by hepatocyte growth factor gene transfer: the first demonstration of myocardial transfer of a "functional" gene using ultrasonic microbubble destruction. *Journal of the American College of Cardiology* 44:644-653.

Kramar, E. A., D. L. Armstrong, et al. (2001). "The effects of angiotensin IV analogs on long-term potentiation within the CA1 region of the hippocampus in vitro." Brain Res 897(1-2): 114-21.

Krebs, L. T., J. M. Hanesworth, et al. (2000). "A novel angiotensin analog with subnanomolar affinity for angiotensin-converting enzyme." J Pharmacol Exp Ther 293(1): 260-7.

Kuniyasu H, Yasui W, Kitadai Y, Yokozaki H, Ito H and Tahara E (1992) Frequent amplification of the c-met gene in scirrhous type stomach cancer. *Biochemical and Biophysical Research Communications* 189:227-232.

Lan F, Xu J, Zhang X, Wong V W, Li X, Lu A, Lu W, Shen L, Li L. Hepatocyte growth factor promotes proliferation and migration in immortalized progenitor cells. (2008) *Neuroreport.* 19: 765-9.

Lee, J., A. L. Albiston, et al. (2004). "Effect of I.C.V. injection of AT4 receptor ligands, NLE1-angiotensin IV and LVV-hemorphin 7, on spatial learning in rats." Neuroscience 124(2): 341-9.

Lim C S and Walikonis R S. Hepatocyte growth factor and c-Met promote dendritic maturation during hippocampal neuron differentiation via the Akt pathway. (2008) *Cell Signal.* 20: 825-35.

Liu X, Newton R C and Scherle P A (2009) Developing c-MET pathway inhibitors for cancer therapy: progress and challenges. *Trends in molecular medicine* 16:37-45.

Liu X, Yao W, Newton R C and Scherle P A (2008) Targeting the c-MET signaling pathway for cancer therapy. *Expert opinion on investigational drugs* 17:997-1011.

Liu X, Newton R C and Scherle P A (2010) Developing Met pathway inhibitors for cancer therapy: progress and challenges. *Trends in Molecular Medicine* 16:37-45.

Liu Y and Yang J (2006) Hepatocyte growth factor: New arsenal in the fights against renal fibrosis? *Kidney International* 70:238-240.

Lokker N A, Mark M R, Luis E A, Bennett G L, Robbins K A, Baker J B and Godowski P J (1992) Structure-function analysis of hepatocyte growth factor: identification of variants that lack mitogenic activity yet retain high affinity receptor binding. *The EMBO journal* 11:2503-2510.

Maina F, Klein R. (1999) Hepatocyte growth factor, a versatile signal for developing neurons. *Nat. Neurosci.* 2:213-7.

Malgaroli, A. and R. W. Tsien (1992). "Glutamate-induced long-term potentiation of the frequency of miniature synaptic currents in cultured hippocampal neurons." Nature 357(6374): 134-9.

Martens T, Schmidt N-O, Eckerich C, Fillbrandt R, Merchant M, Schwall R, Westphal M and Lamszus K (2006) A Novel One-Armed Anti-c-Met Antibody Inhibits Glioblastoma Growth In vivo. *Clinical cancer research: an official journal of the American Association for Cancer Research.* 12:6144.

Masel B E, DeWitt D S (2010) Traumatic brain injury: a disease process, not an event. *J. Neurotrauma.* 27:1529-1540

Maya B L (2010) Endocrine side effects of broad-acting kinase inhibitors. *Endocrine-Related Cancer* 17:233-244.

Meighan, S. E., P. C. Meighan, et al. (2006). "Effects of extracellular matrix-degrading proteases matrix metalloproteinases 3 and 9 on spatial learning and synaptic plasticity." J Neurochem 96(5): 1227-41.

Meijering, E., M. Jacob, et al. (2004). "Design and validation of a tool for neurite tracing and analysis in fluorescence microscopy images." Cytometry A 58(2): 167-76.

Michieli P, Basilico C, Pennacchietti S, Maffe A, Tamagnone L, Giordano S, Bardelli A and Comoglio P M (1999) Mutant Met-mediated transformation is ligand-dependent and can be inhibited by HGF antagonists. *Oncogene* 18.

Miller C T, Lin L, Casper A M, Lim J, Thomas D G, Orringer M B, Chang A C, Chambers A F, Giordano T J and Glover T W (2006) Genomic amplification of MET with boundaries within fragile site FRA7G and upregulation of MET pathways in esophageal adenocarcinoma. *ONCOGENE-BASINGSTOKE-*25:409-418.

Morotti A, Mila S, Accornero P, Tagliabue E, and Ponzetto C (2002) K252a inhibits the oncogenic properties of Met, the HGF receptor. *Oncogene* 21:4885-4893

Nagahara and Tuszynski (2011) Potential therapeutic uses of BDNF in neurological and psychiatric disorders. *Nat Rev Drug Discov* 10:209-19.

Nakanishi K, Uenoyama M, Tomita N, Morishita R, Kaneda Y, Ogihara T, Matsumoto K, Nakamura T, Maruta A, Matsuyama S, Kawai T, Aurues T, Hayashi T and Ikeda T (2002) Gene Transfer of Human Hepatocyte Growth Factor into Rat Skin Wounds Mediated by Liposomes Coated with the Sendai Virus (Hemagglutinating Virus of Japan). *The American journal of pathology*. 161:1761.

Nicoleau C, Benzakour O, Agasse F, Thiriet N, Petit J, Prestoz L, Roger M, Jaber M, Coronas V. Endogenous hepatocyte growth factor is a niche signal for subventricular zone neural stem cell amplification and self-renewal. (2009) *Stem Cells*. 27:408-19.

Parr C, Watkins G, Mansel R E and Jiang W G (2004) The hepatocyte growth factor regulatory factors in human breast cancer. *Clinical cancer research: an official journal of the American Association for Cancer Research* 10:202-211.

Patel A D, Gerzanich V, Geng Z, Simard J M. (2010) Glibenclamide reduces hippocampal injury and preserves rapid spatial learning in a model of traumatic brain injury. *J Neuropathol Exp Neurol.* 69; 1177-1190.

Pederson, E. S., J. W. Harding, et al. (1998). Attenuation of scopolamine-induced spatial learning impairments by an angiotensin IV analog. *Regul Pept* 74: 97-103.

Peng K Y, Horng L Y, Sung H C, Huang H C, Wu R T. (2011) Hepatocyte growth factor has a role in the amelioration of diabetic vascular complications via autophagic clearance of advanced glycation end products: Dispo85E, an HGF inducer, as a potential botanical drug. *Metabolism*. 60:888-92.

Pietronave S, Forte G, Locarno D, Merlin S, Zamperone A, Nicotra G, Isidoro C, Di Nardo P and Prat M (2010) Agonist monoclonal antibodies against HGF receptor protect cardiac muscle cells from apoptosis. *American journal of physiology*. 298:H1155.

Potempa S and Ridley A J (1998) Activation of Both MAP Kinase and Phosphatidylinositide 3-Kinase by Ras Is Required for Hepatocyte Growth Factor/Scatter Factor-induced Adherens Junction Disassembly. *Molecular biology of the cell/*9:2185.

Qi L, Cui X, Dong W, Barrera R, Nicastro J, Coppa G F, Wang P, Wu R. (2011) Ghrelin Attenuates Brain Injury after Traumatic Brain Injury and Uncontrolled Hemorrhagic Shock in Rats. *Mol. Med*. (Epub ahead of print).

Rangasamy S B, Soderstrom K, Bakay R A E and, Kordower J H. Neurotrophic factor therapy for Parkinson's disease. (2010) *Progress in Brain Research* 184: 237-264.

Ratajczak M Z, Marlicz W, Ratajczak J, Wasik M, Machalinski B, Carter A and Gewirtz A M (1997) Effect of hepatocyte growth factor on early human haemopoietic cell development. *British Journal of Haematology* 99:228-236.

Richardson R M, Singh A, Sun D, Fillmore H L, Dietrich D W 3rd, Bullock M R (2010) Stem cell biology in traumatic brain injury: effects of injury and strategies for repair. *J. Neurosurg*. 112:1125-1138.

Ridley A J, Comoglio P M and Hall A (1995) Regulation of scatter factor/hepatocyte growth factor responses by Ras, Rac, and Rho in MDCK cells. *Molecular and cellular biology* 15:1110-1122.

Rong S, Segal S, Anver M, Resau J H and Woude G F V (1994) Invasiveness and Metastasis of NIH 3T3 Cells Induced by Met-Hepatocyte Growth Factor/Scatter Factor Autocrine Stimulation. *Proceedings of the National Academy of Sciences of the United States of America* 91:4731-4735.

Santos O F, Moura L A, Rosen E M, Nigam S K. (1993) Modulation of HGF-induced tubulogenesis and branching by multiple phosphorylation mechanisms. *Dev Biol* 159: 535-548.

Sattler M, Pride Y B, Ma P, Gramlich J L, Chu S C, Quinnan L A, Shirazian S, Liang C, Podar K, Christensen J G, and Salgia R (2003) A novel small molecule met inhibitor induces apoptosis in cells transformed by the oncogenic TPR-MET tyrosine kinase. *Cancer Research* 63:5462-5469.

Schwarzbach E, Bonislawski D P, Xiong G, Cohen A S (2006) Mechanisms underlying the inability to induce area CA1 LTP in the mouse after traumatic brain injury. *Hippocampus*. 16:541-550.

Shang A, Liu K, Wang H, Wang J, Hang X, Yang Y, Wang Z, Zhang C, Zhou D (2011) Neuroprotective effects of neuroglobin after mechanical injury. *Neurol Sci.* September 14. [Epub ahead of print].

Sheth P R, Hays J L, Elferink L A and Watowich S J (2008) Biochemical Basis for the Functional Switch That Regulates Hepatocyte Growth Factor Receptor Tyrosine Kinase Activation, in *Biochemistry* pp 4028-4038.

Stabile L P, Rothstein M E, Keohavong P, Jin J, Yin J, Land S R, Dacic S, Luong T M, Kim K J, Dulak A M and Siegfried J M (2008) Therapeutic targeting of human hepatocyte growth factor with a single neutralizing monoclonal antibody reduces lung tumorigenesis. *Molecular Cancer Therapeutics* 7:1913-1922.

Stella M C and Comoglio P M (1999) HGF: a multifunctional growth factor controlling cell scattering. *The international journal of biochemistry & cell biology*. 31:1357-1362.

Stubley-Weatherly, L., J. W. Harding, et al. (1996). "Effects of discrete kainic acid-induced hippocampal lesions on spatial and contextual learning and memory in rats." *Brain Res* 716(1-2): 29-38

Sun W, Funakoshi H and Nakamura T (2002) Localization and functional role of hepatocyte growth factor (HGF) and its receptor c-met in the rat developing cerebral cortex. *Molecular Brain Research* 103.

Takeo S, Takagi N and Takagi K (2007) [Ischemic brain injury and hepatocyte growth factor]. *Yakugaku zasshi: Journal of the Pharmaceutical Society of Japan* 127:1813-1823.

Takeuchi D, Sato N, Shimamura M, Kurinami H, Takeda S, Shinohara M, Suzuki S, Kojima M, Ogihara T and Morishita R (2008) Alleviation of Abeta-induced cognitive impairment by ultrasound-mediated gene transfer of HGF in a mouse model. *Gene therapy* 15:561-571.

Tannock I (2005) *The basic science of oncology*. McGraw-Hill, Medical Pub. Division, New York.

Thewke, D. P. and N. W. Seeds (1996). "Expression of hepatocyte growth factor/scatter factor, its receptor, c-met, and tissue-type plasminogen activator during development of the murine olfactory system." *J Neurosci* 16(21): 6933-44.

Thompson J, Dolcet X, Hilton M, Tolcos M and Davies A M (2004) HGF promotes survival and growth of maturing sympathetic neurons by PI-3 kinase- and MAP kinase-dependent mechanisms. *Molecular and Cellular Neurosciences* 27:441-452.

Tong C Y, Hui A B, Yin X L, Pang J C, Zhu X L, Poon W S and Ng H K (2004) Detection of oncogene amplifications in medulloblastomas by comparative genomic hybridization and array-based comparative genomic hybridization. *Journal of neurosurgery* 100:187-193.

Trapp T, Kögler G, El-Khattouti A, Sorg R V, Besselmann M, Föcking M, Bührle C P, Trompeter I, Fischer J C and Wernet P (2008) Hepatocyte Growth Factor/c-MET Axis-mediated Tropism of Cord Blood-derived Unrestricted Somatic Stem Cells for Neuronal Injury. *Journal of Biological Chemistry* 283.

Tyler, W. J. and L. Pozzo-Miller (2003). "Miniature synaptic transmission and BDNF modulate dendritic spine growth and form in rat CA1 neurones." J Physiol 553(Pt 2): 497-509.

Tyndall, S. J. and R. S. Walikonis (2006). "The receptor tyrosine kinase Met and its ligand hepatocyte growth factor are clustered at excitatory synapses and can enhance clustering of synaptic proteins." Cell Cycle 5(14): 1560-8.

Tyndall S J and Walikonis R S (2007) Signaling by hepatocyte growth factor in neurons is induced by pharmacological stimulation of synaptic activity. *Synapse* (New York, N.Y.) 61:199-204.

Ueda H, Nakamura T, Matsumoto K, Sawa Y and Matsuda H (2001) A potential cardioprotective role of hepatocyte growth factor in myocardial infarction in rats. *Cardiovascular research* 51:41-50.

Urbanek, K., M. Rota, et al. (2005). "Cardiac stem cells possess growth factor-receptor systems that after activation regenerate the infarcted myocardium, improving ventricular function and long-term survival." Circ Res 97(7): 663-73.

Wang T W, Zhang H, Gyetko M R, Parent J M. (2011) Hepatocyte growth factor acts as a mitogen and chemoattractant for postnatal subventricular zone-olfactory bulb neurogenesis. *Mol Cell Neurosci.* 48: 38-50.

Wang X, DeFrances M C, Dai Y, Pediaditakis P, Johnson C, Bell A, Michalopoulos G K and Zarnegar R (2002) A mechanism of cell survival: sequestration of Fas by the HGF receptor Met. *Molecular Cell* 9:411-421.

Wayman, G. A., M. Davare, et al. (2008). "An activity-regulated microRNA controls dendritic plasticity by down-regulating p250GAP." Proc Natl Acad Sci USA 105(26): 9093-8

Wayman, G. A., S. Impey, et al. (2006). "Activity-dependent dendritic arborization mediated by CaM-kinase I activation and enhanced CREB-dependent transcription of Wnt-2." Neuron 50(6): 897-909

Wayner, M. J., D. L. Amistrong, et al. (2001). "Angiotensin IV enhances LTP in rat dentate gyrus in vivo." Peptides 22(9): 1403-14.

Weidner K M, Behrens Jr, Vandekerckhove J and Birchmeier W (1990) Scatter Factor: Molecular Characteristics and Effect on the Invasiveness of Epithelial Cells. *The Journal of Cell Biology* 111:2097-2108.

Wright, J. W., J. A. Clemens, et al. (1996). "Effects of LY231617 and angiotensin IV on ischemia-induced deficits in circular water maze and passive avoidance performance in rats." Brain Res 717(1-2): 1-11.

Wright, J. W. and J. W. Harding (1985) "The brain RAS and Alzheimer's disease." Exp Neurol 223(2): 326-33.

Wright, J. W. and J. W. Harding (2008). "The angiotensin AT4 receptor subtype as a target for the treatment of memory dysfunction associated with Alzheimer's disease." J Renin Angiotensin Aldosterone Syst 9(4): 226-37.

Wright, J. W., L. Stubley, et al. (1999). "Contributions of the brain angiotensin IV-AT4 receptor subtype system to spatial learning." J Neurosci 19(10): 3952-61.

Wright, J. W., B. J. Yamamoto, et al. (2008). "Angiotensin receptor subtype mediated physiologies and behaviors: new discoveries and clinical targets." Prog Neurobiol 84(2): 157-81.

Xiao G-H, Jeffers M, Bellacosa A, Mitsuuchi Y, Woude G F V and Testa J R (2001) Anti-Apoptotic Signaling by Hepatocyte Growth Factor/Met via the Phosphatidylinositol 3-Kinase/Akt and Mitogen-Activated Protein Kinase Pathways. *Proceedings of the National Academy of Sciences of the United States of America* 98:247-252.

Xu W and Wu S G (1999) The possible relationship between hepatomegaly and release of HGF into plasma induced by clofibrate in rats, in.

Yamamoto B J, Elias P D, Masino J A, Hudson B D, McCoy A T, Anderson Z J, Varnum M D, Sardinia M F, Wright J W and Harding J W (2010) The Angiotensin IV Analog Nle-Tyr-Leu-ψ—(CH2-NH2)3-4-His-Pro-Phe (Norleual) Can Act as a Hepatocyte Growth Factor/c-Met Inhibitor. The Journal of pharmacology and experimental therapeutics. 333:161.

Yamamoto Y, Livet J, Pollock R A, Garces A, Arce V, deLapeyrière O, Henderson C E. (1997) Hepatocyte growth factor (HGF/SF) is a muscle-derived survival factor for a subpopulation of embryonic motoneurons. *Development* 124: 2903-2913.

Yasumatsu, N., M. Matsuzaki, et al. (2008). "Principles of long-term dynamics of dendritic spines." J Neurosci 28(50): 13592-608.

You W K, McDonald D M (2008) The hepatocyte growth factor/c-Met signaling pathway as a therapeutic target to inhibit angiogenesis. *BMB Rep.* 41:833-839.

Youles M, Holmes O, Petoukhov M V, Nessen M A, Stivala S, Svergun D I and Gherardi E (2008) Engineering the NK1 Fragment of Hepatocyte Growth Factor/Scatter Factor as a MET Receptor Antagonist, in *Journal of Molecular Biology* pp 616-622.

Zhang B, Chen X, Lin Y, Tan T, Yang Z, Dayao C, Liu L, Jiang R, Zhang J (2011) Impairment of synaptic plasticity in hippocampus is exacerbated by methylprednisolone in a rat model of traumatic brain injury. *Brain Res.;* 1382:165-172.

Zhang B L, Chen X, Tan T, Yang Z, Carlos D, Jiang R C, Zhang J N (2011) Traumatic brain injury impairs synaptic plasticity in hippocampus in rats. *Chin Med J (Engl).* 124: 740-745.

Zhang L, Himi T, Morita I and Murota S (2000) Hepatocyte growth factor protects cultured rat cerebellar granule neurons from apoptosis via the phosphatidylinositol-3 kinase/Akt pathway. *Journal of neuroscience research* 59:489-496.

Zhang Y W and Vande Woude G F (2003) HGF/SF-met signaling in the control of branching morphogenesis and invasion. *Journal of Cellular Biochemistry* 88:408-417.

Zhu Y, Hojo Y, Ikeda U and Shimada K (2000) Production of hepatocyte growth factor during acute myocardial infarction. *Heart (British Cardiac Society)* 83:450-455.

The invention claimed is:

1. A hepatocyte growth factor (HGF) mimic having the general formula:

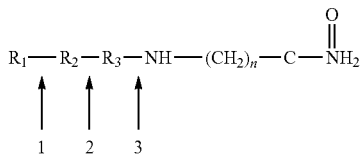

where
- $R_1$ is an amino acid, said amino acid being selected from the group consisting of tyrosine, phenylalanine, aspartic acid, arginine, isoleucine, serine, histidine, glycine, cysteine, methionine, tryptophan, lysine, norvaline, ornithine, and s-benzyl cysteine;
- $R_2$ is an amino acid selected from the group selected from the group consisting of tyrosine, phenylalanine, aspartic acid, arginine, isoleucine, serine, histidine, glycine, cysteine, methionine, tryptophan, lysine and valine;
- $R_3$ is isoleucine; and
- n ranges from 3-6; and
- wherein covalent bonds 1, 2 and 3 are selected from the group consisting of peptide bonds or reduced peptide bonds.

2. N-hexanoic-L-tyrosine-L-isoleucine-(6)-aminohexanoic amide.

3. A composition, comprising:
at least one hepatocyte growth factor (HGF) mimic having the general formula:

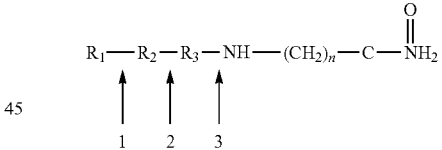

where
- $R_1$ is an amino acid selected from tyrosine, phenylalanine, aspartic acid, arginine, isoleucine, serine, histidine, glycine, cysteine, methionine, tryptophan, lysine, norvaline, ornithine, and s-benzyl cysteine;
- $R_2$ is an amino acid selected from the group selected from the group consisting of tyrosine, phenylalanine, aspartic acid, arginine, isoleucine, serine, histidine, glycine, cysteine, methionine, tryptophan, lysine and valine;
- $R_3$ is isoleucine; and
- n ranges from 3-6; and
- wherein covalent bonds 1, 2 and 3 are selected from the group consisting of peptide bonds or reduced peptide bonds; and
- a carrier, said HGF mimic being dissolved or distributed in said carrier.

4. A composition comprising N-hexanoic-L-tyrosine-L-isoleucine-(6)-aminohexanoic amide and a carrier, said N-hexanoic-L-tyrosine-L-isoleucine-(6)-aminohexanoic amide being dissolved or distributed in said carrier.

* * * * *

UNITED STATES PATENT AND TRADEMARK OFFICE
CERTIFICATE OF CORRECTION

| | | |
|---|---|---|
| PATENT NO. | : 8,598,118 B2 | Page 1 of 1 |
| APPLICATION NO. | : 13/768497 | |
| DATED | : December 3, 2013 | |
| INVENTOR(S) | : Joseph W. Harding et al. | |

It is certified that error appears in the above-identified patent and that said Letters Patent is hereby corrected as shown below:

In the Specification
At column 15, line 3, column 17, line 5, column 19, line 50, column 20, line 5, column 21, line 5, column 22, line 5

In the Claims
Column 67, line 45 and column 68, line 43, the formula should read as follows:

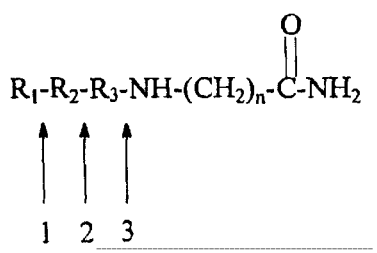

Signed and Sealed this

Thirteenth Day of January, 2015

Michelle K. Lee
*Deputy Director of the United States Patent and Trademark Office*